(12) United States Patent
Klosin et al.

(10) Patent No.: US 8,202,954 B2
(45) Date of Patent: Jun. 19, 2012

(54) METAL-LIGAND COMPLEXES AND CATALYSTS

(75) Inventors: Jerzy Klosin, Midland, MI (US); Ruth Figueroa, Midland, MI (US); Philip P. Fontaine, Manvel, TX (US)

(73) Assignee: Dow Global Technologies LLC

( * ) Notice: Subject to any disclaimer, the term of this patent is extended or adjusted under 35 U.S.C. 154(b) by 0 days.

(21) Appl. No.: 13/023,026

(22) Filed: Feb. 8, 2011

(65) Prior Publication Data

US 2011/0207902 A1    Aug. 25, 2011

Related U.S. Application Data

(60) Provisional application No. 61/306,147, filed on Feb. 19, 2010.

(51) Int. Cl.
*C08F 4/76* (2006.01)
*C08F 4/64* (2006.01)
*C07F 7/00* (2006.01)

(52) U.S. Cl. ........ 526/172; 526/170; 526/161; 526/160; 556/51

(58) Field of Classification Search ................... 556/138, 556/136, 51; 526/160, 161, 172, 170
See application file for complete search history.

(56) References Cited

U.S. PATENT DOCUMENTS

| | | | |
|---|---|---|---|
| 6,096,676 A * | 8/2000 | Murray | 502/117 |
| 6,114,481 A | 9/2000 | McMeeking et al. | |
| 6,340,730 B1 * | 1/2002 | Murray et al. | 526/114 |
| 6,803,433 B2 | 10/2004 | Lee | |
| 6,919,413 B2 | 7/2005 | Murray | |
| 6,919,467 B2 | 7/2005 | Murray | |
| 7,067,686 B1 | 6/2006 | Rodriguez et al. | |
| 7,199,255 B2 | 4/2007 | Murray et al. | |
| 7,355,089 B2 | 4/2008 | Chang et al. | |
| 2002/0034829 A1 * | 3/2002 | Hall et al. | 436/518 |
| 2003/0204017 A1 | 10/2003 | Stevens et al. | |
| 2005/0187362 A1 | 8/2005 | Murray | |
| 2008/0261804 A1 | 10/2008 | Roesky et al. | |
| 2010/0048842 A1 * | 2/2010 | Figueroa et al. | 526/170 |
| 2011/0207903 A1 | 8/2011 | Fontaine et al. | |

FOREIGN PATENT DOCUMENTS

| | | |
|---|---|---|
| WO | 9623010 A2 | 8/1996 |
| WO | 0140325 A1 | 6/2001 |
| WO | 0202577 A1 | 1/2002 |
| WO | 0238628 A2 | 5/2002 |
| WO | 02092610 A1 | 11/2002 |
| WO | 03018643 A1 | 3/2003 |
| WO | 03051935 A1 | 6/2003 |
| WO | 2004024740 A1 | 3/2004 |

(Continued)

OTHER PUBLICATIONS

Adams et al., "Discovery and evaluation of highly active imidotitanium ethylene polymerization catalysts using high throughput catalyst screening", Chemical Communications, 2004, pp. 434-435.

(Continued)

*Primary Examiner* — Rip A. Lee

(57) ABSTRACT

The present invention generally relates to metal-ligand complexes, catalysts comprising or prepared from the metal-ligand complexes, processes of catalyzing olefin polymerization reactions with the catalysts to prepare polyolefins, polyolefins prepared thereby, processes of making the metal-ligand complexes and catalysts, and intermediate compounds useful therefor.

14 Claims, 7 Drawing Sheets

FOREIGN PATENT DOCUMENTS

| | | |
|---|---|---|
| WO | 2004074333 A2 | 9/2004 |
| WO | 2005090425 A1 | 9/2005 |
| WO | 2005090426 A1 | 9/2005 |
| WO | 2005090427 A2 | 9/2005 |
| WO | 2005123790 A1 | 12/2005 |
| WO | 2008027283 A2 | 3/2008 |

OTHER PUBLICATIONS

Al-Omari, M. et al., "Bi-3H-diazirin-3-yls as Precursors of Highly Strained Cycloalkynes", Angewandte Chemie. Int. Ed. 2006, 309-311, 45.

Bradley et al., "Metallo-Organic Compounds Containing Metal-Nitrogen Bonds Part IV. Some Bis-(Primary Amino)-Titanium Compounds", Canadian Journal of Chemistry, 1963, 134-38, vol. 41.

De Waele et al., "Synthesis of Hafnium and Zirconium Imino-Amido Complexes from Bis-imine Ligands. A New Family of Olefin Polymerization Catalysts", Organometallics, 2007, vol. 26, pp. 3896-3899.

Gates et al., "Synthesis of Branched Polyethylene Using (α-Diimine)nickel(II) Catalysts: Influence of Temperature, Ethylene Pressure, and Ligand Structure on Polymer Properties", Macromolecules, 2000, pp. 2320-2334, vol. 33.

Kiesewetter et al., "Ethene/Norbornene Copolymerization with Palladium (II) α-Diimine Catalysts: From Ligand Screening to Discrete Catalyst Species", Chem. Eur. J. 2003, pp. 1750-1758, vol. 9, No. 8, Wiley-VCH Verlag GmbH & Co. KGaA, Weinheim.

Kim et al., "α-Iminoenamido Ligands: A Novel Structure for Transition-Metal Activation", Organometallics, 2002, vol. 21, pp. 3082-3084, American Chemical Society.

Kim et al., "Activation of Enamido Zirconium Complexes for Ethylene Polymerization: Electrophilic Addition Versus Electrophilic Abstraction Reaction", Organometallics, 2003, pp. 1503-1511, vol. 22, XP001144923, American Chemical Society.

Kim et al., Activation of Enamido Zirconium Complexes for Olefin Polymerization: Electrophilic Addition Versus Electrophilic Abstraction Reaction. Polymer Preprints, 2003, pp. 990-991, 44(I) American Chemical Society, Division of Polymer Chemistry.

Mashima et al. "Benzylation of α-Diimine Ligands Bound to Zirconium and Hafnium. A New Convenient Route to Olefin Polymerization Catalysts", Chemistry Letters, 2007, pp. 1420-1421, vol. 36, No. 12.

Nomura et al., "Nonbridged half-metallocenes containing anionic ancillary donor ligands: New promising candidates as catalysts for precise olefin polymerization", Journal of Molecular Catalysis A: Chemical, 2007, 267, pp. 1-29.

Pappalardo et al., "New Neutral and Cationic Dialkylaluminium Complexes Bearing Imino-Amide or Imino-Phenoxide Ligands: Synthesis, Characterization and Reactivity With Olefins", Eur. J. Inorg. Chem. 2002, pp. 621-628.

Steinhuebel et al., "Synthetic and Structural Studies of Titanium Aminotroponiminate Complexes", Inorganic Chemistry, 1999, vol. 38 No. 26, pp. 6225-6233, American Chemical Society.

Steinhuebel et al., "Synthesis of Unsymmetrical Diolate, Oxametallacyclopentene, Amido-Alkoxide and Thiolato-Alkoxide Complexes Using Dialkyl and Diaryl Titanium Aminotroponiminate Complexes: A Route to Unsymmetrical Vicinal Diols", Journal of the American Chemical Society, 1999, vol. 121 No. 50, pp. 11762-11772, American Chemical Society.

Tsurugi et al., "Controlled Benzylation of alpha-Diimine Ligands Bound to Zirconium and Hafnium: An Alternative Method for Preparing Mono- and Bis(amido)M(CH2Ph)n (n=2,3) Complexes as Catalyst Precursors for Isospecific Polymerization of alpha-Olefins", Organometallics, 2009, vol. 28, pp. 680-687.

* cited by examiner

Scheme 1.

Scheme 2.

METAL-LIGAND COMPLEXES AND CATALYSTS

CROSS-REFERENCE TO RELATED APPLICATIONS

This application claims benefit from U.S. Provisional Patent Application No. 61/306,147, filed Feb. 19, 2010, the entire contents of which are hereby incorporated herein by reference.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention generally relates to metal-ligand complexes, catalysts comprising or prepared from the metal-ligand complexes, processes of catalyzing olefin polymerization reactions with the catalysts to prepare polyolefins, polyolefins prepared thereby, processes of making the metal-ligand complexes and catalysts, and intermediate compounds useful in the making thereof.

2. Description of Related Art

U.S. Pat. No. 6,096,676 mentions, among other things, certain catalyst precursors and catalysts comprising a Group 4 metal.

U.S. Pat. No. 6,114,481 mentions, among other things, a method of and certain catalyst system for polymerizing olefins to prepare olefin-derived copolymers. The catalyst system contains a certain organometallic complex of a Group 4 metal and an activator. The organometallic complex contains, among other things, a ketimide ligand (i.e., (Sub 1)(Sub 2)C=N—).

U.S. Pat. No. 6,803,433 B2 mentions, among other things, certain metalloenamine compounds and catalysts comprising a metal that is nickel, palladium, platinum, titanium, zirconium, hafnium, vanadium, or scandium.

U.S. Pat. No. 6,919,413 B2; U.S. Pat. No. 6,919,467 B2; and U.S. Pat. No. 7,199,255 B2 are family members that mention, among other things, certain catalyst precursors and catalysts comprising a metallic element of any one of Groups 1 to 15 and the lanthanide series (of the Periodic Table of the Elements disclosed in Lange's Handbook of Chemistry (McGraw Hill Handbooks, 15$^{th}$ edition, 1999).

Adams N., et al., *Discovery and evaluation of highly active imidotitanium ethylene polymerization catalysts using high throughput catalyst screening*, Chemical Communications, 2004:434-435, mention, among other things, a method of and certain catalyst system for polymerizing ethylene to prepare polyethylenes. The catalyst system contains a certain organometallic complex of the Group 4 metal titanium and an activator. Some of the organometallic complexes contain a single ketimide ligand (i.e., $(R)_2C=N$—).

PCT International Patent Application Publication Number WO 2005/123790 A1 mentions, among other things, a method of and catalyst system for polymerizing olefins to prepare olefin-derived copolymers. The catalyst system contains a certain catalyst covalently bonded to an activator.

Nomura K., et al., *Nonbridged half-metallocenes containing anionic ancillary donor ligands: New promising candidates as catalysts for precise olefin polymerization*, Journal of Molecular Catalysis A: Chemical, 2007; 267:1-29, mention, among other things, certain Group 4 transition metal complexes and olefin polymerizations.

De Waele P., et al., *Synthesis of Hafnium and Zirconium Imino-Amido Complexes from Bis-imine Ligands. A New Family of Olefin Polymerization Catalysts*, Organometallics, 2007; 26:3896-3899, mention, among other things, a method of and certain catalysts for polymerizing olefins.

US 2008/0261804 A1 mentions, among other things, certain oxygen-bridged bimetallic complexes suitable for catalyzing olefin polymerizations.

Chemical industry desires new metal-ligand complexes and catalysts comprising same or prepared therefrom, especially with improved stability (e.g., towards alkyl group migration within same) under olefin polymerization reaction conditions (e.g., temperature). Preferably, the new catalysts would be useful for catalyzing reactions that provide new compositions of matter (e.g., new polyolefin compositions), improving reaction yields, providing alternative substrate selectivities (e.g., providing a new relative selectivity for a monomer and co-monomer in making a polyolefin copolymer), reducing manufacturing costs, improving process safety, or a combination thereof.

SUMMARY OF THE INVENTION

In a first embodiment, the present invention is a metal-ligand complex of formula (I):

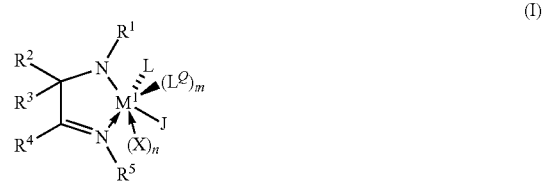

wherein:

Each $L^Q$ independently is absent or L;

Each L independently is absent or is halogen atom, hydrogen atom, $(C_1-C_{40})$hydrocarbylC(O)N(H)—, $(C_1-C_{40})$hydrocarbylC(O)N((C_1-C_{20})hydrocarbyl)$, $(C_1-C_{40})$hydrocarbylC(O)O—, $(C_1-C_{40})$hydrocarbyl, $(C_1-C_{40})$heterohydrocarbyl, $R^K R^L N$—, $R^L O$—, $R^L S$—, or $R^K R^L P$—, wherein each $R^K$ and $R^L$ independently is hydrogen, $(C_1-C_{40})$hydrocarbyl, $[(C_1-C_{10})$hydrocarbyl$]_3$Si, $[(C_1-C_{10})$hydrocarbyl$]_3$Si$(C_1-C_{10})$hydrocarbyl (e.g., trimethylsilylethyl), or $(C_1-C_{40})$heterohydrocarbyl, or $R^K$ and $R^L$ are taken together to form a $(C_2-C_{40})$hydrocarbylene or $(C_1-C_{40})$heterohydrocarbylene, or L and $L^Q$ are taken together to form $(R^D)_2C=C(R^D)—C(R^D)=C(R^D)_2$, wherein each $R^D$ independently is H, unsubstituted $(C_1-C_6)$alkyl, phenyl, or naphthyl; each L independently being a monoanionic moiety that is bonded to $M^1$;

n is an integer of from 0 to 3;

Each X independently is absent or is a neutral Lewis base group that is $R^X NR^K R^L$, $R^K OR^L$, $R^K SR^L$, or $R^X PR^K R^L$, wherein each $R^X$ independently is hydrogen, $(C_1-C_{40})$hydrocarbyl, $[(C_1-C_{10})$hydrocarbyl$]_3$Si, $[(C_1-C_{10})$hydrocarbyl$]_3$Si$(C_1-C_{10})$hydrocarbyl, or $(C_1-C_{40})$heterohydrocarbyl and each $R^K$ and $R^L$ independently is as defined above;

J is a monoanionic moiety of any one of formulas $(J^1)$ to $(J^7)$:

$R^K R^L R^X P\!\!=\!\!N\text{—}$ ($J^1$), wherein each of $R^K$, $R^L$, and $R^X$ independently is as defined above;

$R^K R^L B\text{—}O\text{—}$ ($J^2$), wherein each of $R^K$ and $R^L$ independently is as defined above;

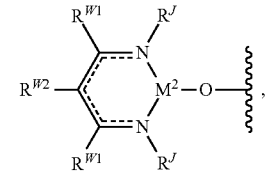
($J^3$)

wherein --- indicates two delocalized pi bonds; each $R^{W1}$ and $R^{W2}$ independently is $R^X$; $M^2$ is Al—$R^A$, Ga—$R^A$, or Zn, wherein each $R^A$ independently is $(C_1-C_{40})$alkyl, $R^K R^L N\text{—}$, or $R^L O\text{—}$; and each $R^J$ independently is a $(C_6-C_{12})$aryl;

$R^K R^L N\text{—}O\text{—}$ ($J^4$), wherein each of $R^K$ and $R^L$ independently is as defined above;

$R^K R^L C\!\!=\!\!N\text{—}$ ($J^5$), wherein each of $R^K$ and $R^L$ independently is as defined above;

$R^K(R^L R^X N)C\!\!=\!\!N\text{—}$ ($J^6$), wherein each of $R^K$, $R^L$, and $R^X$ independently is as defined above; and $(R^L R^X N)_2 C\!\!=\!\!N\text{—}$ ($J^7$), wherein each of $R^K$, $R^L$, and $R^X$ independently is as defined above; or n is 1, 2, or 3 and one X and J are taken together to form a monoanionic bidentate moiety $X^J$-$J^X$ of any one of formulas ($K^1$) to ($K^6$):

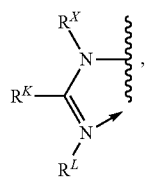
($K^1$)

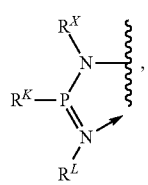
($K^2$)

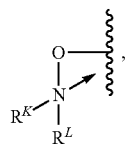
($K^3$)

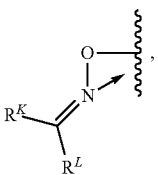
($K^4$)

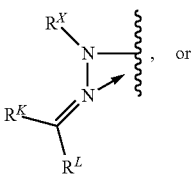
($K^5$)

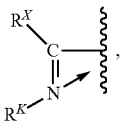
($K^6$)

wherein each of $R^K$, $R^L$, and $R^X$ independently is as defined above;

Each $M^1$ independently is a metal of any one of Groups 3 to 6 of a Periodic Table of the Elements (described later), the metal being in a formal oxidation state of +2, +3, +4, +5, or +6;

m is an integer of from 0 to 3;

Each $R^1$ independently is H, $(C_1-C_{40})$hydrocarbyl, or $(C_1-C_{40})$heterohydrocarbyl;

Each of $R^2$, $R^3$, and $R^4$ independently is $(C_1-C_{40})$hydrocarbyl, $(C_1-C_{40})$hydrocarbylO—, $(C_1-C_{40})$hydrocarbylS—, $(C_1-C_{40})$hydrocarbylS(O)—, $(C_1-C_{40})$hydrocarbylS(O)$_2$—, $((C_1-C_{40})$hydrocarbyl$)_2$N—, $((C_1-C_{40})$hydrocarbyl$)_2$P—, or $(C_1-C_{40})$heterohydrocarbyl; or $R^4$ is as defined previously and $R^2$ and $R^3$ are replaced by (i.e., are taken together to form) a diradical of formula ($R^{23}$):

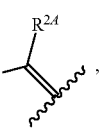
($R^{23}$)

wherein each of $R^{2A}$ and $R^{3A}$ independently is $(C_1-C_{40})$hydrocarbyl, $(C_1-C_{40})$hydrocarbylO—, $(C_1-C_{40})$hydrocarbylS—, $(C_1-C_{40})$hydrocarbylS(O)—, $(C_1-C_{40})$hydrocarbylS(O)$_2$—, $((C_1-C_{40})$hydrocarbyl$)_2$N—, $((C_1-C_{40})$hydrocarbyl$)_2$P—, or $(C_1-C_{40})$heterohydrocarbyl;

Each $R^5$ independently is $(C_1-C_{40})$hydrocarbyl or $(C_1-C_{40})$heterohydrocarbyl;

or $R^1$ and $R^2$; $R^1$ and $R^{2A}$; $R^1$ and $R^4$; $R^2$ and $R^3$; $R^2$ and $R^5$; $R^{2A}$ and $R^{3A}$; $R^{2A}$ and $R^5$; $R^3$ and $R^4$; $R^{3A}$ and $R^4$; $R^4$ and $R^5$; $R^1$ or $R^5$ and an $R^K$ of X or J; or $R^1$ or $R^5$ and an $R^L$ of L or J are taken together to form a $(C_1-C_{40})$hydrocarbylene or $(C_1-C_{40})$heterohydrocarbylene, and the remainder thereof (i.e., the remainder of $R^1$, $R^2$, $R^{2A}$, $R^3$, $R^{3A}$, $R^4$, $R^5$, $R^K$ of X or J, or $R^L$ of L or J) are as defined above;

or $R^1$ or $R^5$ and L are taken together to form $(C_1-C_{40})$ hydrocarbylene-C(O)N(H)—, $(C_1-C_{40})$hydrocarbylene-C(O)N($(C_1-C_{20})$hydrocarbyl), $(C_1-C_{40})$hydrocarbylene-C(O)O—, $(C_1-C_{40})$hydrocarbylene, or $(C_1-C_{40})$heterohydrocarbylene, and the remainder thereof are as defined above;

or any three or four of $R^1$ to $R^5$, $R^{2A}$, $R^{3A}$, $R^K$ of X or J, and $R^L$ of L or J are taken together to form a respective trivalent or tetravalent analog of $(C_1-C_{40})$hydrocarbylene or $(C_1-C_{40})$heterohydrocarbylene, and the remainder thereof are as defined above; or $R^1$ or $R^5$ and any one or two of the remainder of $R^1$ to $R^5$, $R^{2A}$, $R^{3A}$, $R^K$ of X or J, and $R^L$ of L or J are taken together with L to form a respective trivalent or tetravalent analog of $(C_1-C_{40})$hydrocarbylene-C(O)N(H)—, $(C_1-C_{40})$hydrocarbylene-C(O)N($(C_1-C_{20})$hydrocarbyl), $(C_1-C_{40})$hydrocarbylene-C(O)O—, $(C_1-C_{40})$hydrocarbylene, or $(C_1-C_{40})$heterohydrocarbylene; and the remainder of $R^1$ to $R^5$, $R^{2A}$, $R^{3A}$, $R^K$ of X or J, $R^L$ of L or J, and L are as defined above;

Each of the aforementioned $(C_6-C_{12})$aryl, $(C_1-C_{10})$hydrocarbyl, $(C_1-C_{20})$hydrocarbyl, $(C_1-C_{40})$hydrocarbyl, $(C_1-C_{40})$heterohydrocarbyl, $(C_1-C_{40})$hydrocarbylene, $(C_2-C_{40})$hydrocarbylene, and $(C_1-C_{40})$heterohydrocarbylene is the same or different and independently is unsubstituted or substituted with one or more substituents $R^S$;

Each $R^S$ independently is halogen atom, polyfluoro, perfluoro, unsubstituted $(C_1-C_{18})$hydrocarbyl, $F_3C$—, $FCH_2O$—, $F_2HCO$—, $F_3CO$—, oxo (i.e., =O), $R_3Si$—, RO—, RS—, RS(O)—, $RS(O)_2$—, $R_2P$—, $R_2N$—, $R_2C$=N—, NC—, RC(O)O—, ROC(O)—, RC(O)N(R)—, or $R_2NC(O)$—, wherein each R independently is an unsubstituted $(C_1-C_{18})$hydrocarbyl;

each ⌇⌇⌇ independently indicates a bond fragment; and each L, $L^Q$, and m being selected, depending on the formal oxidation state of metal $M^1$, such that the metal-ligand complex of formula (I) is, in aggregate, neutral (e.g., m is 0 when $L^Q$ is absent).

In a second embodiment, the present invention is a catalyst comprising, or prepared from, one or more metal-ligand complexes of formula (I) and one or more activating co-catalysts, or a reaction product thereof, wherein the ratio of total number of moles of the one or more metal-ligand complexes to total number of moles of the one or more activating co-catalyst is from 1:10,000 to 100:1.

In a third embodiment, the present invention is a process of preparing a polyolefin, the process comprising a step of contacting at least one polymerizable olefin (i.e., an olefin monomer) to the catalyst of the second embodiment under olefin-polymerizing conditions (described later) sufficient to polymerize at least some of the at least one polymerizable olefin, thereby producing a polyolefin therefrom.

In a fourth embodiment, the present invention is a process of preparing the catalyst of the second embodiment, the process comprising a step of contacting one or more metal-ligand complexes of formula (I) to one or more activating co-catalysts under conditions sufficient to prepare the catalyst of the second embodiment, wherein the ratio of total moles of the one or more metal-ligand complexes of formula (I) to total moles of the one or more activating co-catalysts is from 1:10,000 to 100:1.

In a fifth embodiment, the present invention is a process of preparing the metal-ligand complex of formula (I), the process comprising a step of contacting an intermediate metal-ligand complex of formula (Z):

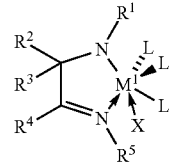

(Z)

to a compound of formula J-H or $X^J-J^X$-H, wherein J and $X^J-J^X$ are as defined in the first embodiment and the compound of formula J-H or $X^J-J^X$-H respectively is the conjugate Brønsted acid of group J or $X^J-J^X$, the contacting being performed under conditions sufficient to produce a mixture comprising the metal-ligand complex of formula (I) as described above for the first embodiment.

Another embodiment of the present invention is a polyolefin prepared according to a process of the third embodiment.

The metal-ligand complex of formula (I) is useful for preparing the catalyst of the second embodiment. The catalyst of the second embodiment is useful in the process of the third embodiment for preparing a polyolefin. As can be illustrated later, the invention process of the third embodiment is characterizable by one or more activities of the catalyst(s), one or more properties of the polyolefin prepared thereby, or a combination thereof.

The polyolefins produced by the invention process of the third embodiment are useful for preparing, for example, lubricants, coatings, films, fibers, and molded and extruded articles, including articles where polyolefins having higher $M_w$ or $M_n$ are desired. Examples of such articles are those requiring higher than ambient service temperatures (e.g., temperatures higher than about 30° C.). Additional examples are synthetic lubricants and, especially for the olefin block copolymers (OBCs), elastic films for hygiene applications (e.g., for diaper covers); flexible molded goods for appliances, tools, consumer goods (e.g., toothbrush handles), sporting goods, building and construction, automotive, and medical applications; flexible gaskets and profiles for appliance (e.g., refrigerator door gaskets and profiles), building and construction, and automotive applications; adhesives for packaging (e.g., for use in manufacturing corrugated cardboard boxes), hygiene applications, tapes, and labels; and foams for sporting goods (e.g., foam mats), packaging, consumer goods, and automotive applications. Other examples are applications requiring improved mechanical properties such as, for example, one or more of modulus (e.g., Young's modulus), Izod impact strength, yield strength, tensile strength, elongation at break, stiffness, heat resistance, chemical resistance, ignition resistance, resistance to diffusion of polar liquids or gases, and dimensional stability.

Additional non-limiting embodiments are described below, including the claims, and in the drawings that accompany this specification.

DETAILED DESCRIPTION OF THE INVENTION

Figure 1:
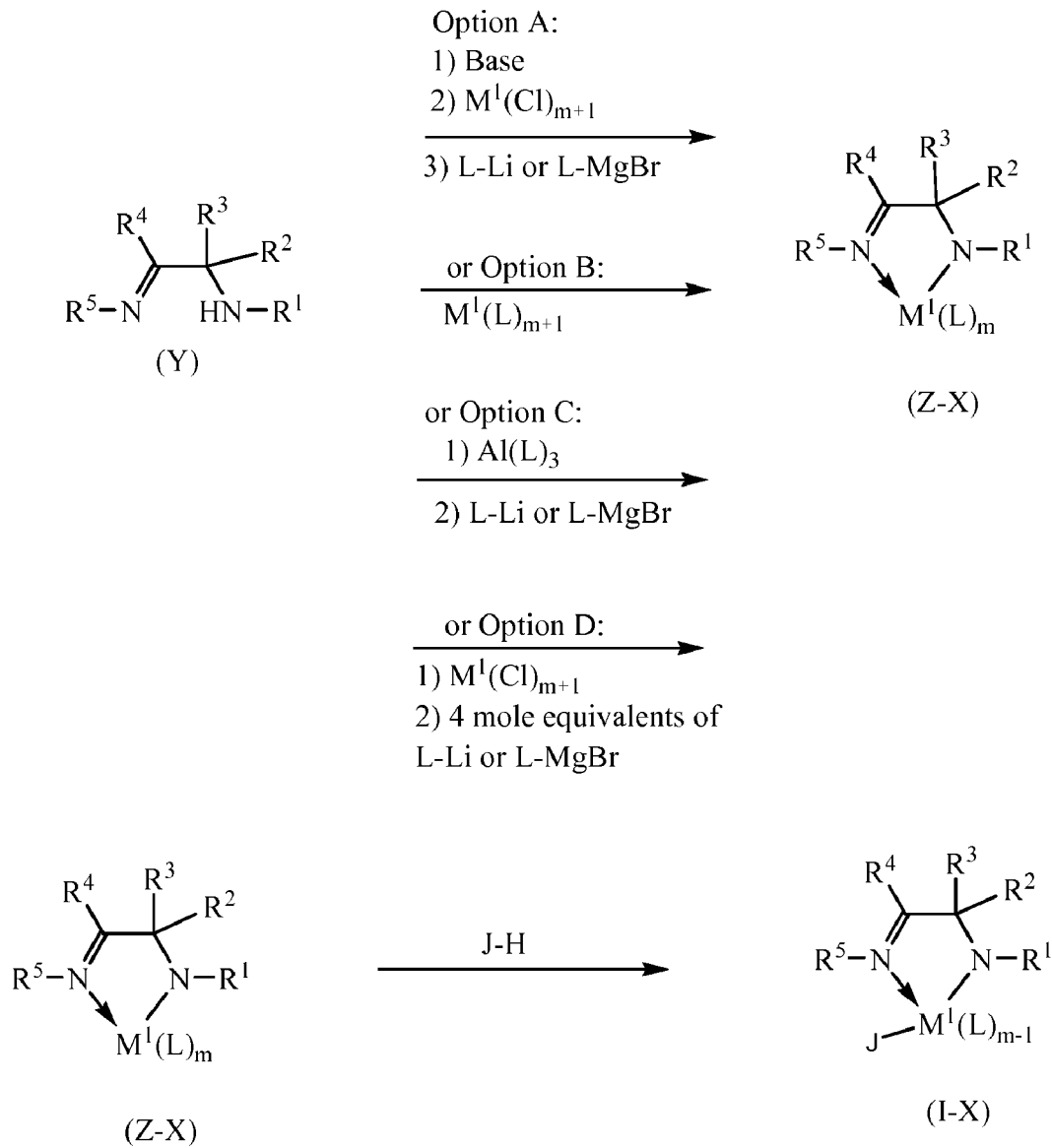
FIG. 1 shows illustrative procedures in Scheme 1 for preparing the metal-ligand complexes of formula (I).

As summarized previously, the present invention generally relates to metal-ligand complexes, catalysts comprising or prepared from the metal-ligand complexes, processes of catalyzing olefin polymerization reactions with the catalysts to prepare polyolefins, polyolefins prepared thereby, processes of making the metal-ligand complexes and catalysts, and intermediate compounds useful therefor.

Preferably, the catalyst of the second embodiment comprises, or is prepared from, three or fewer, more preferably two, and still more preferably one metal-ligand complex of formula (I). Preferred invention catalysts of the second embodiment show beneficial catalyst efficiencies as polymerization catalysts (e.g., higher grams of polymer produced per gram of metal-ligand complexes of formula (I) that are used to prepare the invention catalysts) and produce polyolefins, including polyolefin copolymers, having beneficially higher weight average molecular weights ($M_w$), number average molecular weights ($M_n$), or both compared to $M_w$ or $M_n$ of conventional polyolefins.

Preferably, the polyolefin prepared by the process of the third embodiment is an ethylene homopolymer, an ethylene/alpha-olefin interpolymer (e.g., copolymer), or an ethylene/alpha-olefin/diene interpolymer (e.g., terpolymer).

Preferably, the process of the fourth embodiment employs an aprotic solvent (i.e., a solvent lacking —OH, —NH, and —SH functional groups).

In some embodiments, the process of the third embodiment further employs another polymerizable olefin (i.e., an olefin comonomer) so as to employ both an olefin monomer and olefin comonomer, a chain shuttling agent (CSA, described later), and an associate olefin polymerization catalyst (which may be an invention catalyst, or a non-invention catalyst described later), the preferred process giving the polyolefin wherein the polyolefin comprises a poly(olefin monomer olefin comonomer) interpolymer (e.g., copolymer), more preferably a poly(olefin monomer olefin comonomer) block copolymer (i.e., an OBC), and in some embodiments a poly(ethylene alpha-olefin) block copolymer. The poly(ethylene alpha-olefin) block copolymer preferably comprises an ethylene-derived hard segment and a soft segment comprising residuals from the alpha-olefin and ethylene as described later. The term "poly(ethylene alpha-olefin) block copolymer" is used interchangeably herein with the terms "olefin block copolymer," "OBC," "ethylene/α-olefin block interpolymer," and "ethylene/α-olefin block copolymer". The terms "alpha-olefin" and "α-olefin" are used interchangeably herein.

As used herein, "a," "an," "the," "at least one," and "one or more" are used interchangeably. In any embodiment described herein, the open-ended (non-excluding) terms "comprising," "comprises," and the like (which are synonymous with "including," "having," and "characterized by") may be replaced by the respective partially closed (partially excluding) phrases "consisting essentially of," "consists essentially of," and the like or the respective closed (excluding) phrases "consisting of," "consists of," and the like. The term "or" used in a listing of members, unless stated otherwise, refers to the listed members individually as well as in any combination, and supports additional embodiments reciting any one of the individual members (e.g., in an embodiment reciting the phrase "10 percent or more," the "or" supports another embodiment reciting "10 percent" and still another embodiment reciting "more than 10 percent."). The term "plurality" means two or more, wherein each plurality is independently selected unless indicated otherwise. The terms "first," "second," et cetera serve as a convenient means of distinguishing between two or more elements or limitations (e.g., a first chair and a second chair) and do not imply quantity or order unless specifically so indicated.

For purposes of U.S. patent practice and other patent practices allowing incorporation of subject matter by reference, and the entire contents—unless otherwise indicated—of each U.S. patent, U.S. patent application, U.S. patent application publication, Patent Cooperation Treaty (PCT) international patent application and WO publication equivalent thereof, referenced in the instant Detailed Description of the Invention are hereby incorporated by reference. When available, a U.S. patent or U.S. patent application publication family member thereof may be incorporated by reference instead of the PCT international patent application or WO publication equivalent. In an event where there is a conflict between what is written in the present specification and what is written in a patent, patent application, or patent application publication, or a portion thereof that is incorporated by reference, what is written in the present specification controls.

The word "optionally" means "with or without." For example, "optionally, an additive" means with or without an additive.

In an event where there is a conflict between a unit value that is recited without parentheses, e.g., 2 inches, and a corresponding unit value that is parenthetically recited, e.g., (5 centimeters), the unit value recited without parentheses controls.

In an event where there is a conflict between a compound name and its structure, the structure controls.

In the present application, any lower limit of a range, or any preferred lower limit of the range, may be combined with any upper limit of the range, or any preferred upper limit of the range, to define a preferred embodiment of the range. Each range of numbers includes all numbers, both rational and irrational numbers, subsumed within that range (e.g., the range from about 1 to about 5 includes, for example, 1, 1.5, 2, 2.75, 3, 3.80, 4, and 5).

Certain unsubstituted chemical groups are described herein as having a maximum number of 40 carbon atoms (e.g., ($C_1$-$C_{40}$)hydrocarbyl and ($C_1$-$C_{40}$)heterohydrocarbyl). These include substituent groups (e.g., R groups) and olefin monomers where number of carbon atoms is not critical. Forty carbon atoms in such unsubstituted chemical groups is a practical upper limit; nevertheless in some embodiments the invention contemplates such unsubstituted chemical groups having a maximum number of carbon atoms that is higher than 40 (e.g., 100, 1000, or more).

Unless otherwise noted, the phrase "Periodic Table of the Elements" refers to the official periodic table, version dated Jun. 22, 2007, published by the International Union of Pure and Applied Chemistry (IUPAC). Also any references to a Group or Groups shall be to the Group or Groups reflected in this Periodic Table of the Elements.

In some embodiments $M^1$ is a metal of Group 3. Group 3 metals (symbol), including lanthanoids and actinoids, useful in the present invention are scandium (Sc), yttrium (Y), the lanthanides (sometimes called lanthanoids), especially lanthanum (La), cerium (Ce), praseodymium (Pr), neodymium (Nd), promethium (Pm), samarium (Sm), europium (Eu), gadolinium (Gd), terbium (Tb), dysprosium (Dy), holium (Ho), erbium (Er), thulium (Tm), ytterbium (Yb), and lutetium (Lu), and the stable actinides (sometimes called actinoids), especially stable isotopes of actinium (Ac), thorium (Th), and uranium (U). Unstable actinides such as protactinium (Pa), neptunium (Np), plutonium (Pu), americium (Am), curium (Cm), berkelium (Bk), californium (CO, einsteinium (Es) fermium (Fm), mendelevium (Md), nobelium (No), and lawrencium (Lr) are excluded from the actinides useful in the present invention. Preferred Group 3 metals are Sc and Y. In other embodiments $M^1$ is a metal of Group 4. Preferred Group 4 metals are those in a formal oxidation state of +2, +3, or +4, more preferably +4. For purposes of the present invention, rutherfordium (Rf) is excluded from the Group 4 metals useful in the present invention. In still other embodiments $M^1$ is a metal of Group 5. Group 5 metals useful in the present invention are vanadium (V), niobium (Nb), and tantalum (Ta). For purposes of the present invention, dubnium (Db) is excluded from the Group 5 metals useful in the present invention. In still other embodiments $M^1$ is a metal of Group 6. Group 6 metals useful in the present invention are chromium (Cr), molybdenum (Mo), and tungsten (W). For purposes of the present invention, seaborgium (Sg) is excluded from the Group 6 metals useful in the present invention.

More preferably, $M^1$ is a metal of Group 4, which means that $M^1$ is titanium (Ti), zirconium (Zr), or hafnium (Hf), and more preferably zirconium or hafnium.

When used to describe a chemical group (e.g., $(C_1-C_{40})$ alkyl), the parenthetical expression of the form "$(C_x-C_y)$," means that the unsubstituted version of the chemical group comprises from a number x carbon atoms to a number y carbon atoms, wherein each x and y independently is an integer as described for the chemical group. Thus, for example, an unsubstituted $(C_1-C_{40})$alkyl contains from 1 to 40 carbon atoms. When one or more substituents on the chemical group contain one or more carbon atoms, the substituted $(C_x-C_y)$ chemical group may or may not comprise more than y total carbon atoms; i.e., the maximum total number of carbon atoms of the substituted $(C_x-C_y)$ chemical group would be equal to y plus the sum of the number of carbon atoms of each of the substituent(s). Any atom of a chemical group that is not specified herein is understood to be a hydrogen atom.

In some embodiments, an invention compound (e.g., the metal-ligand complex of formula (I) contains one or more of the substituents $R^S$. Preferably there are not more than 20 $R^S$, more preferably not more than 10 $R^S$, and still more preferably not more than 5 $R^S$ in the compound. Where the invention compound contains two or more substituents $R^S$, each $R^S$ independently is bonded to a same or different substituted chemical group.

In some embodiments, at least one $R^S$ is polyfluoro or perfluoro. For present purposes "polyfluoro" and "perfluoro" each count as one $R^S$ substituent. The term "poly" as in "polyfluoro" means that two or more H, but not all H, bonded to carbon atoms of a corresponding unsubstituted chemical group are replaced by a fluoro in the substituted chemical group. The term "per" as in "perfluoro" means each H bonded to carbon atoms of a corresponding unsubstituted chemical group is replaced by a fluoro in the substituted chemical group.

As used herein, the term "$(C_1-C_{40})$hydrocarbyl" means a hydrocarbon radical of from 1 to 40 carbon atoms and the term "$(C_1-C_{40})$hydrocarbylene" means a hydrocarbon diradical of from 1 to 40 carbon atoms, wherein each hydrocarbon radical and diradical independently is aromatic or non-aromatic, saturated or unsaturated, straight chain or branched chain, cyclic (including mono- and poly-cyclic, fused and non-fused polycyclic) or acyclic, or a combination of two or more thereof; and each hydrocarbon radical and diradical is the same as or different from another hydrocarbon radical and diradical, respectively, and independently is unsubstituted or substituted by one or more $R^S$.

Preferably, a $(C_1-C_{40})$hydrocarbyl independently is an unsubstituted or substituted $(C_1-C_{40})$alkyl, $(C_3-C_{40})$cycloalkyl, $(C_3-C_{20})$cycloalkyl-$(C_1-C_{20})$alkylene, $(C_6-C_{40})$aryl, or $(C_6-C_{20})$aryl-$(C_1-C_{20})$alkylene. More preferably, a $(C_1-C_{40})$hydrocarbyl independently is an unsubstituted or substituted $(C_1-C_{20})$hydrocarbyl, e.g., $(C_1-C_{20})$alkyl, $(C_3-C_{20})$cycloalkyl, $(C_3-C_{10})$cycloalkyl-$(C_1-C_{10})$alkylene, $(C_6-C_{20})$aryl, or $(C_6-C_{18})$aryl-$(C_1-C_{10})$alkylene. Still more preferably, a $(C_1-C_{40})$hydrocarbyl independently is an unsubstituted or substituted $(C_1-C_{18})$hydrocarbyl, e.g., $(C_1-C_{18})$alkyl, $(C_3-C_{18})$cycloalkyl, $(C_3-C_{12})$cycloalkyl-$(C_1-C_6)$alkylene, $(C_6-C_{18})$aryl, or $(C_6-C_{12})$aryl-$(C_1-C_6)$alkylene. Preferably, any $(C_3-C_{18})$cycloalkyl independently is an unsubstituted or substituted $(C_3-C_{10})$cycloalkyl.

The term "$(C_1-C_{40})$alkyl" means a saturated straight or branched hydrocarbon radical of from 1 to 40 carbon atoms that is unsubstituted or substituted by one or more $R^S$. Examples of unsubstituted $(C_1-C_{40})$alkyl are unsubstituted $(C_1-C_{20})$alkyl; unsubstituted $(C_1-C_{10})$alkyl; unsubstituted $(C_1-C_5)$alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted $(C_1-C_{40})$alkyl are substituted $(C_1-C_{20})$alkyl, substituted $(C_1-C_{10})$alkyl, trifluoromethyl, and $(C_{45})$alkyl. Preferably, each $(C_1-C_5)$alkyl independently is methyl, trifluoromethyl, ethyl, 1-propyl, or 2-methylethyl.

The term "$(C_1-C_{20})$alkylene" means a saturated straight or branched chain diradical of from 1 to 20 carbon atoms that is unsubstituted or substituted by one or more $R^S$. Preferably, $(C_1-C_{20})$alkylene, together with atoms of formula (I) through which the $(C_1-C_{20})$alkylene is bonded, comprise a 5- or 6-membered ring. Examples of unsubstituted $(C_1-C_{20})$alkylene are unsubstituted $(C_1-C_{10})$alkylene, including unsubstituted 1,2-$(C_1-C_{10})$alkylene; —$CH_2$—, —$CH_2CH_2$—, —$(CH_2)_3$—,

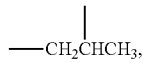

—$(CH_2)_4$—, —$(CH_2)_5$—, —$(CH_2)_6$—, —$(CH_2)_7$—, —$(CH_2)_8$—, and —$(CH_2)_4C(H)(CH_3)$—. Examples of substituted $(C_1-C_{20})$alkylene are substituted $(C_1-C_{10})$alkylene, —$CF_2$—, —$C(O)$—, and —$(CH_2)_{14}C(CH_3)_2(CH_2)_5$— (i.e., a 6,6-dimethyl substituted normal-1,20-eicosylene).

The term "$(C_6-C_{40})$aryl" means an unsubstituted or substituted (by one or more $R^S$) mono-, bi- or tricyclic aromatic hydrocarbon radical of from 6 to 40 total carbon atoms, of which at least from 6 to 14 carbon atoms are ring carbon atoms, and the mono-, bi- or tricyclic radical comprises 1, 2 or 3 rings (first, second, and third rings, respectively), wherein any second or third ring independently is fused or non-fused to a first ring or each other, and the first ring is aromatic and, preferably, at least one of any second or third rings is aromatic. Examples of unsubstituted $(C_6-C_{40})$aryl are unsubstituted $(C_6-C_{20})$aryl; unsubstituted $(C_6-C_{18})$aryl; unsubstituted $(C_6-C_{12})$aryl; phenyl; fluorenyl; tetrahydrofluorenyl; indacenyl; hexahydroindacenyl; indenyl; dihydroindenyl; naphthyl; tetrahydronaphthyl; and phenanthrene. Examples of substituted $(C_6-C_{40})$aryl are substituted $(C_6-C_{20})$aryl; substituted $(C_6-C_{18})$aryl; substituted $(C_6-C_{12})$aryl; 2-$(C_1-C_5)$alkyl-phenyl; 2,4-bis$(C_1-C_5)$alkyl-phenyl; 2,4-bis[$(C_{20})$alkyl]-phenyl; polyfluorophenyl; pentafluorophenyl; and fluoren-9-one-1-yl. A preferred substituted $(C_6-C_{12})$aryl is a substituted $(C_6)$aryl, more preferably 2,6-bis(1-methylethyl)phenyl.

The term "$(C_3-C_{40})$cycloalkyl" means a saturated cyclic hydrocarbon radical of from 3 to 40 carbon atoms that is unsubstituted or substituted by one or more $R^S$. Examples of unsubstituted $(C_3-C_{40})$cycloalkyl are unsubstituted $(C_3-C_{20})$cycloalkyl, unsubstituted $(C_3-C_{10})$cycloalkyl, cyclopropyl, cyclobutyl, cyclopentyl, cyclohexyl, cycloheptyl, cyclooctyl, cyclononyl, and cyclodecyl. Examples of substituted $(C_3-C_{40})$cycloalkyl are substituted $(C_3-C_{20})$cycloalkyl, substituted $(C_3-C_{10})$cycloalkyl, cyclopentanon-2-yl, and 1-fluorocyclohexyl.

Examples of $(C_1-C_{40})$hydrocarbylene are unsubstituted or substituted $(C_6-C_{40})$arylene, $(C_3-C_{40})$cycloalkylene, and $(C_1-C_{40})$alkylene (e.g., $(C_1-C_{20})$alkylene). In some embodiments, the diradicals are on adjacent carbon atoms (i.e., 1,2-diradicals), or spaced apart by one, two, or more intervening carbon atoms (e.g., respective 1,3-diradicals, 1,4-diradicals, etc.). Preferred is a 1,2-, 1,3-, 1,4-, or an alpha,omega-diradical (i.e., having maximum spacing between the radical carbons), more preferably a 1,2-diradical. More preferred are 1,2-diradical versions of $(C_6-C_{18})$arylene, $(C_3-C_{20})$cycloalkylene, and $(C_2-C_{20})$alkylene.

The term "$(C_1-C_{40})$heterohydrocarbyl" means a heterohydrocarbon radical of from 1 to 40 carbon atoms and one or more heteroatoms N (when comprising —N=, as in certain nitrogen containing heteroaryl groups, e.g., an isoxazolyl); O; S; S(O); S(O)$_2$; Si$(R^C)_2$; P$(R^P)$; and N$(R^N)$, wherein independently each $R^C$ is unsubstituted $(C_1-C_{18})$hydrocarbyl, each $R^P$ is unsubstituted $(C_1-C_{18})$hydrocarbyl; and each $R^N$ is unsubstituted $(C_1-C_{18})$hydrocarbyl. The term "$(C_1-C_{40})$heterohydrocarbylene" means a heterohydrocarbon diradical of from 1 to 40 carbon atoms and one or more heteroatoms Si$(R^C)_2$, P$(R^P)$, N$(R^N)$, N, O, S, S(O), and S(O)$_2$ as defined above. The heterohydrocarbon radical and each of the heterohydrocarbon diradicals independently are on a carbon atom or heteroatom thereof. Each heterohydrocarbon radical and diradical independently is unsubstituted or substituted (by one or more $R^S$), aromatic or non-aromatic, saturated or unsaturated, straight chain or branched chain, cyclic (including mono- and poly-cyclic, fused and non-fused polycyclic) or acyclic, or a combination of two or more thereof; and each heterohydrocarbon is the same as or different from another heterohydrocarbon radical and diradical, respectively.

Preferably, a $(C_1-C_{40})$heterohydrocarbyl independently is unsubstituted or substituted $(C_1-C_{40})$heteroalkyl, $(C_2-C_{40})$heterocycloalkyl, $(C_2-C_{40})$heterocycloalkyl-$(C_1-C_{20})$alkylene, $(C_3-C_{40})$cycloalkyl-$(C_1-C_{20})$heteroalkylene, $(C_2-C_{40})$heterocycloalkyl-$(C_1-C_{20})$heteroalkylene, $(C_1-C_{40})$heteroaryl, $(C_1-C_{20})$heteroaryl-$(C_1-C_{20})$alkylene, $(C_6-C_{20})$aryl-$(C_1-C_{20})$heteroalkylene, or $(C_1-C_{20})$heteroaryl-$(C_1-C_{20})$heteroalkylene. More preferably, a $(C_1-C_{40})$heterohydrocarbyl independently is unsubstituted or substituted $(C_1-C_{20})$heterohydrocarbyl, e.g., $(C_1-C_{20})$heteroalkyl, $(C_2-C_{20})$heterocycloalkyl, $(C_2-C_{20})$heterocycloalkyl-$(C_1-C_{20})$alkylene, $(C_3-C_{20})$cycloalkyl-$(C_1-C_{20})$heteroalkylene, $(C_2-C_{20})$heterocycloalkyl-$(C_1-C_{20})$heteroalkylene, $(C_1-C_{20})$heteroaryl, $(C_1-C_{20})$heteroaryl-$(C_1-C_{20})$alkylene, $(C_6-C_{20})$aryl-$(C_1-C_{20})$heteroalkylene, or $(C_1-C_{20})$heteroaryl-$(C_1-C_{20})$heteroalkylene. Still more preferably, a $(C_1-C_{40})$heterohydrocarbyl independently is unsubstituted or substituted $(C_1-C_{18})$heterohydrocarbyl, e.g., $(C_1-C_{18})$heteroalkyl, $(C_2-C_{18})$heterocycloalkyl, $(C_2-C_{12})$heterocycloalkyl-$(C_1-C_6)$alkylene, $(C_3-C_{12})$cycloalkyl-$(C_1-C_6)$heteroalkylene, $(C_2-C_{12})$heterocycloalkyl-$(C_1-C_6)$heteroalkylene, $(C_1-C_{12})$hetero aryl, $(C_1-C_{12})$heteroaryl-$(C_1-C_6)$alkylene, $(C_6-C_{18})$aryl-$(C_1-C_6)$heteroalkylene, or $(C_1-C_{12})$heteroaryl-$(C_1-C_6)$heteroalkylene. Preferably, any $(C_2-C_{18})$heterocycloalkyl independently is unsubstituted or substituted $(C_2-C_9)$heterocycloalkyl.

Examples of $(C_1-C_{40})$heteroalkyl and $(C_1-C_{20})$heteroalkylene are saturated straight or branched chain radical or diradical, respectively, of from 1 to 40 or 1 to 20 carbon atoms, respectively, and one or more of the heteroatoms Si$(R^C)_2$, P$(R^P)$, N$(R^N)$, N, O, S, S(O), and S(O)$_2$ as defined above, wherein the $(C_1-C_{40})$heteroalkyl and $(C_1-C_{20})$heteroalkylene independently are unsubstituted or substituted by one or more $R^S$.

Examples of unsubstituted $(C_2-C_{40})$heterocycloalkyl are unsubstituted $(C_2-C_{20})$heterocycloalkyl, unsubstituted $(C_2-C_{10})$heterocycloalkyl, aziridin-1-yl, oxetan-2-yl, tetrahydrofuran-3-yl, pyrrolidin-1-yl, tetrahydrothiophen-S,S-dioxide-2-yl, morpholin-4-yl, 1,4-dioxan-2-yl, hexahydroazepin-4-yl, 3-oxa-cyclooctyl, 5-thia-cyclononyl, and 2-aza-cyclodecyl.

Examples of unsubstituted $(C_1-C_{40})$heteroaryl are unsubstituted $(C_1-C_{20})$heteroaryl, unsubstituted $(C_1-C_{10})$heteroaryl, pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; tetrazol-5-yl; pyridine-2-yl; pyrimidin-2-yl; pyrazin-2-yl; indol-1-yl; benzimidazole-1-yl; quinolin-2-yl; and isoquinolin-1-yl.

The term "halogen atom" means a fluoro (F), chloro (Cl), bromo (Br), or iodo (I) radical. Preferably, halogen atom is fluoro or chloro, more preferably fluoro.

Preferably, there are no O—O, S—S, or O—S bonds, other than O—S bonds in an S(O) or S(O)$_2$ diradical functional group, in the metal-ligand complex of formula (I).

Preferably, each substituted $(C_1-C_{40})$hydrocarbyl excludes and is different than unsubstituted or substituted $(C_1-C_{40})$heterohydrocarbyl; preferably, each substituted $(C_1-C_{40})$hydrocarbylene excludes and is different than unsubstituted or substituted $(C_1-C_{40})$heterohydrocarbylene; and more preferably a combination thereof.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents $R^S$, one or more double and/or triple bonds optionally may or may not be present in the substituents $R^S$. The term "unsaturated" means containing one or more carbon-carbon double bonds, carbon-carbon triple bonds, and (in heteroatom-containing groups) carbon-nitrogen, carbon-phosphorous, and carbon-silicon double bonds, not including any such double bonds that may or may not be present in the substituents $R^S$ or in (hetero) aromatic rings, if any.

Some embodiments contemplate a trivalent or tetravalent analog of a diradical group. As applied to the diradical group, the term "trivalent or tetravalent analog" respectively means a triradical or tetraradical that is formally derived by abstracting one or two hydrogen atoms, respectively, from the diradical group. Preferably, each abstracted hydrogen atom independently is taken from a C—H functionality. A trivalent analog is preferred over a tetravalent analog.

In some embodiments, at least one, more preferably at least two, still more preferably all of $R^1$ to $R^5$, X, L, $L^Q$, and J independently are unsubstituted (i.e., lack substituents $R^S$). In other embodiments, at least one, more preferably two, and still more preferably 3 of $R^1$ to $R^5$, X, L, $L^Q$, and J are independently substituted with the substituent $R^S$, each substituent $R^S$ independently and preferably being a $(C_1-C_{10})$alkyl, and more preferably a $(C_1-C_5)$alkyl.

In other embodiments, the metal-ligand complex of formula (I) is as described in the first embodiment, except wherein one radical group (e.g., $(C_1-C_{40})$hydrocarbylC(O)O—, $(C_1-C_{40})$hydrocarbyl, or $(C_1-C_{40})$hydrocarbylene) is deleted from the definition of any one of $R^1$ to $R^5$, L, $L^Q$, and J.

The term "solvent" means a liquid, preferably aprotic, that is compatible with the process of any one of the third, fourth and fifth embodiments. Suitable solvents include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; benzene and $(C_1-C_5)$alkyl-substituted benzenes such as toluene and xylene; $(C_1-C_5)$alkyl-O—$(C_1-C_5)$alkyl; $(C_4-C_5)$heterocycloalkyl such as tetrahydrofuran, tetrahydropyran, and 1,4-dioxane; $(C_1-C_5)$alkyl ethers of (poly)alkylene glycols; and mixtures of the foregoing.

The metal-ligand complexes of formula (I) are rendered catalytically active by contacting them to, or combining them with, an activating co-catalyst or by using an activating technique such as those that are known in the art for use with metal (e.g., Group 4) olefin polymerization reactions. The present invention contemplates replacing one or more of the activating co-catalysts with the activating technique, although use of activating co-catalysts is preferred. Suitable activating co-catalysts for use herein include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is bulk electrolysis (explained in more detail hereinafter). Combinations of one or more of the foregoing activating co-catalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Aluminoxanes and their preparations are known at, for example, U.S. Pat. No. 6,103,657. Examples of preferred polymeric or oligomeric alumoxanes are methylalumoxane, triisobutylaluminum-modified methylalumoxane, and isobutylalumoxane.

Preferred Lewis acid activating co-catalysts are Group 13 metal compounds containing from 1 to 3 hydrocarbyl substituents as described herein. More preferred Group 13 metal compounds are tri(hydrocarbyl)-substituted-aluminum or tri(hydrocarbyl)-boron compounds, still more preferred are tri$((C_1-C_{10})$alkyl)aluminum or tri$((C_6-C_{18})$aryl)boron compounds and halogenated (including perhalogenated) derivatives thereof, even more especially tris(fluoro-substituted phenyl)boranes, still even more especially tris(pentafluorophenyl)borane.

Preferred combinations of neutral Lewis acid activating co-catalysts include mixtures comprising a combination of a tri$((C_1-C_4)$alkyl)aluminum and a halogenated tri$((C_6-C_{18})$aryl)boron compound, especially a tris(pentafluorophenyl)borane. Also preferred are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Preferred ratios of numbers of moles of (metal-ligand complex):(tris(pentafluoro-phenylborane):(alumoxane) [e.g., (Group 4 metal-ligand complex):(tris(pentafluoro-phenylborane):(alumoxane)] are from 1:1:1 to 1:10:30, more preferably from 1:1:1.5 to 1:5:10.

Many activating co-catalysts and activating techniques have been previously taught with respect to different metal-ligand complexes in the following U.S. Pat. No. 5,064,802; U.S. Pat. No. 5,153,157; U.S. Pat. No. 5,296,433; U.S. Pat. No. 5,321,106; U.S. Pat. No. 5,350,723; U.S. Pat. No. 5,425,872; U.S. Pat. No. 5,625,087; U.S. Pat. No. 5,721,185; U.S. Pat. No. 5,783,512; U.S. Pat. No. 5,883,204; U.S. Pat. No. 5,919,983; U.S. Pat. No. 6,696,379; and U.S. Pat. No. 7,163,907. Examples of suitable hydrocarbyloxides are disclosed in U.S. Pat. No. 5,296,433. Examples of suitable Bronsted acid salts for addition to polymerization catalysts are disclosed in U.S. Pat. No. 5,064,802; U.S. Pat. No. 5,919,983; U.S. Pat. No. 5,783,512. Examples of suitable salts of a cationic oxidizing agent and a non-coordinating, compatible anion as activating co-catalysts for addition polymerization catalysts are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts as activating co-catalysts for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155 B1 beginning at column 50, at line 39, and going through column 56, at line 55, only the portion of which is incorporated by reference herein.

In some embodiments, one or more of the foregoing activating co-catalysts are used in combination with each other. An especially preferred combination is a mixture of a tri$((C_1-C_4)$hydrocarbyl)aluminum, tri$((C_1-C_4)$hydrocarbyl)borane, or an ammonium borate with an oligomeric or polymeric alumoxane compound.

The ratio of total number of moles of one or more metal-ligand complexes of formula (I) to total number of moles of one or more activating co-catalyst is from 1:10,000 to 100:1. Preferably, the ratio is at least 1:5000, more preferably at least 1:1000; and 10:1 or less, more preferably 1:1 or less. When an alumoxane alone is used as an activating co-catalyst, preferably the number of moles of the alumoxane that are employed is at least 100 times the number of moles of the metal-ligand complex of formula (I). When tris(pentafluorophenyl)borane alone is used as an activating co-catalyst, preferably the number of moles of the tris(pentafluorophenyl)borane that are employed to the total number of moles of one or more metal-ligand complexes of formula (I) form 0.5:1 to 10:1, more preferably from 1:1 to 6:1, still more preferably from 1:1 to 5:1. The remaining activating co-catalysts are generally employed in approximately mole quantities equal to the total mole quantities of one or more metal-ligand complexes of formula (I).

The metal-ligand complex of formula (I) may exist as an isolated crystal(s), optionally being in substantially pure form (i.e., greater than 90%), or as a mixture with one or more other metal-ligand complexes of formula (I); in the form of a solvated adduct, optionally in a solvent, especially an organic liquid, preferably an aprotic solvent; in the form of a dimer; or in the form of a chelated derivative thereof, wherein the chelated derivative comprises the metal-ligand complex of formula (I) and a chelating agent. Preferably, the chelating agent is an organic Lewis base (e.g., an aprotic organic solvent such as tetrahydrofuran (THF) or an aprotic amine base such as triethylamine).

In some embodiments, a reducing agent is also employed so as to produce lower oxidation state forms (e.g., +2) of the metal-ligand complexes of formula (I) from higher oxidation state forms (e.g., +4) of the metal-ligand complexes of formula (I). As used herein, the term "reducing agent" means a metal-containing substance or compound, organic reductant, or technique (e.g., electrolysis) which, under reducing conditions, causes the metal, $M^1$, to be reduced from a higher to a lower oxidation state (e.g., from a +6 formal oxidation state to a +4 formal oxidation state). Examples of suitable reducing agents are alkali metals, alkaline earth metals, aluminum and zinc, and alloys of alkali metals or alkaline earth metals such as sodium/mercury amalgam and sodium/potassium alloy. Examples of other suitable reducing agents are sodium naphthalenide, potassium graphite, lithium alkyls, lithium or potassium alkadienyls, and Grignard reagents (e.g., alkyl magnesium halides). Most preferred reducing agents are the alkali metals or alkaline earth metals, especially lithium and magnesium metal. Suitable techniques that may be adapted by an ordinarily skilled artisan for preparing the metal-ligand complexes of the present invention are known and preferably are derived from techniques taught, for example, in U.S. Pat. No. 5,866,704; U.S. Pat. No. 5,959,047; and U.S. Pat. No. 6,268,444.

Preferably, the metal-ligand complex of formula (I) is collected in an isolated form, which means being substantially solvent-free, for example, contains 10 percent by weight or less of a total of any solvent(s) used in a preparation thereof and the metal-ligand complex of formula (I) being at least 70% by weight of the isolated form. Still more preferably, the metal-ligand complex of formula (I) is collected and purified in an isolated and purified form (i.e., the metal-ligand complex of formula (I) being substantially solvent-free and comprising at least 80% by weight, more preferably at least 90% by weight, of the purified form. As used herein, percent by weight is based on the total weight of a form or mixture. Preferably, the weight percent of the metal-ligand complex of formula (I) in such mixtures is determined using 13-carbon or proton nuclear magnetic resonance ($^{13}$C- or $^1$H-NMR, respectively) spectroscopy.

In some more preferred embodiments of the metal-ligand complex of formula (I), $M^1$ is tetravalent titanium. In other embodiments, $M^1$ is tetravalent zirconium. In still other embodiments, $M^1$ is tetravalent hafnium.

In some embodiments, each X is absent (i.e., n is 0) from the metal-ligand complex of formula (I). In some embodiments n is 1. In some embodiments n is 2. In some embodiments n is 3.

In some embodiments, n is 1, 2, or 3 and at least one X is the neutral Lewis base group that is $R^XNR^KR^L$, $R^KOR^L$, $R^KSR^L$, or $R^XPR^KR^L$. When X is the neutral Lewis acid group, more preferably each $R^X$, $R^K$, and $R^L$ independently is hydrogen, $(C_1$-$C_{40})$hydrocarbyl, $[(C_1$-$C_{10})$hydrocarbyl$]_3$Si, $[(C_1$-$C_{10})$hydrocarbyl$]_3$Si$(C_1$-$C_{10})$hydrocarbyl, or $(C_1$-$C_{40})$heterohydrocarbyl. Still more preferably each $R^X$, $R^K$, and $R^L$ independently is unsubstituted $(C_1$-$C_{20})$hydrocarbyl, and even more preferably unsubstituted $(C_1$-$C_{10})$hydrocarbyl.

In some embodiments, at least one L is present. In such embodiments where two L are present (i.e., L and $L^Q$), preferably each L is the same. In other such embodiments, one L is different. In some embodiments, each L is a halogen atom, unsubstituted $(C_1$-$C_{20})$hydrocarbyl, unsubstituted $(C_1$-$C_{20})$hydrocarbylC(O)O—, or $R^KR^LN$— wherein each of $R^K$ and $R^L$ independently is an unsubstituted $(C_1$-$C_{20})$hydrocarbyl. In some embodiments each L is a chlorine atom, $(C_1$-$C_{10})$hydrocarbyl (e.g., $(C_1$-$C_6)$alkyl or benzyl), unsubstituted $(C_1$-$C_{10})$hydrocarbylC(O)O—, or $R^KR^LN$— wherein each of $R^K$ and $R^L$ independently is an unsubstituted $(C_1$-$C_{10})$hydrocarbyl.

In some embodiments, $R^4$ is as defined previously and $R^2$ and $R^3$ are taken together to form the diradical of formula ($R^{23}$):

That is the metal-ligand complex of formula (I) is a metal-ligand complex of formula (II):

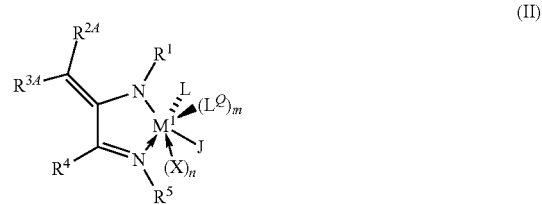

wherein $R^1$, $R^{2A}$, $R^{3A}$, $R^4$, $R^5$, $M^1$, m, n, L, $L^Q$, J, and X are as defined for formula (I). Preferably, each of $R^{2A}$, $R^{3A}$, and $R^4$ independently is H or $(C_1$-$C_{20})$hydrocarbyl, more preferably, H or $(C_1$-$C_{10})$alkyl, still more preferably $(C_1$-$C_{10})$alkyl, and even more preferably, methyl. Also preferably, $R^{2A}$ and $R^{3A}$ are taken together to form a $(C_2$-$C_{20})$hydrocarbylene or $(C_1$-$C_{20})$heterohydrocarbylene. Also more preferably, $R^5$ is $(C_1$-$C_{20})$alkyl (e.g., 1-octyl). Also more preferably, $R^4$ and $R^5$ are taken together to form a $(C_1$-$C_5)$alkylene, still more preferably $(C_3$ or $C_4)$alkylene, even more preferably $CH_2CH_2CH_2$ or $CH_2CH_2CH_2CH_2$.

A more preferred metal-ligand complex of formula (II) is a metal-ligand complex of formula (II-A):

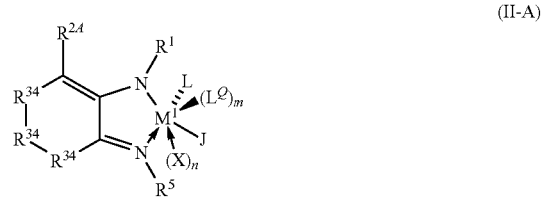

wherein each $R^{34}$ independently is $C(R^{35})_2$, O, S, S(O), S(O)$_2$, N($R^N$), Si($R^C$)$_2$, or P($R^P$), wherein each $R^{35}$ independently is H or $(C_1$-$C_{20})$hydrocarbyl, and each $R^N$, $R^C$, and $R^P$ independently is $(C_1$-$C_{20})$hydrocarbyl, and $M^1$, m, n, L, $L^Q$, J, X, $R^1$, $R^{2A}$ and $R^5$ are as defined for the metal-ligand complex of formula (I). Still more preferred, each $R^{34}$ is $CH_2$. Also still more preferred, the inner of the three $R^{34}$ is O or $N(R^N)$ and the outer $R^{34}$ are each $CH_2$ (i.e., $=C(R^{2A})-R^{34}-R^{34}-R^{34}-$ is $=C(R^{2A})-CH_2-O-CH_2-$ or $=C(R^{2A})-CH_2-N(R^N)-CH_2-$). Also preferred is the metal-ligand complex of formula (II-A), wherein n is 0 and X is absent. Also preferred is the metal-ligand complex of formula (II-A), wherein $R^5$ is taken together with an $R^K$ of X to form a $(C_1-C_{20})$hydrocarbylene. Also preferred is the metal-ligand complex of formula (II-A), wherein $R^1$ or $R^5$ is taken together with an $R^L$ of L to form a $(C_1-C_{20})$hydrocarbylene. Also preferred is the metal-ligand complex of formula (II-A), wherein $R^1$ or $R^5$ and L are taken together to form a diradical moiety $(C_1-C_{40})$hydrocarbylene-$C(O)N((C_1-C_{20})$hydrocarbyl), $(C_1-C_{40})$hydrocarbylene-$C(O)O-$, $(C_1-C_{40})$hydrocarbylene, or $(C_1-C_{40})$heterohydrocarbylene, more preferably $R^1$ and L are said taken together, still more preferably $R^5$ and L are said taken together.

Another more preferred metal-ligand complex of formula (II) is a metal-ligand complex of formula (II-B):

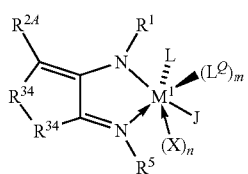

(II-B)

wherein each $R^{34}$ independently is as defined above for $R^{34}$ of formula (II-A) and $M^1$, m, n, L, $L^Q$, J, X, $R^1$, $R^{2A}$ and $R^5$ are as defined for the metal-ligand complex of formula (I). Still more preferred, the topmost of the two $R^{34}$ is O or $N(R^N)$ and the bottommost $R^{34}$ is $CH_2$ (i.e., $=C(R^{2A})-R^{34}-R^{34}-$ is $=C(R^{2A})-O-CH_2-$ or $=C(R^{2A})-N(R^N)-CH_2-$). Still more preferred each $R^{34}$ is $CH_2$. Also preferred is the metal-ligand complex of formula (II-B), wherein n is 0 and X is absent. Also preferred is the metal-ligand complex of formula (II-B), wherein $R^5$ is taken together with an $R^K$ of X to form a $(C_1-C_{20})$hydrocarbylene. Also preferred is the metal-ligand complex of formula (II-B), wherein $R^1$ or $R^5$ is taken together with an $R^L$ of L to form a $(C_1-C_{20})$hydrocarbylene. Also preferred is the metal-ligand complex of formula (II-B), wherein $R^1$ or $R^5$ and L are taken together to form a diradical moiety $(C_1-C_{40})$hydrocarbylene-$C(O)N((C_1-C_{20})$hydrocarbyl), $(C_1-C_{40})$hydrocarbylene-$C(O)O-$, $(C_1-C_{40})$hydrocarbylene, or $(C_1-C_{40})$heterohydrocarbylene, more preferably $R^1$ and L are said taken together, still more preferably $R^5$ and L are said taken together.

Another more preferred metal-ligand complex of formula (II) is a metal-ligand complex of formula (II-C):

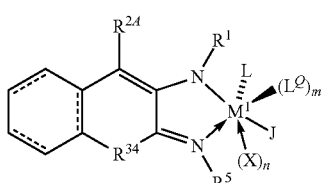

(II-C)

wherein each ---- is absent or is a pi-bond and each $R^{34}$ independently is as defined above for $R^{34}$ of formula (I-A) and $M^1$, m, n, L, $L^Q$, J, X, $R^1$, $R^{2A}$ and $R^5$ are as defined for the metal-ligand complex of formula (I). Still more preferred, each ---- is absent and $R^{34}$ is $CH_2$.

Another more preferred metal-ligand complex of formula (II) is a metal-ligand complex of formula (II-D):

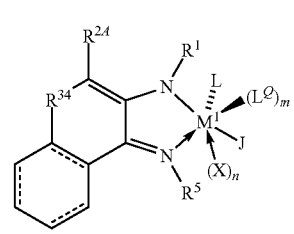

(II-D)

wherein each ---- is absent or is a pi-bond and $R^{34}$ is absent or independently is as defined above for $R^{34}$ of formula (II-A) and $M^1$, m, n, L, $L^Q$, J, X, $R^1$, $R^{2A}$ and $R^5$ are as defined for the metal-ligand complex of formula (I). Still more preferred each ---- is a pi-bond and $R^{34}$ is O or $N(R^N)$. Also still more preferred, each ---- is absent and $R^{34}$ is $CH_2$ or is absent.

Another more preferred metal-ligand complex of formula (II) is a metal-ligand complex of formula (II-E):

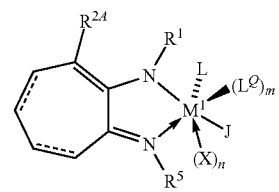

(II-E)

wherein each ---- is a pi-bond or is absent and $M^1$, m, n, L, $L^Q$, J, X, $R^1$, $R^{2A}$ and $R^5$ are as defined for the metal-ligand complex of formula (I). In some embodiments, each ---- is a pi-bond, in others each ---- is absent.

Another more preferred metal-ligand complex of formula (II) is a metal-ligand complex of formula (II-F):

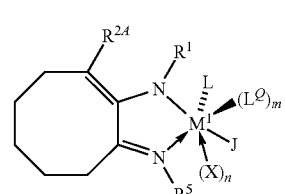

(II-F)

wherein $M^1$, m, n, L, $L^Q$, J, X, $R^1$, $R^{2A}$ and $R^5$ are as defined for the metal-ligand complex of formula (I).

In some embodiments, preferred is the metal-ligand complex of formula (II) wherein $R^{3A}$, $R^4$, and $R^5$ independently are taken together to form a trivalent analog of $(C_1-C_{40})$hydrocarbylene or $(C_1-C_{40})$heterohydrocarbylene; and $M^1$, L, J, n, X, $R^1$, and $R^{2A}$ are as defined for the metal-ligand complex of formula (II). A still more preferred metal-ligand complex of formula (II) is a metal-ligand complex of formula (II-G):

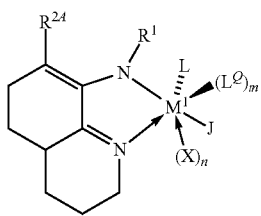
(II-G)

wherein $M^1$, m, n, L, $L^Q$, J, X, $R^1$, and $R^{2A}$ are as defined for the metal-ligand complex of formula (I).

In some embodiments, preferred is the metal-ligand complex of formula (II) wherein $R^{2A}$ and $R^{3A}$ are each H or $(C_1-C_{40})$hydrocarbyl, preferably H or $(C_1-C_3)$hydrocarbyl; and $M^1$, L, J, n, X, $R^1$, $R^4$, and $R^5$ are as defined for the metal-ligand complex of formula (I). A still more preferred metal-ligand complex of formula (II) is a metal-ligand complex of formula (II-H):

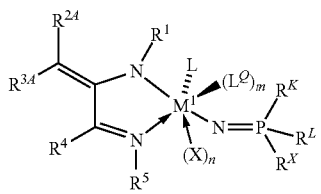
(II-H)

wherein $R^{2A}$ is H or $(C_1-C_{40})$hydrocarbyl (and more preferably, H or $(C_1-C_{10})$hydrocarbyl, and still more preferably, H), $R^{3A}$ and $R^4$ are taken together to form a $(C_1-C_{20})$hydrocarbylene (and more preferably, a $(C_1-C_5)$hydrocarbylene) or $(C_1-C_{20})$heterohydrocarbylene (and more preferably, a $(C_1-C_4)$heterohydrocarbylene), and $M^1$, m, n, L, $L^Q$, X, $R^1$, and $R^5$ are as defined for the metal-ligand complex of formula (I).

In some embodiments, preferred is the metal-ligand complex of formula (II) wherein $R^{2A}$ and $R^{3A}$ are each H or $(C_1-C_{40})$hydrocarbyl, preferably H or $(C_1-C_3)$hydrocarbyl; and $M^1$, L, J, n, X, $R^1$, $R^4$, and $R^5$ are as defined for the metal-ligand complex of formula (I). A still more preferred metal-ligand complex of formula (II) J is $R^KR^LC=N-$ ($J^5$) that is a metal-ligand complex of formula (II-I):

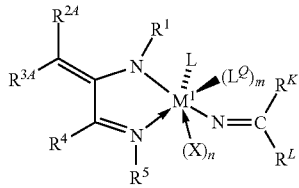
(II-I)

wherein $R^{2A}$ is H or $(C_1-C_{40})$hydrocarbyl (and more preferably, H or $(C_1-C_{10})$hydrocarbyl, and still more preferably, H), $R^{3A}$ and $R^4$ are taken together to form a $(C_1-C_{20})$hydrocarbylene (and more preferably, a $(C_1-C_5)$hydrocarbylene) or $(C_1-C_{20})$heterohydrocarbylene (and more preferably, a $(C_1-C_4)$heterohydrocarbylene), and $M^1$, m, n, L, $L^Q$, X, $R^1$, $R^5$, $R^K$, and $R^L$ are as defined for the metal-ligand complex of formula (I). More preferred is the metal-ligand complex of formula (II-I) wherein $R^{3A}$ and $R^4$ are taken together to form a $(C_2-C_4)$hydrocarbylene and $R^K$ and $R^L$ of J are taken together to form a $(C_1-C_3)$heterohydrocarbylene (e.g., a N,N'-disubstituted-N,N'-diradical of zusammen (Z)-ethene-1,2-diamine such as (substituted $(C_6)$aryl)-N(.)—C(H)=C(H)—N(.)-(substituted $(C_6)$aryl)).

Still more preferred is the metal-ligand complex of formula (II-A) of any one of formulas (II-A1), (II-A2), (II-A3), (II-A4), and (II-A5); of formula (II-B) of any one of formulas (II-B1), (II-B2), (II-B3), (II-B4), (II-B5), (II-B6), (II-B7), and (II-B8); of formula (II-C) of any one of formulas (II-C1), (II-C2), and (II-C3); or of formula (II-D) of any one of formulas (II-D1) and (II-D2):

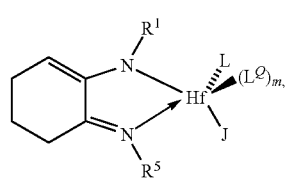
(II-A1)

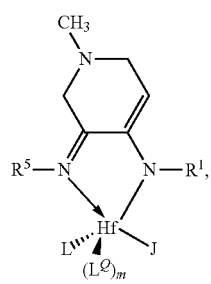
(II-A2)

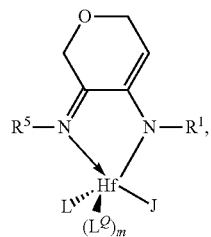
(II-A3)

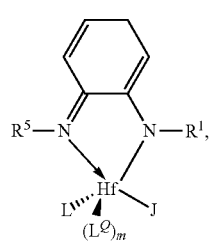
(II-A4)

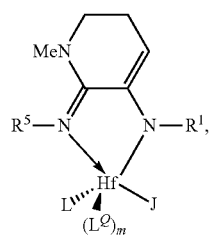
(II-A5)

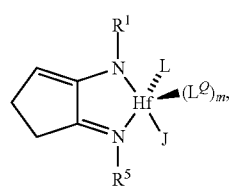
(II-B1)
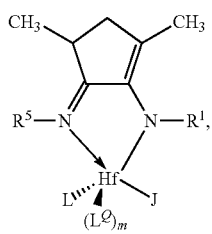
(II-B2)
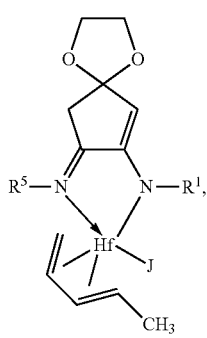
(II-B3)
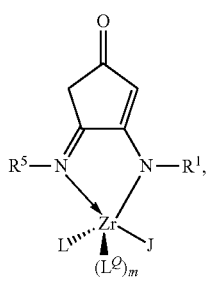
(II-B4)
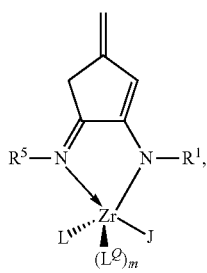
(II-B5)
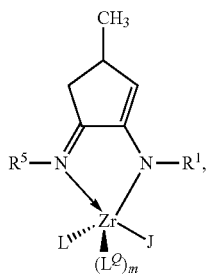
(II-B6)
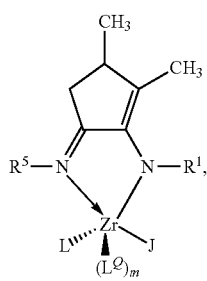
(II-B7)
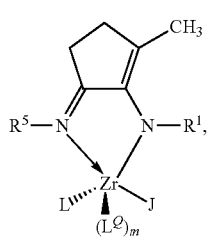
(II-B8)
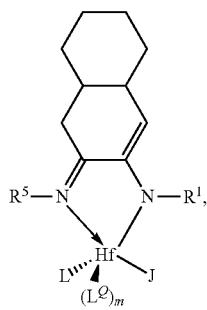
(II-C1)
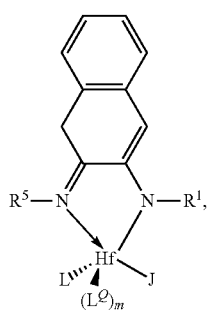
(II-C2)
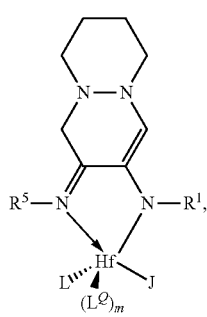
(II-C3)

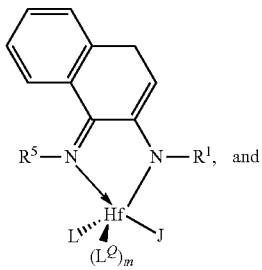

(II-D1)

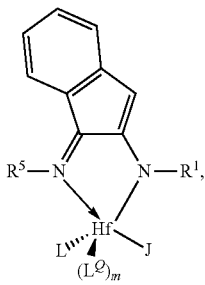

(II-D2)

Wherein n is 0 and X is absent; and J, $R^1$, and $R^5$ are as defined for the metal-ligand complex of formula (II).

In some embodiments, the metal-ligand complex of formula (I) is a metal-ligand complex of formula (III):

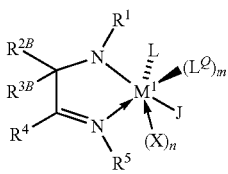

(III)

wherein each of $R^{2B}$, $R^{3B}$, and $R^4$ independently is $(C_1-C_{40})$hydrocarbyl, $(C_1-C_{40})$hydrocarbylO—, $(C_1-C_{40})$hydrocarbylS—, $(C_1-C_{40})$hydrocarbylS(O)—, $(C_1-C_{40})$hydrocarbylS $(O)_2$—, $((C_1-C_{40})$hydrocarbyl$)_2$N—, $((C_1-C_{40})$hydrocarbyl$)_2$ P—, or $(C_1-C_{40})$heterohydrocarbyl, and $R^1$, $R^5$, $M^1$, m, n, L, $L^Q$, J, and X are as defined for formula (I).

In some embodiments, the metal-ligand complex of formula (III) is wherein J is $R^K R^L C=N-$ ($J^5$), that is the metal-ligand complex of formula (III-A):

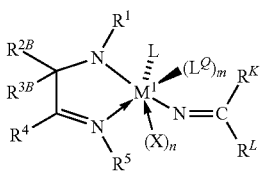

(III-A)

wherein $R^{2B}$, $R^{3B}$, and $R^4$ are as defined for the metal-ligand complex of formula (III); and $M^1$, L, $L^Q$, n, m, X, $R^1$, and $R^5$ are as defined for the metal-ligand complex of formula (I). More preferred is the metal-ligand complex of formula (III-A) wherein $R^K$ and $R^L$ of J are taken together to form a $(C_1-C_3)$heterohydrocarbylene (e.g., a N,N'-disubstituted-N,N'-diradical of zusammen (Z)-ethene-1,2-diamine such as (substituted $(C_6)$aryl)-N(.)—C(H)=C(H)—N(.)-(substituted $(C_6)$aryl)).

In some of the above embodiments of the metal-ligand complex of any one of the aforementioned formulas, J is $R^K R^L R^X P=N-$ ($J^1$), wherein each of $R^K$, $R^L$, and $R^X$ independently is as defined for formula (I). More preferably, $J^1$ is tris(1,1-dimethylethyfiphosphineimido; triphenylphosphineimido; or trimethylphosphineimido.

In some of the above embodiments of the metal-ligand complex of any one of the formulas (I) to (III), J is $R^K R^L B—O—$ ($J^2$), wherein each of $R^K$ and $R^L$ independently is as defined above. More preferably, $J^2$ is bis(1,1-dimethylethyl)boranyl-oxide; diphenylboranyl-oxide; or dimethylboranyl-oxide (i.e., $(CH_3)_2B—O$).

In some of the above embodiments of the metal-ligand complex of any one of the formulas (I) to (III), J is of formula ($J^3$):

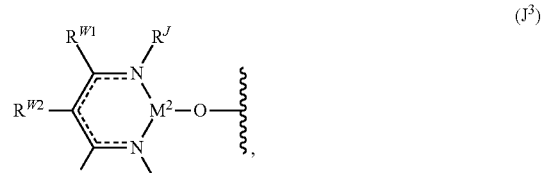

($J^3$)

wherein --- indicates two delocalized pi bonds; each $R^{W1}$ and $R^{W2}$ independently is $R^X$; $M^2$ is Al—$R^A$, Ga—$R^A$, or Zn, wherein each $R^A$ independently is $(C_1-C_{40})$alkyl, $R^K R^L N—$, or $R^L O—$; and each $R^J$ independently is a $(C_6-C_{12})$aryl. Preferably in formula ($J^3$), each $R^{W1}$ is methyl and $R^{W2}$ is hydrogen; $M^2$ is Al—$CH_3$, Ga—$CH_3$, or Zn, more preferably Al—$CH_3$ or Zn; and each $R^J$ is a substituted phenyl, more preferably 2,6-bis(1-methylethyl)phenyl. The ($J^3$) ligands can be prepared by adapting the procedures described in US 2008/0261804 A1, in paragraphs [0029], [0043], and [0044] and FIGS. 1 and 2a.

In some of the above embodiments of metal-ligand complex of any one of the formulas (I) to (III), J is $R^K R^L N—O—$ ($J^4$), wherein each of $R^K$ and $R^L$ independently is as defined above. More preferably, $R^K R^L N—O—$ is 2,2,6,6-tetramethylpiperidinyl-1-oxide.

In some of the above embodiments of the metal-ligand complex of any one of the aforementioned formulas, J is $R^K R^L C=N—$ ($J^5$). More preferably, $J^5$ is 1,3-bis(($C_6-C_{10}$)aryl)-1,3-diaza-2-imino ligand, each $(C_6-C_{10})$aryl independently being unsubstituted or substituted with from 1 to 4 $R^S$.

In some of the above embodiments of the metal-ligand complex of any one of the aforementioned formulas, J is $R^K(R^L R^X N)C=N—$ ($J^6$).

In some of the above embodiments of the metal-ligand complex of any one of the aforementioned formulas, J is $(R^L R^X N)_2 C=N—$ ($J^7$).

In any one of formulas ($J^1$) to ($J^7$), preferably $R^K$, and each of $R^L$, $R^X$, and $R^J$ when present, independently is $(C_1-C_{10})$alkyl, $(C_3-C_{10})$cycloalkyl, or $(C_6-C_{10})$aryl; more preferably $(C_1-C_{10})$alkyl or $(C_6)$aryl, and still more preferably $(C_1-C_4)$alkyl.

In some of the above embodiments of metal-ligand complex of formula (I), n is 1 and X and J are taken together to form the monoanionic bidentate moiety $X^J$-$J^X$ of any one of the aforementioned formulas ($K^1$) to ($K^6$), such a metal-ligand complex being of formula (IV):

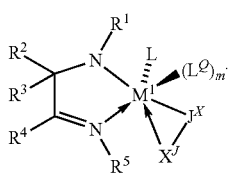

(IV)

In some embodiments, preferred is the metal-ligand complex being of formula (IV) wherein $R^4$ is as defined previously and $R^2$ and $R^3$ are taken together to form the diradical of formula $(R^{23})$:

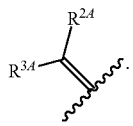

$(R^{23})$

That is the metal-ligand complex of formula (IV) is a metal-ligand complex of formula (IV-A):

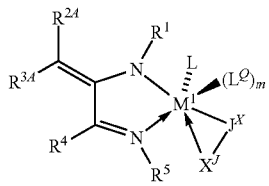

(IV-A)

wherein $R^1$, $R^{2A}$, $R^{3A}$, $R^4$, $R^5$, $M^1$, m, L, $L^Q$, and $X^J$-$J^X$ are as defined for formula (IV).

In some embodiments, the metal-ligand complex of formula (IV) is a metal-ligand complex of formula (IV-B):

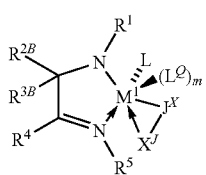

(IV-B)

wherein each of $R^{2B}$, $R^{3B}$, and $R^4$ independently is $(C_1-C_{40})$hydrocarbyl, $(C_1-C_{40})$hydrocarbylO—, $(C_1-C_{40})$hydrocarbylS—, $(C_1-C_{40})$hydrocarbylS(O)—, $(C_1-C_{40})$hydrocarbylS$(O)_2$—, $((C_1-C_{40})$hydrocarbyl$)_2$N—, $((C_1-C_{40})$hydrocarbyl$)_2$P—, or $(C_1-C_{40})$heterohydrocarbyl, and $R^1$, $R^5$, $M^1$, m, L, $L^Q$, and $X^J$-$J^X$ are as defined for formula (IV).

In some embodiments of the metal-ligand complex of formula (IV), (IV-A), or (IV-B), $X^J$-$J^X$ is of the aforementioned formula $(K^1)$. The moiety of formula $(K^1)$ can exist in equilibrium with its tautomer of formula $(K^{1a})$:

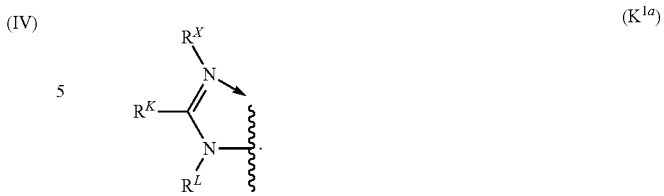

$(K^{1a})$

The tautomers $(K^1)$ and $(K^{1a})$ can also be drawn where the pi electrons in the carbon-nitrogen double bond are delocalized (structure not shown).

In some embodiments of the metal-ligand complex of formula (IV), (IV-A), or (IV-B), $X^J$-$J^X$ is of the aforementioned formula $(K^2)$. The moiety of formula $(K^2)$ can exist in equilibrium with its tautomer of formula $(K^{2a})$:

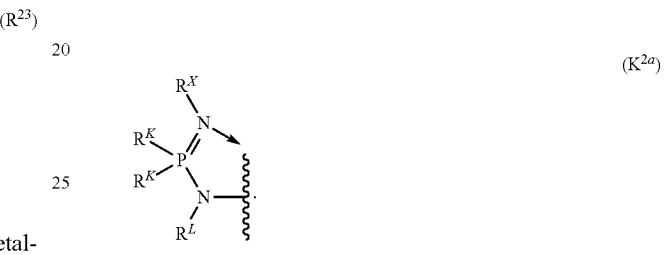

$(K^{2a})$

The tautomers $(K^2)$ and $(K^{2a})$ can also be drawn where the pi electrons in the phosphorous-nitrogen double bond are delocalized (structure not shown).

In some embodiments of the metal-ligand complex of formula (IV), (IV-A), or (IV-B), $X^J$-$J^X$ is of the aforementioned formula $(K^3)$.

In some embodiments of the metal-ligand complex of formula (IV), (IV-A), or (IV-B), $X^J$-$J^X$ is of the aforementioned formula $(K^4)$.

In some embodiments of the metal-ligand complex of formula (IV), (IV-A), or (IV-B), $X^J$-$J^X$ is of the aforementioned formula $(K^5)$.

In some embodiments of the metal-ligand complex of formula (IV), (IV-A), or (IV-B), $X^J$-$J^X$ is of the aforementioned formula $(K^6)$.

In the $X^J$-$J^X$ of any one of formulas $(K^1)$ to $(K^6)$, preferably $R^K$, and each of $R^L$ and $R^X$ when present, independently is $(C_1-C_{10})$alkyl or $(C_4-C_{10})$cycloalkyl, more preferably $(C_1-C_{10})$alkyl, and still more preferably $(C_1-C_4)$alkyl.

More preferred is the metal-ligand complex of any one of the aforementioned formulas having L, wherein each of L (e.g., $L^Q$) independently is $(C_1-C_5)$alkyl, trimethylsilylmethyl, or benzyl; or L is $(C_1-C_5)$alkyl, trimethylsilylmethyl, or benzyl.

More preferred is the metal-ligand complex of any one of the aforementioned formulas having $R^{34}$, wherein each $R^{34}$ independently is $C(R^{35})_2$ and each $R^{35}$ is H or methyl. Also more preferred is the metal-ligand complex of formula (I), wherein one $R^{34}$ is O or $N(R^N)$ and the remaining $R^{34}$, if any, independently are $C(R^{35})_2$ and each $R^{35}$ is H or methyl.

In the above embodiments of the metal-ligand complex of any one of the aforementioned formulas, more preferably at least one $(C_1-C_{40})$heterohydrocarbyl is 2-[$((C_1-C_5)$alkyl$)_2$NCH$_2$]—$(C_6-C_{18})$aryl, still more preferably 2-[$((C_1-C_5)$alkyl$)_2$NCH$_2$]-phenyl; at least one $(C_1-C_{40})$heterohydrocarbylene is

still more preferably

or at least one $(C_1-C_{40})$hydrocarbylene is 2-methylphenyl.

In some embodiments, preferred is the metal-ligand complex of any one of formulas (I), (II) to (II-H), (III), and (IV) to (IV-B), wherein $R^{3A}$ and $R^4$ or $R^{3B}$ and $R^4$, respectively, are taken together to form a $(C_1-C_{40})$hydrocarbylene or $(C_1-C_{40})$heterohydrocarbylene. More preferably, $R^{3A}$ and $R^4$ or $R^{3B}$ and $R^4$, respectively, are taken together to form a $(C_2-C_5)$hydrocarbylene or $(C_1-C_4)$heterohydrocarbylene, still more preferably $(C_2-C_5)$hydrocarbylene, and preferably each of $R^1$ and $R^5$ independently is $(C_1-C_{10})$hydrocarbyl, more preferably $(C_1-C_{10})$alkyl, $(C_3-C_{10})$cycloalkyl, or $(C_6-C_{10})$aryl, and still more preferably $(C_1-C_{10})$alkyl or $(C_6)$aryl. In such embodiments, preferably $R^{2A}$ or $R^{2B}$ is H or $(C_1-C_{10})$alkyl, more preferably H or $CH_3$.

More preferred is the metal-ligand complex of any one of the aforementioned formulas having $R^1$ and $R^5$, wherein each of $R^1$ and $R^5$ independently is $(C_1-C_{10})$hydrocarbyl, more preferably $(C_1-C_{10})$alkyl, $(C_3-C_{10})$cycloalkyl, or $(C_6-C_{10})$aryl, and still more preferably $(C_1-C_{10})$alkyl or $(C_6)$aryl. In such embodiments, preferably, $R^2$ or $R^{2A}$ is H or $(C_1-C_{10})$alkyl, more preferably H or $CH_3$.

Also more preferred is the metal-ligand complex of any one of the aforementioned formulas having $R^1$ wherein $R^1$ is $(C_1-C_{40})$hydrocarbyl, still more preferably $R^1$ is $(C_1-C_{20})$hydrocarbyl, n is 0, and X is absent. Also more preferred is the metal-ligand complex of any one of the aforementioned formulas having $R^1$, wherein $R^1$ is $(C_1-C_{40})$heterohydrocarbyl, still more preferably $R^1$ is $(C_1-C_{20})$heterohydrocarbyl, n is 0, and X is absent. In still other embodiments, n is 1, 2, or 3 and $R^1$ and an $R^K$ of X are taken together to form a $(C_1-C_{40})$hydrocarbylene or $(C_1-C_{40})$heterohydrocarbylene, more preferably $R^1$ and an $R^K$ of X are taken together to form a $(C_1-C_{20})$hydrocarbylene or $(C_1-C_{20})$heterohydrocarbylene. In still other embodiments, $R^1$ and an $R^L$ of L are taken together to form a $(C_1-C_{40})$hydrocarbylene or $(C_1-C_{40})$heterohydrocarbylene, more preferably $R^1$ and an $R^L$ of L are taken together to form a $(C_1-C_{20})$hydrocarbylene or $(C_1-C_{20})$heterohydrocarbylene, n is 0, and X is absent.

Also more preferred is the metal-ligand complex of any one of the aforementioned formulas having $R^5$, wherein $R^5$ is $(C_1-C_{40})$hydrocarbyl, still more preferably $R^5$ is $(C_1-C_{20})$hydrocarbyl, n is 0, and X is absent. Also more preferred is the metal-ligand complex of any one of the aforementioned formulas having $R^5$, wherein $R^5$ is $(C_1-C_{40})$heterohydrocarbyl, still more preferably $R^5$ is $(C_1-C_{20})$heterohydrocarbyl, n is 0, and X is absent. In still other embodiments, n is 1, 2, or 3 and $R^5$ and an $R^K$ of X are taken together to form a $(C_1-C_{40})$hydrocarbylene or $(C_1-C_{40})$heterohydrocarbylene, more preferably $R^5$ and an $R^K$ of X are taken together to form a $(C_1-C_{20})$hydrocarbylene or $(C_1-C_{20})$heterohydrocarbylene. In still other embodiments, $R^5$ and an $R^L$ of L are taken together to form a $(C_1-C_{40})$hydrocarbylene or $(C_1-C_{40})$heterohydrocarbylene, more preferably $R^5$ and an $R^L$ of L are taken together to form a $(C_1-C_{20})$hydrocarbylene or $(C_1-C_{20})$heterohydrocarbylene and optionally n is 0 and X is absent.

Even more preferred, $R^5$ is 1-butyl, 2-propyl, 1,1-dimethylethyl, benzyl, phenyl, cyclohexyl, 1-methyl-piperidin-4-yl, 3-(N,N-dimethylamino)-propyl, 1,1-dimethylethylamino, or pyrrol-1-yl.

Still more preferred is the metal-ligand complex of any one of the aforementioned formulas, wherein $R^1$ and $R^5$ each independently are $(C_1-C_{40})$hydrocarbyl, even more preferably $R^1$ and $R^5$ each independently are $(C_1-C_{20})$hydrocarbyl and optionally n is 0 and X is absent. Also still more preferred is the metal-ligand complex of any one of the aforementioned formulas having X, $R^1$ and $R^5$, wherein one of $R^1$ and $R^5$ is taken together with an $R^K$ of X to form a $(C_1-C_{20})$hydrocarbylene or $(C_1-C_{20})$heterohydrocarbylene and the other of $R^1$ and $R^5$ is $(C_1-C_{20})$hydrocarbyl or $(C_1-C_{20})$heterohydrocarbyl. Also still more preferred is the metal-ligand complex of any one of the aforementioned formulas having L, $R^1$ and $R^5$, wherein one of $R^1$ and $R^5$ is taken together with an $R^L$ of L to form a $(C_1-C_{20})$hydrocarbylene or $(C_1-C_{20})$heterohydrocarbylene and the other of $R^1$ and $R^5$ is $(C_1-C_{20})$hydrocarbyl or $(C_1-C_{20})$heterohydrocarbyl.

In any one of the metal-ligand complexes of the aforementioned formulas having $R^1$ and $R^5$, especially preferred is such a metal-ligand complex wherein one of $R^1$ and $R^5$ is a first group that is 2,6-bis(di($C_1-C_4$)alkyl-amino)phenyl; 2,6-dinitrophenyl; 2,6-di(($C_1-C_4$)alkyloxy)phenyl; 2-($C_1-C_4$) alkyl-phenyl; 2,6-di($C_1-C_4$)alkyl-phenyl; 3,5-di($C_1-C_4$) alkyl-phenyl; 2,4,6-tri($C_1-C_4$)alkyl-phenyl; biphenyl-2-yl; 2,6-diphenylphenyl; 3,5-diphenylphenyl; 2,4,6-triphenylphenyl; 3,5-bis(2,6-bis[($C_1-C_4$)alkyl]phenyl)phenyl; 2,6-di(1-naphthyl)phenyl; 3,5-di(1-naphthyl)phenyl; cyclohexyl; diphenylmethyl; or trityl; wherein each $(C_1-C_4)$alkyl independently is methyl, ethyl, 1-propyl, 1-methylethyl, 1-butyl, 2-butyl, 2-methylpropyl, or 1,1-dimethylethyl. Also especially preferred is the metal-ligand complex wherein one of $R^1$ and $R^5$ is a second group that is $(C_1-C_{20})$alkyl (e.g., 1-butyl, 2-propyl, 1,1-dimethylethyl, and 1-octyl), benzyl, phenyl, cyclohexyl, 1-methyl-piperidin-4-yl, 3-(N,N-di(($C_1$-$C_4$)alkyl)amino)-propyl, $(C_1-C_4)$alkyl-amino, or pyrrol-1-yl. Even more preferred is the metal-ligand complex wherein one of $R^1$ and $R^5$ is as defined for the first group and the other of $R^1$ and $R^5$ is as defined for the second group.

Even more preferred are the metal-ligand complexes of any one of the aforementioned formulas wherein:

$R^1$ is 2,6-bis(1-methylethyl)phenyl; 2-(1-methylethyl) phenyl; 2,4,6-tris(1,1-dimethylethyl)phenyl; 2-(1,1-dimethylethyl)phenyl; 3,4-bis(1,1-dimethylethyl)phenyl; 2,4,6-triphenylphenyl; biphenyl-2-yl; 3,5-diphenylphenyl; cyclohexyl; diphenylmethyl; triphenylmethyl; 3,5-bis(2,6-dimethylphenyl)phenyl; 2,6-bis(dimethylamino)phenyl; 2,6-dinitrophenyl; 2,6-di(1-methylethoxy)phenyl; 2,6-di(1-naphthyl)phenyl; or 3,5-di(1-naphthyl)phenyl; and $R^5$ is 1-butyl; 2-propyl; 1,1-dimethylethyl; benzyl; phenyl; cyclohexyl, 1-methyl-piperidine-4-yl; 3-(N,N-dimethylamino)-propyl; 1,1-dimethylethylamino; or pyrrol-1-yl.

Also even more preferred are the metal-ligand complexes of any one of the aforementioned formulas wherein:

$R^1$ is 2,6-bis(1-methylethyl)phenyl; 2-(1-methylethyl) phenyl; 2,4,6-tris(1,1-dimethylethyl)phenyl; 2-(1,1-dimethylethyl)phenyl; 3,4-bis(1,1-dimethylethyl)phenyl; 2,4,6-triphenylphenyl; biphenyl-2-yl; 3,5-diphenylphenyl; cyclohexyl; diphenylmethyl; triphenylmethyl; 3,5-bis(2,6-dimethylphenyl)phenyl; 2,6-bis(dimethylamino)phenyl; 2,6-dinitrophenyl; 2,6-di(1-methylethoxy)phenyl; 2,6-di(1-naphthyl)phenyl; or 3,5-di(1-naphthyl)phenyl; and J is $R^K R^L R^X P=N—$ ($J^1$).

Also even more preferred are the metal-ligand complexes of any one of the aforementioned formulas wherein:

$R^5$ is 1-butyl; 2-propyl; 1,1-dimethylethyl; benzyl; phenyl; cyclohexyl, 1-methyl-piperidine-4-yl; 3-(N,N-dimethylamino)-propyl; 1,1-dimethylethylamino; or pyrrol-1-yl; and J is $R^KR^LR^XP=N-$ ($J^1$).

Also even more preferred are the metal-ligand complexes of any one of the aforementioned formulas wherein:

$R^1$ is 2,6-bis(1-methylethyl)phenyl; 2-(1-methylethyl)phenyl; 2,4,6-tris(1,1-dimethylethyl)phenyl; 2-(1,1-dimethylethyl)phenyl; 3,4-bis(1,1-dimethylethyl)phenyl; 2,4,6-triphenylphenyl; biphenyl-2-yl; 3,5-diphenylphenyl; cyclohexyl; diphenylmethyl; triphenylmethyl; 3,5-bis(2,6-dimethylphenyl)phenyl; 2,6-bis(dimethylamino)phenyl; 2,6-dinitrophenyl; 2,6-di(1-methylethoxy)phenyl; 2,6-di(1-naphthyl)phenyl; or 3,5-di(1-naphthyl)phenyl; and J is $R^KR^LC=N-$ ($J^5$).

Also even more preferred are the metal-ligand complexes of any one of the aforementioned formulas wherein:

$R^5$ is 1-butyl; 2-propyl; 1,1-dimethylethyl; benzyl; phenyl; cyclohexyl, 1-methyl-piperidine-4-yl; 3-(N,N-dimethylamino)-propyl; 1,1-dimethylethylamino; or pyrrol-1-yl; and J is $R^KR^LC=N-$ ($J^5$).

Also still more preferred is the metal-ligand complex of formula (I) of any one of the Examples described later. In some embodiments, the metal-ligand complex of formula (I) is any one of the Metal-ligand Complexes (1) to (4) of respective Examples 1 to 4 described later. In some embodiments, the metal-ligand complex of formula (I) is any one of the Metal-ligand Complexes (5) to (8) of respective Examples 5 to 8 described later.

In some embodiments, the catalyst of the second embodiment comprises, or is prepared from, a preferred metal-ligand complex of formula (I) and a preferred activating co-catalyst, or a reaction product thereof. In other embodiments, the catalyst of the second embodiment comprises, or is prepared from, two or more preferred metal-ligand complexes of formula (I), and at least one preferred activating co-catalyst, or a reaction product thereof.

In some embodiments, the catalyst of the second embodiment further comprises one or more solvents, diluents (described later), or a combination thereof, as described herein. In other embodiments, the catalyst of the second embodiment still further comprises a dispersant, e.g., an elastomer, preferably dissolved in the diluent. In these embodiments, the catalyst of the second embodiment preferably comprises a homogeneous catalyst.

In some embodiments, the catalyst of the second embodiment further comprises, or is further prepared from, an inorganic or organic particulated solid support, wherein the catalyst of the second embodiment is in supporting operative contact with the particulated solid support to give a particulated solid-supported catalyst. In these embodiments, the invention particulated solid-supported catalyst comprises a heterogeneous catalyst.

The particulated solid support is any material that is capable of supporting the catalyst of the second embodiment and allows the resulting invention particulated solid-supported catalyst to catalyze polymerization of a polymerizable olefin. Examples of particulated solids are silica, silica gel, alumina, clays, expanded clays (aerogels), aluminosilicates, trialkylaluminum compounds, and organic or inorganic polymeric materials, especially polyolefins such as, for example, a poly(tetrafluoroethylene). More preferably, the catalyst of the second embodiment and solid support are employed in the invention particulated solid-supported catalyst in amounts that provide a ratio of (weight of the catalyst of the second embodiment (based on metal $M^1$)):weight of the solid support) of from $1:10^6$ to $1:10^3$, more preferably from $1:10^6$ to $1:10^4$.

The term "olefin-polymerizing conditions" means reaction parameters such as, for example, temperature, pressure, concentration of olefin monomer(s), solvent(s), if any, reaction time, and reaction atmosphere sufficient to produce at least 5 mole percent yield of a polyolefin therefrom. In some embodiments, polymerization of olefins is accomplished using known conditions for Ziegler-Natta or Kaminsky-Sinn type olefin polymerization reactions. As the process of the third embodiment occurs under olefin-polymerizing conditions sufficient to polymerize at least some of the at least one polymerizable olefin and produce a polyolefin therefrom. The process can be performed at or with any temperature, pressure, or other condition (e.g., solvent, atmosphere, and absolute and relative amounts of ingredients) at which the polymerization reaction occurs. Preferably the conditions comprise a temperature of from about −100° C. to about 300° C., more preferably at least about 0° C., still more preferably at least about 20° C., even more preferably at least about 50° C.; and more preferably about 250° C. or less, still more preferably about 200° C. or less, still more preferably about 150° C. or less; and a pressure from about 0.5 atmosphere (50 kilopascals (kPa) to 10,000 atmospheres (1,010,000 kPa), more preferably at least about 1 atmosphere (101 kPa), still more preferably at least about 10 atmospheres (1010 kPa); and more preferably 1000 atmospheres (101,000 kPa) or less, still more preferably 500 atmospheres (50,500 kPa) or less; preferably under a substantially inert atmosphere (e.g., a dry (i.e., substantially free from water) atmosphere consisting essentially of nitrogen gas, a noble gas (e.g., argon gas and helium gas), or a mixture of two or more thereof); with mixing (e.g., agitating, stirring, or shaking) for a time sufficient to produce the polyolefin (e.g., as determined by assaying an aliquot of a reaction mixture).

In some embodiments, the metal-ligand complexes of this invention are supported on a solid support as described herein and used in olefin polymerization processes in a slurry or a gas phase polymerization. As a practical limitation, slurry polymerization preferably takes place in liquid diluents in which the polymer product is substantially insoluble (e.g., less than 50 milligrams of polymer product dissolves in 1.0 milliliter of liquid diluent at 25° C.). Preferably, the diluent for slurry polymerization is one or more hydrocarbons, each with less than 5 carbon atoms. In some embodiments, one or more saturated hydrocarbons such as ethane, propane or butane are used in whole or part as the diluent. In other embodiments, an alpha-olefin monomer or a mixture of different alpha-olefin monomers are used in whole or part as the diluent. Most preferably, at least a major part of the diluent comprises the alpha-olefin monomer or monomers to be polymerized. In some embodiments, a dispersant, particularly an elastomer, is dissolved in the diluent, preferably utilizing techniques known in the art.

In some embodiments, suspension, solution, slurry, gas phase, solid state powder polymerization or other process conditions are employed. In other embodiments, a particulated solid support is employed in the form of the invention particulated solid-supported catalyst described previously, preferably when the invention particulated solid-supported catalysts are used in an aspect of the third embodiment comprising a gas phase polymerization process. In most polymerization reactions of the third embodiment, the ratio of (moles of catalyst of the second embodiment):(total moles of polymerizable compounds employed) is from $10^{-12}:1$ to $10^{-1}:1$, more preferably from $10^{-9}:1$ to $10^{-5}:1$.

The catalysts of the second embodiment, whether or not supported on a solid support, preferably are used to polymerize a polymerizable olefin, or co-polymerize two or more polymerizable olefins (i.e., olefin monomers), to prepare a polyolefin. The term "polymerizable olefin" means a carbon-carbon double or triple bond-containing monomer or carbon-carbon double or triple bond-containing oligomer or polyolefin prepared therefrom and independently has from 2 to 100,000 carbon atoms, preferably 50,000 carbon atoms or less, more preferably 10,000 carbon atoms or less. Preferably there is at least one carbon-carbon double bond in the polymerizable olefin, and more preferably the polymerizable olefin is a carbon-carbon double bond-containing monomer. Thus, polymerizable olefins include long chain macromolecular alpha-olefin units that are vinyl terminated polymeric remnants formed in situ during continuous solution polymerization reactions. In some aspects of the third embodiment, such long chain macromolecular alpha-olefin units are readily polymerized along with ethylene and other short chain olefin monomers to give a polyolefin having long chain branching.

In some embodiments, a process of the third embodiment employs one or more of the catalysts of the second embodiment and at least one additional homogeneous or heterogeneous polymerization catalyst, which may be a same or different catalyst of the second embodiment or a prior art olefin polymerization catalyst such as that referenced previously, either in the same reactor or in separate reactors, preferably connected in series or in parallel, to prepare polymer blends having desirable properties. A general description of such a process is disclosed in PCT International Patent Application Publication Number WO 94/00500.

In some embodiments, the polymerization process of the third embodiment is carried out as a batchwise or a continuous polymerization process. A continuous process is preferred, in which continuous process, for example, catalyst of the second embodiment, ethylene, a co-monomer olefin other than ethylene, and optionally a solvent, diluent, dispersant, or combination thereof are essentially continuously supplied to the reaction zone, and resulting polyolefin product is essentially continuously removed therefrom.

Preferably, such polyolefin products are produced in a solution process, most preferably a continuous solution process. Without limiting in any way the scope of the invention, an illustrative means for carrying out such an essentially continuous polymerization process is as follows. In a stirred-tank reactor, the monomer olefins to be polymerized are introduced continuously, together with solvent and an optional chain transfer agent such as, for example, a stream of hydrogen introduced to the reactor. The reactor contains a liquid phase composed substantially of monomers, together with any solvent or additional diluent and dissolved polymer. In other embodiments, a small amount of a "H"-branch-inducing diene such as norbornadiene, 1,7-octadiene, or 1,9-decadiene is also added. Metal-ligand Complex of formula (I) and activating co-catalyst are continuously introduced in the reactor liquid phase. In some embodiments, reactor temperature and pressure are controlled by, for example, adjusting solvent/monomer ratio, adjusting addition rates, cooling or heating the reactor liquid phase (e.g., using coils, jackets or both), or a combination thereof. In some embodiments, rate of polymerization is controlled by adjusting rate of addition of catalyst of the second embodiment. In some embodiments, ethylene content of a polymer product thereof is varied by adjusting the ratio of ethylene to comonomer olefin in the reactor, which ratio preferably is controlled by manipulating the respective feed rates of the monomers to the reactor. In some embodiments, molecular weight of polymer product is controlled by adjusting temperature, adjusting monomer concentration, or with the previously mentioned chain transfer agent. In some embodiments, reactor effluent is contacted with a catalyst kill agent such as water. A resulting polyolefin product solution is optionally heated, and the polyolefin is recovered by devolatilizing, e.g., flashing off volatiles such as gaseous monomers, residual solvent, and diluents at reduced pressure. In some embodiments, further devolatilization is conducted in equipment such as a devolatilizing extruder. In a continuous process, mean residence time of the catalyst of the second embodiment and polyolefin product in the reactor preferably is from about 5 minutes to about 8 hours, and more preferably from about 10 minutes to about 6 hours.

In some embodiments, the catalysts of the second embodiment are employed in the production of ethylene homopolymers and ethylene/alpha-olefin copolymers having high levels of long chain branching. The use of the catalysts of the second embodiment in continuous polymerization processes, especially continuous, solution polymerization processes, allows for elevated reactor temperatures, which favor the formation of vinyl terminated polymer chains. In some embodiments, vinyl terminated polymer chains are incorporated into a growing polymer, thereby giving a polymer comprising a long chain branch. The use of the catalysts of the second embodiment advantageously allows for the economical production of ethylene/alpha-olefin copolymers having processability similar to high pressure, free radical produced low density polyethylene.

Generally the ethylene/alpha-olefin copolymers have densities from 0.85 grams per milliliter (g/mL) to 0.96 g/mL. In some embodiments, a comonomer-to-monomer ratio of moles of alpha-olefin comonomer to moles of ethylene monomer used in the polymerization is varied in order to adjust the density of the resulting ethylene/alpha-olefin copolymer. When producing ethylene/alpha-olefin copolymers with a preferred density range of from 0.91 g/mL to 0.93 g/mL, preferably the comonomer-to-monomer ratio is less than 0.2, more preferably less than 0.05, still more preferably less than 0.02, and even more preferably less than 0.01. In some embodiments, use of hydrogen gas has been found to effectively control the molecular weight of the resulting ethylene/alpha-olefin copolymer. In some embodiments, the ratio of moles of hydrogen gas to moles of monomer is less than about 0.5, preferably less than 0.2, more preferably less than 0.05, still more preferably less than 0.02 and even more preferably less than 0.01.

Preferably, each polymerizable olefin independently is ethylene; a linear or branched alpha-olefin of from about 3 to about 20 carbon atoms such as, for example, propylene, isobutylene, 1-butene, 1-pentene, 1-hexene, 3-methyl-1-pentene, 4-methyl-1-pentene, 1-octene, 1-decene, long chain macromolecular $\alpha$-olefins, and mixtures thereof; an acyclic diene such as, for example, 1,4-butadiene, 1,4-hexadiene, and 1,7-octadiene; a cyclic olefin such as, for example, cyclobutene, cyclopentene, norbornene, and norbornene derivatives that are substituted in the 5- and 6-positions with $(C_1-C_{20})$hydrocarbyl groups; a cyclic diene hydrocarbon of from about 4 to about 40 carbon atoms such as, for example, a cyclohexadiene, ethylidene-norbornene, and norbornadiene; an aromatic ring-substituted olefin of from 8 to 20 carbon atoms (e.g., styrene, $(C_1-C_4)$alkyl-substituted styrenes, and 4-phenylbutene); a vinyl monomer that is, for example, 4-vinylcyclohexene, divinylbenzene, and mixtures thereof with ethylene, an acrylonitrile, maleic acid ester, vinyl acetate, acrylate ester, methacrylate ester, or vinyl trialkyl silane; and mixtures thereof such as mixtures of ethylene and styrene, mixtures of ethylene, propylene, and styrene; mixtures of ethylene, styrene or propylene, and 1,4-hexadiene or a non-conjugated diene, especially ethylidene-norbornene.

In preferred embodiments, the respective metal-ligand complexes of formula (I), catalysts of the second embodiment, including invention solid-supported catalysts, show decreased or no thermally-induced intramolecular alkyl group migration when heated at a preferred operating temperature as described above.

Catalysts of the second embodiment may be made by adapting any relevant process known in the art and the particular process is not critical to the present invention. Preferably, the catalyst of the second embodiment is prepared by a process of the fourth embodiment. More preferably, the process of the fourth embodiment comprises contacting the metal-ligand complex of formula (I) to an activating co-catalyst and a solvent, preferably an aprotic solvent, under conditions sufficient to produce a catalyst of the second embodiment. Preferably, the conditions sufficient to produce the catalyst of the second embodiment include those described above for the process of the third embodiment. Preferably, the catalyst of the second embodiment is prepared in situ. More preferably, the catalyst of the second embodiment is prepared in situ and used in the process of the third embodiment. In some embodiments, the catalyst of the second embodiment is prepared in situ in the presence of at least one polymerizable olefin, and the catalyst of the second embodiment is thereby immediately contacted to the at least one polymerizable olefin in the process of the third embodiment.

In some embodiments, the invention catalyst of the second embodiment is prepared as a homogeneous catalyst by addition of one or more metal-ligand complexes of formula (I) and one or more activating co-catalysts to a solvent or diluent in which the polymerization process of the third embodiment will be conducted.

In other embodiments, the catalyst of the second embodiment is a solid-supported catalyst that is prepared as a heterogeneous catalyst by adsorbing, depositing or chemically attaching one or more metal-ligand complexes of formula (I) and optionally one or more activating co-catalysts on an inorganic or organic particulated solid support to give the invention particulated solid-supported catalyst described herein. In some embodiments, the metal-ligand complex(es) is(are) added to the solid support either subsequently, simultaneously to, or prior to addition of the activating co-catalyst(s) to the solid support. In a preferred embodiment, the invention heterogeneous catalyst is prepared by reacting an inorganic solid support, preferably a tri(($C_1$-$C_4$)alkyl)aluminum compound, with an activating co-catalyst. Preferably, the activating co-catalyst is an ammonium salt of a hydroxyaryl(tris (pentafluorophenyl))borate, more preferably an ammonium salt of either (4-hydroxy-3,5-ditertiarybutylphenyl)tris(pentafluorophenyl)borate or (4-hydroxyphenyl)-tris(pentafluorophenyl)borate. Preferably, the activating co-catalyst is deposited onto the solid support by co-precipitating, imbibing, spraying, or a similar technique, and thereafter any solvent or diluent are preferably removed.

Metal-ligand Complexes of formula (I) may be made by adapting any relevant process known in the art and the particular process is not critical to the present invention. Preferred is the process of the fifth embodiment. In some embodiments of the process of the fifth embodiment, the intermediate metal-ligand complex of formula (Z) is any one of the preferred embodiments thereof shown later in the Preparations.

In some embodiments, the process of the fifth embodiment further comprises a step of preparing the intermediate metal-ligand complex of formula (Z). The intermediate metal-ligand complex of formula (Z) can be prepared by any one of a number of methods such as the preferred methods described below.

In the process of the fifth embodiment, a preferred intermediate metal-ligand complex of formula (Z) is made by contacting a solution of, for example, $M^1$(benzyl)$_4$ or $M^1$(benzyl)Cl$_3$, wherein $M^1$ is as defined for formula (I), in a solvent to a solution of one (e.g., for n=1) or two (e.g., for n=2) mole equivalents of an intermediate compound of formula (Y)

or a salt of a conjugate base thereof, in a solvent (e.g., toluene) under conditions sufficient to produce the preferred intermediate metal-ligand complex of formula (Z), wherein each of $R^1$ to $R^5$ independently is as defined for formula (I). The phrase "salt of a conjugate base of the compound of formula (Y)" means an overall neutral ionic molecule comprised of a monovalent anion (e.g., mono-deprotonated) derivative of the compound of formula (Y) (i.e., [(Y)$^-$]) and an overall monovalent cation. Examples of overall monovalent cations are trityl cation, tetra(($C_1$-$C_{40}$)hydrocarbyl)ammonium), sodium cation, calcium dication in a hemi calcium salt (e.g., $Ca^{+2}$ [(Y)$^-$](counter monoanion)), and magnesium dication in a hemi magnesium salt $Mg^{+2}$ [(Y)$^-$](counter monoanion, wherein the counter monoanion is, for example, a carbanion, halide, bicarbonate ($HCO_3^{-1}$), bisulfate ($HSO_4^{-1}$), or dihydrogen phosphate ($H_2PO_4^{-1}$)). The conditions sufficient to produce the preferred intermediate metal-ligand complex of formula (Z) preferably are those described above for a process of the third embodiment.

In another embodiment of a process of the fifth embodiment, the preferred intermediate metal-ligand complex of formula (Z) is made by first contacting the intermediate compound of formula (Y) to a metal tetrahalide (e.g., $TiCl_4$, $ZrBr_4$, and $HfCl_4$), and then contacting the resulting mixture to, for example, a carbanion of ($C_1$-$C_{20}$)alkyl, (($C_1$-$C_5$)alkyl)$_3$Si($C_1$-$C_5$)alkyl, ($C_3$-$C_{10}$)cycloalkyl, ($C_3$-$C_{10}$)cycloalkyl-($C_1$-$C_3$)alkylene, ($C_6$-$C_{18}$)aryl, or ($C_6$-$C_{18}$)aryl-($C_1$-$C_3$)alkylene in a solvent to prepare the preferred intermediate metal-ligand complex of formula (Z). In still another embodiment of a process of the fifth embodiment, the preferred intermediate metal-ligand complex of formula (Z) is made by first contacting the intermediate compound of formula (Y) to the carbanion in a solvent to give a salt of a conjugate base of the intermediate compound of formula (Y), and then contacting the conjugate base to the metal tetrahalide to prepare the preferred intermediate metal-ligand complex of formula (Z).

In still another alternative embodiment of the process of the fifth embodiment, the preferred intermediate metal-ligand complex of formula (Z) is made by first contacting the intermediate compound of formula (Y) to a carbanion-containing base such as, for example, a ($C_1$-$C_4$)alkyl lithium (e.g., 1-butyl lithium) or ($C_1$-$C_4$)alkyl magnesium halide (e.g., methyl magnesium bromide) in a solvent to prepare respectively a lithium or magnesium halide salt of a conjugate base of the intermediate compound of formula (Y), and then contacting the conjugate base to a trialkylsilyl halide (e.g., trimethylsilyl chloride) to form an intermediate N-trialkylsilyl analog of the intermediate compound of formula (Y). Then, contacting the N-trialkylsilyl analog of the intermediate compound of formula (Y) to a metal tetrahalide, followed by contacting the resulting mixture to, for example, a carbanion of $(C_1-C_{20})$ alkyl, $((C_1-C_5)alkyl)_3Si(C_1-C_5)alkyl$, $(C_3-C_{10})cycloalkyl$, $(C_3-C_{10})cycloalkyl-(C_1-C_3)alkylene$, $(C_6-C_{18})aryl$, or $(C_6-C_{18})aryl-(C_1-C_3)alkylene$ in a solvent prepares the preferred intermediate metal-ligand complex of formula (Z).

Preferably, the process of the fifth embodiment employs one or more aprotic solvents. More preferably, the process employs one or more aprotic solvents and the metal-ligand complex of formula (I) is isolated via an isolating step, more preferably isolated and purified via isolating and purifying step(s), to respectively give the isolated or isolated and purified forms thereof as described previously. In some embodiments, the isolating and purifying steps are essentially simultaneous, i.e., essentially a single step. An example of the isolating step is evaporation of the solvent and other volatile components from the metal-ligand complex. Preferably, the evaporation is done under vacuum, under a substantially inert atmosphere, or both. In other embodiments, the process further comprises the steps of isolating the metal-ligand complex from the solvent and purifying the isolated metal-ligand complex to give a purified metal-ligand complex of at least 70 weight percent (wt %) purity by conventional methods. An example of purifying the metal-ligand complex of formula (I) is evaporating solvent(s) and other volatile components from a reaction mixture containing the metal-ligand complex (i.e., isolating and purifying the metal-ligand complex of formula (I) are simultaneous), triturating an isolated metal-ligand complex of formula (I), precipitating or crystallizing the metal-ligand complex of formula (I) from the reaction mixture or from a purification solvent(s), or a combination thereof. Preferably, trituration of the metal-ligand complex of formula (I) is performed with a solvent in which the metal-ligand complex of formula (I) is only partially soluble or insoluble, and removing the triturate. An example of isolation and purification comprising a single step is filtering a precipitated metal-ligand complex of formula (I) from a reaction mixture, optionally washing the resulting filtercake of a precipitated metal-ligand complex of formula (I) with a solvent, and drying the filtercake, wherein the precipitated metal-ligand complex of formula (I) is at least 70 wt % pure.

In some embodiments, the metal-ligand complex of formula (I) is prepared in situ and used in the process of the fourth embodiment. More preferably, the metal-ligand complex of formula (I) is prepared in situ, followed by contacting the metal-ligand complex of formula (I) to at least one activating co-catalyst and at least one polymerizable olefin, so that, in turn, the catalyst of the second embodiment is prepared in situ by the process of the fourth embodiment, and the catalyst of the second embodiment is thereby immediately contacted to the at least one polymerizable olefin in the process of the third embodiment to yield a polyolefin.

Illustrative procedures for preparing metal-ligand complexes of formula (I) are shown in Scheme 1 as shown in FIG. 1. In FIG. 1, Scheme 1 illustrates preparation of the metal-ligand complex of formula (I) wherein, n is 0, X is absent, J is any one of $(J^1)$ to $(J^7)$, and $M^1$, $R^1$ to $R^5$ and L are as defined for formula (I). Option A of Scheme 1 is preferred for the intermediate compound of formula (Y) wherein $R^2$ and $R^3$ are not replaced by the aforementioned diradical of formula $(R^{23})$. Option D is preferred for the intermediate compound of formula (Y) wherein $R^2$ and $R^3$ are replaced by the diradical of formula $(R^{23})$. Such a metal-ligand complex is shown in Scheme 1 as the formula (I-X), wherein in Scheme 1, m is as defined for formula (I) and is selected such that the metal-ligand complex of formula (I-X) is, in aggregate, neutral. The procedure in Scheme 1 can be adapted, if desired to prepare the metal-ligand complex of formula (I) wherein X is not absent (i.e., n is 1, 2 or 3) or wherein one X and J are taken together to form $X^J$-$J^X$ by contacting X to the compound of formula (I-X) or by replacing the compound of formula J-H with the aforementioned compound of formula $X^J$-$J^X$-H, respectively.

In FIG. 1 Scheme 1, option A, the intermediate compound of formula (Y) (described previously) is deprotonated with a non-nucleophilic base to give an enamide (not shown), which is then allowed to react with a metal halide such as $M^1(Cl)_{m+1}$, wherein m is as defined above for formula (Y), followed by reaction of the resulting metal-ligand complex with a organometallic compound such as, for example, an organolithium (L-Li) or Grignard reagent (L-MgBr) (or organosodium (L-Na) or organopotassium (L-K)), wherein L is as defined for formula (I), to give an intermediate metal-ligand complex of formula (Z-X). Alternatively, in option B, the intermediate compound of formula (Y) reacts with an organometallic compound $M^1(L)_{m+1}$ to give the intermediate metal-ligand complex of formula (Z-X). In yet another alternative, option C, the intermediate compound of formula (Y) reacts with a metal-amido compound $M^1(NR^KR^L)_{m+1}$ to give an intermediate (not shown), which then reacts with the organometallic compound (e.g., organolithium or Grignard reagent) to give the intermediate metal-ligand complex of formula (Z-X). In yet another alternative, option D, the intermediate compound of formula (Y) reacts with the metal halide such as $M^1(Cl)_{m+1}$, followed by reaction of the resulting metal-ligand complex with 4 mole equivalents of an organometallic compound L-Li or L-MgBr such as, for example, methyl lithium or methyl magnesium bromide to give the intermediate metal-ligand complex of formula (Z-X), wherein L is a $(C_1-C_{40})$hydrocarbyl. Then, the intermediate metal-ligand complex of formula (Z-X) is reacted with compound of formula J-H to give the intermediate metal-ligand complex of formula (I-X).

The reactions described in FIG. 1 Scheme 1 preferably are carried out under a substantially inert gas atmosphere in an anhydrous aprotic solvent such as, for example, toluene, xylenes, tetrahydrofuran, diethylene glycol dimethyl ether, or a combination thereof and at a temperature in a range of from about −78° C. to about 200° C. Preferably, the reactions are carried out at atmospheric pressure.

Another aspect of the present invention is a polyolefin prepared according to a process of the third embodiment. In some embodiments, polymerizable olefins useful in the invention processes are $(C_2-C_{40})$hydrocarbons consisting of carbon and hydrogen atoms and containing at least 1 and preferably no more than 3, and more preferably no more than 2 carbon-carbon double bonds. In some embodiments, from 1 to 4 hydrogen atoms of the $(C_2-C_{40})$hydrocarbon are replaced, each by a halogen atom, preferably fluoro or chloro to give halogen atom-substituted $(C_2-C_{40})$hydrocarbons. The $(C_2-C_{40})$hydrocarbons (not halogen atom-substituted) are preferred. Preferred polymerizable olefins (i.e., olefin monomers) useful for making the polyolefins are ethylene and polymerizable $(C_3-C_{40})$olefins. The $(C_3-C_{40})$olefins include an alpha-olefin, a cyclic olefin, styrene, and a cyclic or acyclic diene. Preferably, the alpha-olefin comprises the $(C_3-C_{40})$ alpha-olefin, more preferably a branched chain $(C_3-C_{40})$alpha-olefin, still more preferably a linear-chain $(C_3-C_{40})$alpha-olefin, even more preferably a linear chain $(C_3-C_{40})$ alpha-olefin of formula (A): $CH_2=CH_2—(CH_2)_ZCH_3$ (A), wherein z is an integer of from 0 to 40, and yet even more preferably a linear-chain $(C_3-C_{40})$alpha-olefin that is 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, or a linear-chain ($C_{20}$-$C_{24}$)alpha-olefin. Preferably the cyclic olefin is a ($C_3$-$C_{40}$)cyclic olefin. Preferably, the cyclic or acyclic diene is a ($C_4$-$C_{40}$)diene, preferably an acyclic diene, more preferably an acyclic conjugated ($C_4$-$C_{40}$)diene, more preferably an acyclic 1,3-conjugated ($C_4$-$C_{40}$)diene, and still more preferably 1,3-butadiene.

Polyolefins that can be made by an invention process include, for example, polyethylene and interpolymers that comprise residuals of ethylene and one or more polymerizable ($C_3$-$C_{40}$)olefins. Preferred homopolymers are polyethylene, polypropylene, and polybutylene. Preferred interpolymers are those prepared by co-polymerizing a mixture of two or more polymerizable olefins such as, for example, ethylene/propylene, ethylene/1-butene, ethylene/1-pentene, ethylene/1-hexene, ethylene/4-methyl-1-pentene, ethylene/1-octene, ethylene/styrene, ethylene/propylene/butadiene and other EPDM terpolymers. Preferably, the polyolefin is an ethylene homopolymer, an ethylene/alpha-olefin interpolymer (e.g., copolymer), or an ethylene/alpha-olefin/diene interpolymer (e.g., terpolymer).

Preferably, the polyolefin comprises a poly(ethylene alpha-olefin) block copolymer prepared according to an aforementioned preferred process of the third embodiment. The poly(ethylene alpha-olefin) block copolymer comprises an ethylene-derived hard segment (i.e., polyethylene hard segment) and a soft segment comprising residuals from the alpha-olefin and ethylene. The residuals of the alpha-olefin and ethylene typically are approximately randomly distributed in the soft segment.

Preferably, the polyethylene hard segment is characterizable as having less than 5 mole percent (mol %) of a residual of the alpha-olefin covalently incorporated therein, as determined by nuclear magnetic resonance as described later.

Preferably, the poly(ethylene alpha-olefin) block copolymer is characterizable as having a melting temperature of greater than 100 degrees Celsius, and more preferably greater than 120° C., as determined by Differential Scanning Calorimetry using the procedure described later.

The poly(ethylene alpha-olefin) block copolymers comprise ethylene residuals and one or more copolymerizable α-olefin comonomer residuals (i.e., ethylene and one or more copolymerizable α-olefin comonomers in polymerized form). The poly(ethylene alpha-olefin) block copolymers are characterized by multiple blocks or segments of two or more polymerized monomer units differing in chemical or physical properties. That is, the ethylene/α-olefin interpolymers are block interpolymers, preferably multi-block interpolymers or copolymers. The terms "interpolymer" and "copolymer" are used interchangeably herein. In some embodiments, the multi-block copolymer can be represented by the following formula:

(AB)n where n is at least 1, preferably an integer greater than 1, such as 2, 3, 4, 5, 10, 15, 20, 30, 40, 50, 60, 70, 80, 90, 100, or higher, "A" represents a hard block or segment and "B" represents a soft block or segment. Preferably, As and Bs are linked in a linear fashion, not in a branched or a star fashion.

"Hard" segments refer to blocks of polymerized units in which ethylene residuals are present in an amount greater than 95 weight percent, and preferably greater than 98 weight percent in the poly(ethylene alpha-olefin) block copolymers. In other words, the comonomer (i.e., alpha-olefin) residuals content in the hard segments is less than 5 weight percent, and preferably less than 2 weight percent. In some embodiments, the hard segments comprise all or substantially all ethylene residuals. The phrases "polyethylene hard segment" and "ethylene-derived hard segment" are synonymous and mean the hard segment portion of a poly(ethylene alpha-olefin) block copolymer.

"Soft" segments refer to blocks of polymerized units in which the comonomer (i.e., alpha-olefin) residuals content is greater than 5 weight percent, preferably greater than 8 weight percent, greater than 10 weight percent, or greater than 15 weight percent in the poly(ethylene alpha-olefin) block copolymers. In some embodiments, the comonomer residuals content in the soft segments can be greater than 20 weight percent, greater than 25 eight percent, greater than 30 weight percent, greater than 35 weight percent, greater than 40 weight percent, greater than 45 weight percent, greater than 50 weight percent, or greater than 60 weight percent.

In some embodiments, A blocks and B blocks are randomly distributed along a polymer (backbone) chain of the poly (ethylene alpha-olefin) block copolymer. In other words, the poly(ethylene alpha-olefin) block copolymers usually do not have a structure like:

AAA-AA-BBB-BB.

In other embodiments, the poly(ethylene alpha-olefin) block copolymers usually do not have a third type of block, i.e., do not have a "C" block that is not an A block and not a B block. In still other embodiments, each of block A and block B of the poly(ethylene alpha-olefin) block copolymers has monomers or comonomers randomly distributed within the block. In other words, neither block A nor block B comprises two or more segments (or sub-blocks) of distinct composition, such as a tip segment, which has a different composition than the rest of the block.

In some embodiments, the polyolefin comprises an ethylene/α-olefin interpolymer, such as those described in U.S. Provisional Patent Application No. US 61/024,674 and family member PCT International Patent Application Publication Number WO 2009/097560, which are herein incorporated by reference, preferably a block copolymer, which comprises a hard segment and a soft segment, and is characterized by a $M_w/M_n$ in the range of from about 1.4 to about 2.8 and:

(a) has at least one $T_m$ (° C.), and a density (d) in grams/cubic centimeter, wherein the numerical values of $T_m$ and d correspond to the relationship:

$$T_m > -6553.3 + 13735(d) - 7051.7(d)^2, \text{ or}$$

(b) is characterized by a heat of fusion (ΔH, in J/g), and a delta temperature quantity (ΔT, in ° C.), defined as the temperature difference between the tallest DSC peak and the tallest crystallization analysis fractionation (CRYSTAF) peak, wherein the numerical values of ΔT and ΔH have the following relationships:

$$\Delta T > -0.1299(\Delta H) + 62.81 \text{ for } \Delta H \text{ greater than zero (0)}$$
$$\text{and up to 130 J/g,}$$

$$\Delta T \geq 48° \text{ C. for } \Delta H \text{ greater than 130 J/g,}$$

wherein the CRYSTAF peak is determined using at least 5 percent of the cumulative polymer, and if less than 5 percent of the polymer has an identifiable CRYSTAF peak, then the CRYSTAF temperature is 30° C.; or (c) is characterized by an elastic recovery ($R_e$) in percent at 300 percent strain and 1 cycle measured with a compression-molded film of the ethylene/α-olefin interpolymer, and has a density (d) in grams/cubic centimeter, wherein the numerical values of $R_e$ and d satisfy the following relationship when ethylene/α-olefin interpolymer is substantially free of a cross-linked phase:

$R_e > 1481 - 1629(d)$; or (d) has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer; or (e) has a storage modulus at 25° C. (G'(25° C.)) and a storage modulus at 100° C. (G' (100° C.)) wherein the ratio of G'(25° C.) to G'(100° C.) is in the range of about 1:1 to about 9:1; or (f) is characterized by an average block index greater than zero (0) and up to about 1.0; or (g) has a molecular fraction which elutes between 40° C. and 130° C. when fractionated using TREF, characterized in that the fraction has a molar comonomer content greater than, or equal to, the quantity (−0.2013) T+20.07, more preferably greater than or equal to the quantity (−0.2013) T+21.07, where T is the numerical value of the peak elution temperature of the TREF fraction, measured in ° C.; and, wherein the ethylene/α-olefin block interpolymer is mesophase separated.

In some embodiments, the polyolefin comprises an ethylene/α-olefin interpolymer, such as that described in U.S. Pat. No. 7,355,089 and U.S. Patent Application Publication No. US 2006-0199930, wherein the interpolymer is preferably a block copolymer, and comprises a hard segment and a soft segment, and the ethylene/α-olefin interpolymer:

(a) has a $M_w/M_n$ from about 1.7 to about 3.5, at least one $T_m$ (° C.), and a density d, in grams/cubic centimeter, wherein the numerical values of $T_m$ and d correspond to the relationship:

$Tm > -2002.9 + 4538.5(d) - 2422.2(d)2$; or (b) has a $M_w/M_n$ from about 1.7 to about 3.5, and is characterized by a heat of fusion, ΔH in J/g, and a delta quantity, ΔT (° C.), defined as the temperature difference between the tallest DSC peak and the tallest CRYSTAF peak, wherein the numerical values of ΔT and ΔH have the following relationships:

$\Delta T > -0.1299(\Delta H) + 62.81$ for ΔH greater than zero and up to 130 J/g, $\Delta T \geq 48°$ C. for ΔH greater than 130 J/g, wherein the CRYSTAF peak is determined using at least 5 percent of the cumulative polymer, and if less than 5 percent of the polymer has an identifiable CRYSTAF peak, then the CRYSTAF temperature is 30° C.; or (c) is characterized by an $R_e$ in percent at 300 percent strain and 1 cycle measured with a compression-molded film of the ethylene/α-olefin interpolymer, and has a density, d, in grams/cubic centimeter, wherein the numerical values of $R_e$ and d satisfy the following relationship when ethylene/α-olefin interpolymer is substantially free of a cross-linked phase:

$R_e > 1481 - 1629(d)$; or (d) has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer; or (e) has a storage modulus at 25° C. (G'(25° C.)), and a storage modulus at 100° C., (G'(100° C.)), wherein the ratio of G'(25° C.) to G'(100° C.) is in the range of about 1:1 to about 9:1 or (f) has a molecular fraction which elutes between 40° C. and 130° C. when fractionated using TREF, characterized in that the fraction has a block index of at least 0.5 and up to about 1 and a $M_w/M_n$ greater than about 1.3; or (g) has an average block index greater than zero (0) and up to about 1.0 and a $M_w/M_n$ greater than about 1.3; or (h) has a molecular fraction which elutes between 40° C. and 130° C. when fractionated using TREF, characterized in that the fraction has a molar comonomer content greater than, or equal to, the quantity (−0.2013) T+20.07, more preferably greater than or equal to the quantity (−0.2013) T+21.07, where T is the numerical value of the peak elution temperature of the TREF fraction, measured in ° C.

Other embodiments comprise polymers and processes such as those described in PCT International Patent Application Publication Nos. WO 2005/090425, WO 2005/090426, and WO 2005/090427.

Monomer and any comonomer content of the polyolefins may be measured using any suitable technique such as, for example, infrared (IR) spectroscopy and nuclear magnetic resonance (NMR) spectroscopy, with techniques based on NMR spectroscopy being preferred and carbon-13 NMR spectroscopy being more preferred. To use carbon-13 NMR spectroscopy, prepare an analysis sample from a polymer sample by adding approximately 3 g of a 50/50 mixture of tetrachloroethane-$d^2$/orthodichlorobenzene to 0.4 g of the polymer sample in a 10 millimeter (mm) NMR tube. Dissolve and homogenize the polymer sample by heating the tube and its contents to 150° C. Collect carbon-13 NMR spectroscopy data using a JEOL Eclipse™ 400 MHz spectrometer or a Varian Unity Plus™ 400 MHz spectrometer, corresponding to a carbon-13 resonance frequency of 100.5 MHz. Acquire the carbon-13 data using 4000 transients per data file with a 6 second pulse repetition delay. To achieve minimum signal-to-noise for quantitative analysis, add multiple data files together. The spectral width is 25,000 Hz with a minimum file size of 32,000 data points. Analyze the analysis sample at 130° C. in a 10 mm broad band probe. Determine the comonomer incorporation with the carbon-13 data using Randall's triad method (Randall, J. C.; JMS-Rev. Macromol. Chem. Phys., C29, 201-317 (1989), which is incorporated by reference herein in its entirety.

In some embodiments, the amount of olefin comonomer incorporated into the poly(olefin monomer-olefin comonomer) block copolymer or segments thereof is characterized by a comonomer incorporation index. As used herein, the term, "comonomer incorporation index", refers to the mole percent of residuals of olefin comonomer incorporated into olefin monomer/comonomer copolymer, or segment thereof, prepared under representative olefin polymerization conditions. Preferably, the olefin monomer is ethylene or propylene and the comonomer respectively is an ($C_3$-$C_{40}$)alpha-olefin or ($C_4$-$C_{40}$)alpha-olefin. The olefin polymerization conditions are ideally under steady-state, continuous solution polymerization conditions in a hydrocarbon diluent at 100° C., 4.5 megapascals (MPa) ethylene (or propylene) pressure (reactor pressure), greater than 92 percent (more preferably greater than 95 percent) olefin monomer conversion, and greater than 0.01 percent olefin comonomer conversion. The selection of catalyst compositions, which include the invention catalyst, having the greatest difference in olefin comonomer incorporation indices results in poly(olefin monomer-olefin comonomer) block copolymers from two or more olefin monomers having the largest difference in block or segment properties, such as density.

In certain circumstances the comonomer incorporation index may be determined directly, for example by the use of NMR spectroscopic techniques described previously or by IR spectroscopy. If NMR or IR spectroscopic techniques cannot be used, then any difference in comonomer incorporation is indirectly determined For polymers formed from multiple monomers this indirect determination may be accomplished by various techniques based on monomer reactivities.

For copolymers produced by a given catalyst, the relative amounts of comonomer and monomer in the copolymer and hence the copolymer composition is determined by relative rates of reaction of comonomer and monomer. Mathematically the molar ratio of comonomer to monomer is given by the equations described in US 2007/0167578 A1, in paragraphs numbered [0081] to [0090].

For this model as well the polymer composition is a function only of temperature dependent reactivity ratios and comonomer mole fraction in the reactor. The same is also true when reverse comonomer or monomer insertion may occur or in the case of the interpolymerization of more than two monomers.

Reactivity ratios for use in the foregoing models may be predicted using well known theoretical techniques or empirically derived from actual polymerization data. Suitable theoretical techniques are disclosed, for example, in B. G. Kyle, *Chemical and Process Thermodynamics*, Third Edition, Prentice-Hall, 1999 and in Redlich-Kwong-Soave (RKS) Equation of State, *Chemical Engineering Science*, 1972, pp 1197-1203. Commercially available software programs may be used to assist in deriving reactivity ratios from experimentally derived data. One example of such software is *Aspen Plus* from Aspen Technology, Inc., Ten Canal Park, Cambridge, Mass. 02141-2201 USA.

At times it is convenient to incorporate by reference examples of an associate olefin polymerization catalyst that can be used in embodiments of the invention process for polymerizing an olefin comprising chain shuttling and employing the invention catalyst. For convenience and consistency, one of the invention catalyst and associate olefin polymerization catalyst are thus sometimes referred to herein using generic terms such as a "first olefin polymerization catalyst" and one as a "second olefin polymerization catalyst" or vice versa That is, in some embodiments, the first olefin polymerization catalyst is the same as the invention catalyst and the second olefin polymerization catalyst is the same as the associate olefin polymerization catalyst; and vice versa in other embodiments. In some embodiments, the first and second olefin polymerization catalysts each independently is an invention catalyst. As used herein, the first olefin polymerization catalyst is characterizable as having a high comonomer incorporation index and the second olefin polymerization catalyst is characterizable as having a comonomer incorporation index that is less than 95 percent of the high comonomer incorporation index. Preferably, the second olefin polymerization catalyst is characterized as having a comonomer incorporation index that is less than 90 percent, more preferably less than 50 percent, still more preferably less than 25 percent, and even more preferably less than 10 percent of the high comonomer incorporation index of the first olefin polymerization catalyst.

When preparing the poly(ethylene alpha-olefin) block copolymer according to the preferred process of the third embodiment, the catalyst of the second embodiment is employed as part of a catalyst system, the catalyst system comprising a mixture or reaction product of:

(A) a first olefin polymerization catalyst, the first olefin polymerization catalyst being characterized as having a high comonomer incorporation index;

(B) a second olefin polymerization catalyst, the second olefin polymerization catalyst being characterized as having a comonomer incorporation index that is less than 90 percent of the comonomer incorporation index of the first olefin polymerization catalyst; and (C) a chain shuttling agent;

the catalyst of the second embodiment comprising either the first or second olefin polymerization catalyst.

The term "catalyst" as generally used herein may refer to an unactivated form of a metal-ligand complex (i.e., precursor) or, preferably, the activated form thereof (e.g., after contact of the unactivated form with an activating cocatalyst to give a catalytically active mixture or product thereof). For the associate olefin polymerization catalyst comprising or prepared from a non-invention metal-ligand complex, a metal of the non-invention metal-ligand complex can be a metal of any one of Groups 3 to 15, preferably Group 4, of the Periodic Table of the Elements. Examples of types of suitable non-invention metal-ligand complexes are metallocene, half-metallocene, constrained geometry, and polyvalent pyridylamine-, polyether-, or other polychelating base complexes. Such non-invention metal-ligand complexes are described in the WO 2008/027283 and corresponding U.S. patent application Ser. No. 12/377,034. Other suitable non-invention metal-ligand complexes are those described in U.S. Pat. No. 5,064,802; U.S. Pat. No. 5,153,157; U.S. Pat. No. 5,296,433; U.S. Pat. No. 5,321,106; U.S. Pat. No. 5,350,723; U.S. Pat. No. 5,425,872; U.S. Pat. No. 5,470,993; U.S. Pat. No. 5,625,087; U.S. Pat. No. 5,721,185; U.S. Pat. No. 5,783,512; U.S. Pat. No. 5,866,704; U.S. Pat. No. 5,883,204; U.S. Pat. No. 5,919,983; U.S. Pat. No. 6,015,868; U.S. Pat. No. 6,034,022; U.S. Pat. No. 6,103,657; U.S. Pat. No. 6,150,297; U.S. Pat. No. 6,268,444; U.S. Pat. No. 6,320,005; U.S. Pat. No. 6,515,155; U.S. Pat. No. 6,555,634; U.S. Pat. No. 6,696,379; U.S. Pat. No. 7,163,907; and U.S. Pat. No. 7,355,089, as well as in applications WO 02/02577; WO 02/92610; WO 02/38628; WO 03/40195; WO 03/78480; WO 03/78483; WO 2009/012215 A2; US 2003/0004286; and US 04/0220050; US 2006/0199930 A1; US 2007/0167578 A1; and US 2008/0311812 A1.

The "first olefin polymerization catalyst" is interchangeably referred to herein as "Catalyst (A)." The "second olefin polymerization catalyst" is interchangeably referred to herein as "Catalyst (B)." The selection of metal complexes or catalyst compositions having the greatest difference in comonomer incorporation indices results in copolymers from two or more monomers having the largest difference in block or segment properties, such as density.

Preferably, the comonomer incorporation index of Catalyst (B) is less than 50 percent and more preferably less than 5 percent of the comonomer incorporation index of Catalyst (A). An example of Catalyst (B) is the aforementioned "associate olefin catalyst."

In some embodiments, the catalyst of the second embodiment comprises Catalyst (A), but not Catalyst (B). In such embodiments, preferably the Catalyst (B) of the catalyst system is a Catalyst (B) described in US 2006/0199930 A1; US 2007/0167578 A1; US 2008/0311812 A1; U.S. Pat. No. 7,355,089 B2; or WO 2009/012215 A2.

In some embodiments, the catalyst of the second embodiment comprises Catalyst (B), but not Catalyst (A). In such embodiments, preferably the Catalyst (A) of the catalyst system is a Catalyst (A) described in US 2006/0199930 A1; US 2007/0167578 A1; US 2008/0311812 A1; U.S. Pat. No. 7,355,089 B2; or WO 2009/012215 A2.

Representative Catalysts (A) and (B) of US 2006/0199930 A1; US 2007/0167578 A1; US 2008/0311812 A1; U.S. Pat. No. 7,355,089 B2; or WO 2009/012215 A2 are the catalysts of formulas (A1) to (A5), (B1), (B2), (C1) to (C3), and (D1):

Catalyst (A1) is [N-(2,6-di(1-methylethyl)phenyl)amido) (2-isopropylphenyl)(α-naphthalen-2-diyl(6-pyridin-2-diyl) methane)]hafnium dimethyl, prepared according to the teachings of WO 03/40195, 2003US0204017, U.S. Ser. No. 10/429,024, filed May 2, 200, and WO 04/24740, and having the structure:

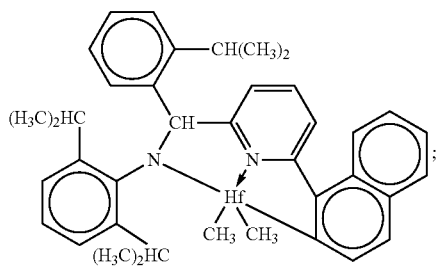

Catalyst (A2) is [N-(2,6-di(1-methylethyl)phenyl)amido) (2-methylphenyl)(1,2-phenylene-(6-pyridin-2-diyl)methane)]hafnium dimethyl, prepared according to the teachings of WO 03/40195, 2003US0204017, U.S. Ser. No. 10/429, 024, filed May 2, 2003, and WO 04/24740, and having the structure:

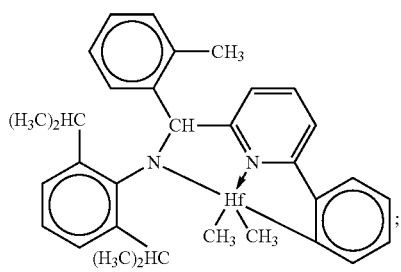

Catalyst (A3) is bis[N,N'''-(2,4,6-tri(methylphenyl)amido) ethylenediamine]hafnium dibenzyl, and having the structure:

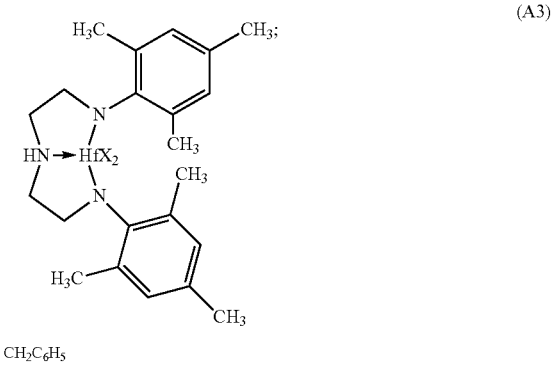

X = CH$_2$C$_6$H$_5$

Catalyst (A4) is bis((2-oxoyl-3-(dibenzo-1H-pyrrole-1-yl)-5-(methyl)phenyl)-2-phenoxymethyl)cyclohexane-1,2-diyl zirconium (IV) dibenzyl, prepared substantially according to the teachings of US-A-2004/0010103, and having the structure:

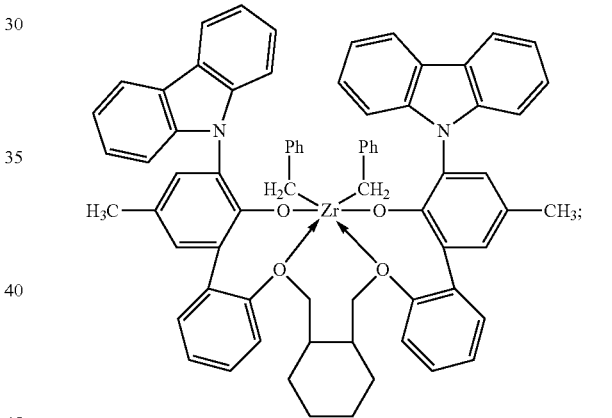

Catalyst (A5) is [η$^2$-2,6-diisopropyl-N-(2-methyl-3-(octylimino)butan-2-yl)benzeneamide]trimethylhafnium, prepared substantially according to the teachings of WO 2003/051935, and having the structure:

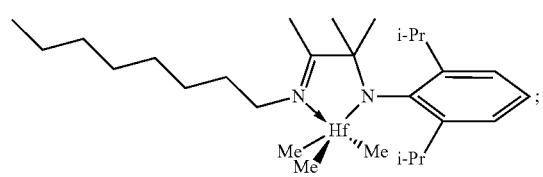

Catalyst (B1) is 1,2-bis-(3,5-di-t-butylphenylene)(1-(N-(1-methylethyl)imino)methyl)(2-oxoyl) zirconium dibenzyl, and having the structure:

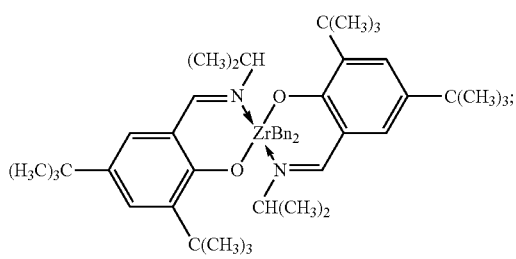

(B1)

Bn = CH₂C₆H₅

Catalyst (B2) is 1,2-bis-(3,5-di-t-butylphenylene)(1-(N-(2-methylcyclohexyl)-imino)methyl)(2-oxoyl) zirconium dibenzyl, and having the structure:

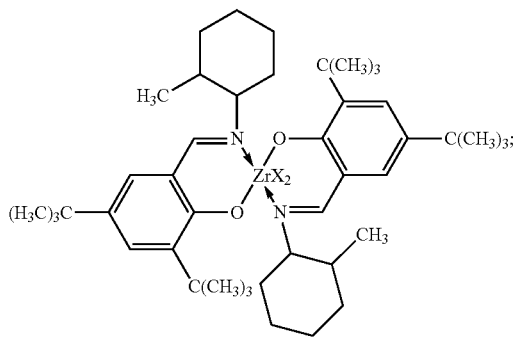

(B2)

X = CH₂C₆H₅

Catalyst (C1) is (t-butylamido)dimethyl(3-N-pyrrolyl-1,2,3,3a,7a-η-inden-1-yl)silanetitanium dimethyl, prepared substantially according to the techniques of U.S. Pat. No. 6,268,444, and having the structure:

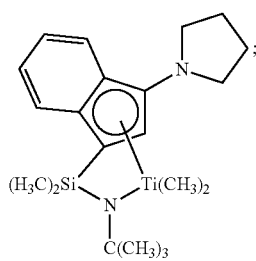

(C1)

Catalyst (C2) is (t-butylamido)di(4-methylphenyl)(2-methyl-1,2,3,3a,7a-η-inden-1-yl)silanetitanium dimethyl, prepared substantially according to the teachings of US-A-2003/004286, and having the structure:

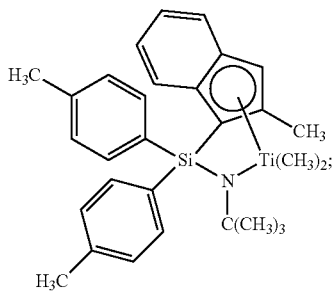

(C2)

Catalyst (C3) is (t-butylamido)di(4-methylphenyl)(2-methyl-1,2,3,3a,8a-η-indacen-1-yl)silanetitanium dimethyl, prepared substantially according to the teachings of US-A-2003/004286, and having the structure:

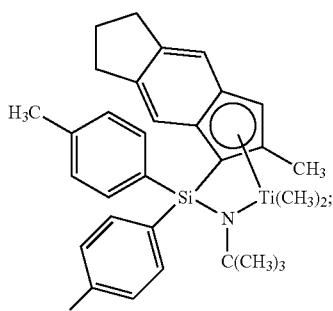

(C3)

and

Catalyst (D1) is bis(dimethyldisiloxane)(indene-1-yl)zirconium dichloride, available from Sigma-Aldrich, and having the structure:

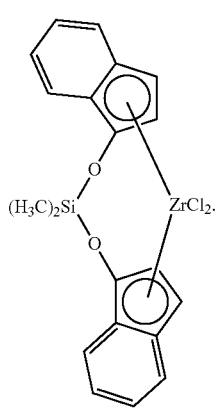

(D1)

As mentioned previously, some embodiments of the invention process for polymerizing an olefin further employ a chain shuttling agent. The terms "chain shuttling agent" and "CSA" are interchangeably used herein and refer to a compound that is characterizable as being capable of causing, under the olefin polymerization conditions, exchange of a polymeryl chain (i.e., polymer chain or fragment) between at least two active catalyst sites of two olefin polymerization catalysts, the two olefin polymerization catalysts being the invention catalyst and the associate olefin polymerization catalyst such as another invention catalyst or one of the non-invention catalysts described previously. That is, transfer of a polymer fragment occurs both to and from one or more of active sites of the olefin polymerization catalysts.

In contrast to a chain shuttling agent, a "chain transfer agent" causes termination of polymer chain growth and amounts to a one-time transfer of polymer from a catalyst (e.g., the invention catalyst) to the transfer agent. In some polymerization process embodiments such as those useful for preparing polyolefin homopolymers and random polyolefin copolymers, the CSA is characterizable of functioning as a chain transfer agent. That is, the CSA is characterizable as functioning in such a way that there is a one-time transfer of a polyolefin homopolymer or random polyolefin copolymer product formed in such polymerization process from the olefin polymerization catalyst (e.g., the invention catalyst) to the CSA. In such embodiments, it is not necessary for the CSA to reversibly chain shuttle, as such embodiments typically employ only one olefin polymerization catalyst, which may have or use only one active catalyst site.

In some embodiments, the chain shuttling agent is characterizable as having a chain shuttling activity ratio $R_{A-B}/R_{B-A}$. In general, for any two catalysts (A) and (B), the chain shuttling activity ratio $R_{A-B}/R_{B-A}$ is calculated by dividing a rate of chain transfer from an active site of a Catalyst (A) to an active site of a Catalyst (B) ($R_{A-B}$) by a rate of chain transfer from the active site of the Catalyst (B) to the active site of the Catalyst (A) ($R_{B-A}$). Preferably the Catalyst (A) is the invention catalyst and the Catalyst (B) is the aforementioned associate olefin polymerization catalyst. For the chain shuttling agent, preferably the chain shuttling activity ratio $R_{A-B}/R_{B-A}$ is from 0.01 to 100. Preferably, an intermediate formed between the chain shuttling agent and the polymeryl chain is sufficiently stable that chain termination is relatively rare. A (polyolefin-polyradical)-containing chain shuttling agent is an example of said intermediates.

By selecting different combinations of olefin polymerization catalysts having differing comonomer incorporation rates (as described herein) as well as differing reactivities, and by combining two or more CSAs (and preferably 3 or less CSAs), different poly(olefin monomer-olefin comonomer) multiblock copolymer products can be prepared in some embodiments of the invention process for polymerizing an olefin. Such different products can have segments of different densities or comonomer concentrations, different block lengths, different numbers of such segments or blocks, or a combination thereof. For example, if the chain shuttling activity of the chain shuttling agent is low relative to a polymer chain propagation rate of one or more of the olefin polymerization catalysts, longer block length multiblock copolymers and polymer blends may be obtained as products. Contrariwise, if chain shuttling is very fast relative to polymer chain propagation, a copolymer product having a more random chain structure and shorter block lengths is obtained. In generally, an extremely fast chain shuttling agent may produce a multiblock copolymer having substantially random copolymer properties. By proper selection of both catalyst(s) and the CSA, relatively pure block copolymers, copolymers containing relatively large polymer segments or blocks, and/ or blends of the foregoing with various ethylene or propylene homopolymers and/or copolymers can be obtained as products.

In some embodiments of the invention process for polymerizing an olefin employing the CSAs, the chain shuttling agents that are suitable for use therein include Group 1, 2, 12 or 13 metal compounds or complexes containing at least one ($C_1$-$C_{20}$)hydrocarbyl group, preferably ($C_1$-$C_{12}$)hydrocarbyl substituted aluminum, gallium or zinc compounds, and reaction products thereof with a proton source. Preferred ($C_1$-$C_{20}$) hydrocarbyl groups are alkyl groups, preferably linear or branched, ($C_1$-$C_8$)alkyl groups. Most preferred shuttling agents for use in the present invention are trialkyl aluminum and dialkyl zinc compounds, especially triethylaluminum, tri(i-propyl) aluminum, tri(i-butyl)aluminum, tri(n-hexyl) aluminum, tri(n-octyl)aluminum, triethylgallium, or diethylzinc. Additional suitable shuttling agents include the reaction product or mixture formed by combining the foregoing organometal compound, preferably a tri(($C_1$-$C_8$)alkyl) aluminum or di(($C_1$-$C_8$)alkyl) zinc compound, especially triethylaluminum, tri(i-propyl) aluminum, tri(i-butyl)aluminum, tri(n-hexyl)aluminum, tri(n-octyl)aluminum, or diethylzinc, with less than a stoichiometric quantity (relative to the number of hydrocarbyl groups) of a primary or secondary amine, primary or secondary phosphine, thiol, or hydroxyl compound, especially bis(trimethylsilyl)amine, t-butyl(dimethyl)silanol, 2-hydroxymethylpyridine, di(n-pentyl)amine, 2,6-di(t-butyl)phenol, ethyl(1-naphthyl) amine, bis(2,3,6,7-dibenzo-1-azacycloheptaneamine), diphenylphosphine, 2,6-di(t-butyl)thiophenol, or 2,6-diphenylphenol. Desirably, sufficient amine, phosphine, thiol, or hydroxyl reagent is used such that at least one hydrocarbyl group remains per metal atom. The primary reaction products of the foregoing combinations most desired for use in the present invention as shuttling agents are n-octylaluminum di(bis(trimethylsilyl)amide), i-propylaluminum bis(dimethyl (t-butyl)siloxide), and n-octylaluminum di(pyridinyl-2-methoxide), i-butylaluminum bis(dimethyl(t-butyl)siloxane), i-butylaluminum di(bis(trimethylsilyl)amide), n-octylaluminum di(pyridine-2-methoxide), i-butylaluminum bis(di(n-pentyl)amide), n-octylaluminum bis(2,6-di-t-butylphenoxide), n-octylaluminum di(ethyl(1-naphthyl) amide), ethylaluminum bis(t-butyldimethylsiloxide), ethylaluminum di(bis(trimethylsilyl)amide), ethylaluminum bis(2,3,6,7-dibenzo-1-azacycloheptaneamide), n-octylaluminum bis(2,3,6,7-dibenzo-1-azacycloheptaneamide), n-octylaluminum bis(dimethyl(t-butyl)siloxide), ethylzinc (2,6-diphenylphenoxide), and ethylzinc (t-butoxide). Other suitable non-invention chain shuttling agents are described in WO 2005/073283 A1; WO 2005/090425 A1; WO 2005/ 090426 A1; WO 2005/090427 A2; WO 2006/101595 A1; WO 2007/035485 A1; WO 2007/035492 A1; and WO 2007/ 035493 A2.

Polyolefins prepared by a process of the third embodiment are useful, among other things, as synthetic lubricants (synthetic motor oils) and as materials for use in manufacturing foams, films, coatings, fibers, fabrics, extruded articles, and molded articles.

The intermediate compound of formula (Y) may be made by adapting any relevant process known in the art and the particular process is not critical to the present invention. For example, the intermediate compound of formula (Y) wherein $R^2$ and $R^3$ are not replaced by the aforementioned diradical of formula ($R^{23}$) can be prepared by adapting the methods of U.S. Pat. No. 6,096,676 or U.S. Pat. No. 6,919,413 B2. For example the method of U.S. Pat. No. 6,096,676 is especially useful for preparing the intermediate compound of formula (Y) wherein each of $R^2$ and $R^4$ independently is hydrogen, ($C_1$-$C_{40}$)hydrocarbyl, or ($C_1$-$C_{40}$)heterohydrocarbyl; and $R^3$ is hydrogen. Such method of U.S. Pat. No. 6,096,676 preferably comprises adapting preparation of the heteroatom-containing ligand of U.S. Pat. No. 6,096,676 having the formula at column 3, lines 45 to 64, wherein W is a two carbon bridging group as at column 4, line 59, which heteroatom-containing ligand of U.S. Pat. No. 6,096,676 is exemplified at column 6, lines 1 to 19, and Examples 1, 3, and 6 thereof. The remaining intermediate compounds of formula (Y) wherein $R^2$ and $R^3$ are not replaced by the aforementioned diradical of formula ($R^{23}$) preferably are prepared by adapting the method of U.S. Pat. No. 6,919,413 B2. Such method of U.S. Pat. No. 6,919,413 B2 preferably comprises adapting preparation of the heteroatom-containing ligand of U.S. Pat. No. 6,919,413 B2 having the formula at column 9, line 50, wherein T is a two carbon bridging group as exemplified at column 4, lines 20 to 40, lines 45 to 47 (right-most group), and lines 50 to 60 thereof. Preparations of specific heteroatom-containing ligands of U.S. Pat. No. 6,919,413 B2 are described at column 23, line 56, to column 24, line 22; column 25, line 55, to column 26, line 67; column 35, line 59, to column 36, line 54; and column 37, line 21, to column 39, line 6, thereof.

Figure 2:
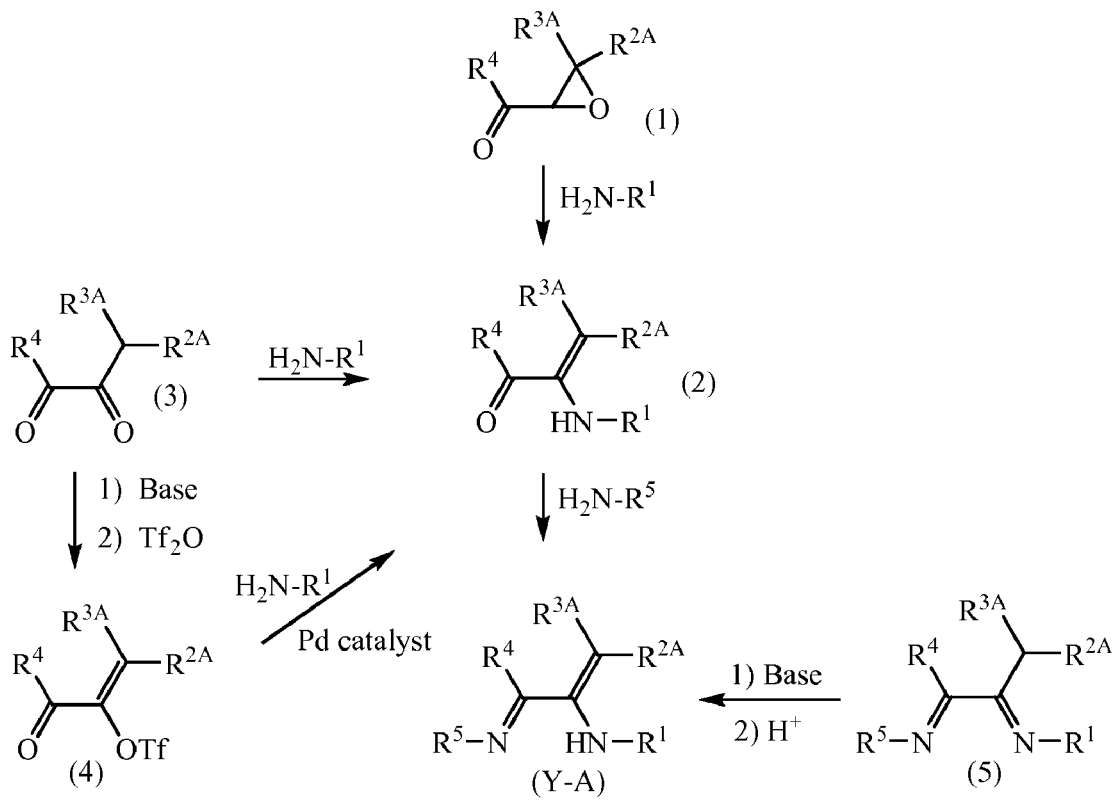
FIG. 2 shows illustrative procedures in Scheme 2 for preparing an intermediate compound of formula (Y-A).

The intermediate compound of formula (Y) wherein $R^2$ and $R^3$ are replaced by a diradical of formula ($R^{23}$) is a compound of formula (Y-A) and prepared according to one of the processes illustrated in Scheme 2 shown in FIG. 2. In FIG. 2 Scheme 2, epoxide (1), which preferably is prepared by conventional epoxidation (not shown) of a corresponding 2-enone, is allowed to react with an amine $R^1$—$NH_2$ or its conjugate anion $R^1$—N(H)$^-$, preferably under dehydrating conditions (e.g., in the presence of a dehydrating agent such as anhydrous 3-angstrom molecular sieves or anhydrous calcium carbonate, or under conditions such as azeotropic removal of water) to give enamine (2). Alternatively, enamine (2) is prepared by allowing a 1,2-diketone (3) to react with the amine $R^1$—$NH_2$, preferably under dehydrating conditions. Alternatively enamine (2) is prepared by deprotonating 1,2-diketone (3) with a non-nucleophilic base (e.g., sodium hydride, lithium diisopropylamide, potassium hexamethyldisilzide, and the like) followed by capturing of the resulting enolate anion with a sulfonylating agent (e.g., trifluoromethanesulfonic anhydride ($Tf_2O$)) to give keto-enol (4). Keto-enol (4) is then allowed to couple in the presence of palladium catalyst (e.g., palladium(II)acetate) with the amine $R^1$—$NH_2$ to give enamine (2). Enamine (2) is then allowed to react with an amine $R^5$—$NH_2$, preferably under dehydrating conditions, to give the intermediate compound of formula (Y-A). Alternatively, the intermediate compound of formula (Y-A) is prepared by deprotonating a bis-imine (5), which preferably is prepared by conventional condensation (not shown) of amines $R^1$—$NH_2$ and $R^5$—$NH_2$ with 1,2-diketone (3) under dehydrating conditions, with a non-nucleophilic base, followed by quenching of the resulting enamide with preferably 1 mole equivalent of a preferably anhydrous protic acid (e.g., trifluoroacetic acid).

The reactions described in FIG. 2 Scheme 2 preferably are carried out under a substantially inert gas atmosphere in an anhydrous aprotic solvent such as, for example, toluene, xylenes, tetrahydrofuran, diethylene glycol dimethyl ether, or a combination thereof and at a temperature in a range of from about −78° C. to about 200° C. Preferably, the reactions are carried out at atmospheric pressure.

Preferably, the intermediate compound of formula (Y) is the compound of any one of Preparations 1 to 13 (described later), or a salt of a conjugate base thereof.

Materials and Methods

General Ethylene/1-Octene Copolymerization Procedure.

A 2-liter Parr reactor is used in the polymerizations. All feeds are passed through columns of alumina and Q-5™ catalyst (available from Englehardt Chemicals Inc.) prior to introduction into the reactor. Solution of complex (1) and activating co-catalysts (activators) are handled under an inert atmosphere (e.g., nitrogen gas) in a glove box. A stirred 2-liter reactor is charged with about 533 g of mixed alkanes solvent (Isopar E) and 250 g of 1-octene comonomer. Hydrogen gas (45 psi) is added as a molecular weight control agent by differential pressure expansion from a 75 mL addition tank at 300 psi (2070 kiloPascals (kPa)). The reactor contents are heated to a polymerization temperature of 120° C. and saturated with ethylene at 466 psig (3.4 MPa). Metal-ligand Complex (1) and activating co-catalysts (i) and (ii) that are (i) 1.2 mole equivalents of a mixture of methyldi(($C_{14}$-$C_{18}$)alkyl)ammonium salts of tetrakis(pentafluorophenyl)borate, abbreviated herein as MDATPB, prepared by reaction of a long chain trialkylamine (a "di(tallow)methylamine"); ARMEEN™ M2HT, available from Akzo-Nobel, Inc.), HCl and Li[B($C_6F_5$)$_4$], substantially as disclosed in U.S. Pat. No. 5,919,9883, Ex. 2; and (ii) modified methylaluminoxane-3 Å (MMAO-3A) (10 mole equivalents), as dilute solutions in toluene, are mixed and transferred to a catalyst addition tank and injected into the reactor. The polymerization conditions are maintained for 15 minutes with ethylene added on demand. Heat is continuously removed from the reaction through an internal cooling coil. The resulting solution is removed from the reactor, quenched with isopropyl alcohol, and stabilized by addition of 10 mL of a toluene solution containing approximately 67 mg of a hindered phenol antioxidant (IRGANOX™ 1010 from Ciba Geigy Corporation) and 133 mg of a phosphorus stabilizer (IRGAFOS™ 168 from Ciba Geigy Corporation).

Between polymerization runs a wash cycle is conducted in which 850 g of mixed alkanes are added to the reactor and the reactor is heated to 150° C. The reactor is then emptied of the heated solvent immediately before beginning a new polymerization run.

Unless otherwise indicated, measure melting and crystallization temperatures of copolymers by DSC (DSC 2910, TA Instruments, Inc.). Samples of copolymers are first heated from room temperature to 210° C. at 10° C. per minute. After being held at this temperature for 4 minutes, the samples are cooled to −40° C. at 10° C. per minute and are then heated to 215° C. at 10° C. per minute after being held at −40° C. for 4 minutes.

Unless otherwise indicated, measure molecular weights of copolymers either on Symyx Technologies, Inc.'s SYMYX™ High-Throughput Gel Permeation Chromatographer (SHT-GPC) or Viscotek HT-350 Gel Permeation Chromatographer (V-GPC). The SHT-GPC utilized two Polymer Labs PLgel 10 µm MIXED-B columns (300×10 mm) at a flow rate of 2.5 mL/minute in 1,2,4-trichlorobenzene at 160° C. The V-GPC is equipped with a low-angle/right-angle light scattering detector, a 4-capillary inline viscometer and a refractive index detector. V-GPC analyses utilized three Polymer Labs PLgel 10 µm MIXED-B columns (300 mm×75 mm) at a flow rate of 1.0 mL/minute in 1,2,4-trichlorobenzene at either 145° C. or 160° C.

Unless otherwise indicated, prepare samples for SHT-GPC as follows: In a sample block, polymer sample is weighed out into glass sample tubes (Symyx Technologies) and diluted to 30 mg/mL in 1,2,4-trichlorobenzene (1,2,4-TCB). A glass stir bar is placed into each tube and the sample block is transferred to a heated shaker (160° C., 220 RPM) for 1 hour. Visual inspection of dissolution/sample viscosity is made, and solvent (1,2,4-TCB) is added to those which have not fully dissolved, or which are too thick for the SHT-GPC. The sample block is returned to the shaker for 15 minutes, and then transferred to the sample deck of the SHT-GPC, which is heated at 140° C. The samples are diluted by transferring a small aliquot of the 30 mg/mL solution into a second tube and adding solvent (1,2,4-TCB) to reach the desired concentration of 1 mg/mL, of which 500 µL are then injected into the GPC.

Unless otherwise indicated, prepare samples for V-GPC as follows: Polymer is weighed out into glass test-vials using the Semi-Automated Sample Preparation (SASP) program supplied by Viscotek, Inc. Once weighed out, 1,2,4-Trichlorobenzene is added to each sample by a computer-controlled syringe pump interfaced with the SASP program to give 1.00 mg/mL concentration. A Teflon-coated stir bar is placed into each and the tubes are capped and loaded into an aluminum block and placed on a heated shaker (160° C., 220 RPM) for 1 hour to 2 hours until total dissolution is observed upon visual inspection. The vials are then transferred to the heated deck of the autosampler (145° C. with magnetic stirring) where they await injection. A 270 µL injection of each sample is made, with a run time of 45 minutes.

General Considerations.

All solvents and reagents are obtained from commercial sources and used as received unless indicated otherwise. Toluene, hexanes, benzene-$d_6$ ($C_6D_6$), and toluene-$d_8$ are dried and degassed according to known procedures. Nuclear magnetic resonance (NMR) spectra are recorded on Varian Mercury-Vx-300 and VNMRS-500 spectrometers. Chemical shifts in parts per million (δ) are reported versus tetramethylsilane and referenced to residual protons in a deuterated solvent. NMR peak and coupling constant assignments are provided for convenience and are not limiting. Some of the atoms in the structures of the Preparations and Examples are numbered for ease of reference. All metal-ligand complexes are synthesized and stored in a Vacuum Atmospheres substantially inert atmosphere glove box under a dry nitrogen atmosphere or by using standard Schlenk and vacuum line techniques.

Determining Percent Incorporation of 1-Octene and Polymer Density by Infrared (IR) Spectroscopy.

Deposit 140 microliters (µL) of each polymer solution onto a silica wafer, heat at 140° C. until the 1,2,4-trichlorobenzne (TCB) evaporates, and analyze using a Nicolet Nexus 670 FT-IR with 7.1 version software equipped with an AutoPro auto sampler.

Gel Permeation Chromatography (GPC).

Determine weight average molecular weight ($M_w$) and polydispersity index: Determine $M_w$ and ratio of $M_w/M_n$ (polydispersity index or PDI) using a Polymer Labs™ 210 high temperature gel permeation chromatograph. Prepare samples using 13 mg of polyethylene polymer that is diluted with 16 mL of 1,2,4-trichlorobenzene (stabilized with butylated hydroxy toluene (BHT)), heat and shake at 160° C. for 2 hours.

Determining melting and crystallization temperatures and heat of fusion by Differential Scanning Calorimetry (DSC; DSC 2910, TA Instruments, Inc.): First heat samples from room temperature to 180° C. at a heating rate of 10° C. per minute. After being held at this temperature for 2 to 4 minutes, cool the samples to −40° C. at a cooling rate of 10° C. per minute; hold the sample at the cold temperature for 2 to 4 minutes, and then heat the sample to 160° C.

Analyzing end groups by proton-nuclear magnetic resonance ($^1$H-NMR) spectroscopy using a Varian 600 MHz NMR instrument and deuterated tetrachloroethane.

Abbreviations (meanings): κ (kappa); i-Pr (isopropyl, i.e., 2-propyl); Ph (phenyl); Bn (benzyl); Me (methyl); nBu, n-Bu and the like (normal-butyl); $CH_2Cl_2$ (dichloromethane); $CD_2Cl_2$ (dichlorodeuteromethane); THF (tetrahydrofuran); p-TsOH.H$_2$O (para-toluenesulfonic acid monohydrate); $TiCl_4$ (titanium(IV) chloride); $K_2CO_3$ (potassium carbonate); Me (methyl); $C_6D_6$ (perdeuterobenzene); toluene-$d_8$ (perdeuterotoluene); $Et_3N$ (triethylamine); $ZrBn_4$ (zirconium tetrabenzyl); $HfBn_4$ and $Hf(CH_2Ph)_4$ (hafnium tetrabenzyl); r.t. (room temperature); g (gram(s)); mL (milliliter(s)); ° C. (degrees Celsius); × (times (as in 2×15 mL)); mmol (millimole(s)); psi (pounds per square inch); psig (pounds per square inch gage); MHz (MegaHertz); Hz (Hertz) m/z (mass-to-charge); 1H-NMR (proton NMR); 13C-NMR (carbon-13 NMR); 19F-NMR (fluorine-19 NMR); HSQC (heteronuclear single quantum coherence); Anal. (elemental analysis); calcd (calculated); br (broad); sept. (septet); s (singlet); d (doublet); t (triplet); m (multiplet); quat. (quartet); J (coupling constant); HRMS (high resolution mass spectrometry); ESI (electrospray mass spectrometry) and GC/MS (CI) (gas chromatography-mass spectrometry chemical ionization); TLC (thin layer chromatography).

Benzyl metals and other organo metals such as alkyl metals and trialkylsilyl metals, wherein the metals are $M^1$ as defined for formula (I), are useful starting materials for reacting with compounds of formula (Y) to give certain metal-ligand complexes of formula (I). It is not critical how such organo metals are prepared. In some embodiments, such organo metals are prepared starting from a corresponding metal halide (e.g., metal chloride or bromide) or metal alkoxide (e.g., metal tetrabutoxide) and an organo lithium or organo magnesium halide. For example, in some embodiments, such benzyl metals are prepared as described in U.S. Pat. No. 7,067,686 B1. The corresponding metal halides typically are available commercially such as, for example, from the Sigma-Aldrich Company, Saint Louis, Mo., USA and CHEMOS GmbH, Regenstauf, Germany. In other embodiments, such benzyl metals are purchased from a commercial source (for example, CHEMOS GmbH sells tetrabenzylhafnium under catalog number 151655 and tetrabenzylzirconium under catalog number 150405).

X-Ray Analysis.

X-ray analysis is performed as described here.

Data Collection: A single crystal of suitable dimensions is immersed in oil, PARATONE® N (Chevron Intellectual Property LLC), available from Exxon Chemicals, Inc., and mounted on a thin glass fiber. The crystal is transferred to a Bruker SMART™ Platform diffractometer equipped with a graphite monochromatic crystal, a MoKα radiation source (λ=0.71073 Å), and a CCD (charge coupled device) area detector. The crystal is bathed in a cold nitrogen stream for the duration of data collection (−100° C.).

Program SMART™ (available from Bruker AXS, Inc., Madison, Wis., USA) is used for diffractometer control, frame scans, indexing, orientation matrix calculations, least squares refinement of cell parameters, crystal faces measurements and the actual data collection. Program ASTRO™ (available from Bruker AXS, Inc., Madison, Wis., USA) is used to set up data collection strategy.

Raw data frames are read by program SAINT™ (available from Bruker AXS, Inc., Madison, Wis., USA) and integrated using 3D profiling algorithms The resulting data are reduced to produce hkl reflections and their intensities and estimated standard deviations. The data are corrected for Lorentz and polarization effects. Sufficient reflections are collected to represent a range of 1.51 to 2.16 redundancy level with an $R_{sym}$ value range of 2.5 percent, at the lowest 2θ shell of reflections, to 3.0 percent at the highest 2θ shell of reflections (55°). Crystal decay correction is applied and is less than 1 percent. The unit cell parameters are refined by least squares of the setting angles of the reflections.

Absorption corrections are applied by integration based on indexed measured faces. Data preparation is carried out using program XPREP™ (available from Bruker AXS, Inc., Madison, Wis., USA). The structure is solved by direct methods in SHELXTL5.1™ (available from Bruker AXS, Inc., Madison, Wis., USA) from which the positions of all of the non-H atoms are obtained. The structure is refined, also in SHELXTL5.1™, using full-matrix least-squares refinement. The non-H atoms are refined with anisotropic thermal parameters and all of the H atoms are calculated in idealized positions and refined riding on their parent atoms, or are obtained from a Difference Fourier map and refined without any constraints. A correction for secondary extinction is not applied. The final refinement is carried out using $F^2$ rather than F values. $R_1$ is calculated to provide a reference to the conventional R value but its function is not minimized Additionally, $wR_2$ is the function that is minimized, and not $R_1$.

The linear absorption coefficient, atomic scattering factors and anomalous-dispersion corrections are calculated from values from the International Tables for X-ray Crystallography (1974). Vol. IV, p. 55. Birmingham: Kynoch Press (Present distributor, D. Reidel, Dordrecht.).

Relevant functions:

$R_1=\Sigma(||F_o|-|F_c||)/\Sigma|F_o|$ $wR_2[\Sigma[w(F_o^2-F_c^2)^2]/\Sigma[wF_o^{22}]]^{1/2}$ $R_{int.}=\Sigma|F_o^2-F_o^2(\text{mean})|^2/\Sigma[F_o^2]$ $S[\Sigma[w(F_o^2-F_c^2)^2]/(n-p)]^{1/2}$ where n is the number of reflections and p is the total number of parameters refined $w=1/[\sigma^2(F_o^2)+(0.0370*p)^2+0.31*p], p=[\max(F_o^2,0)+2*F_c^2]/3$ All thermal ellipsoids described herein are depicted at the 40% probability level.

Reactions preparing or using a metal-ligand complex are run in a glove box under nitrogen unless otherwise noted.

Preparations

Preparation 1: preparation of (E)-N-(2-(2,6-diisopropylphenylamino)cyclohex-2-enylidene)-2,6-diisopropylaniline (a) is hereby incorporated by reference from Preparation 1 of U.S. nonprovisional patent application Ser. No. 12/544,581, filed Aug. 20, 2009, and repeated here.

Cyclohexane-1,2-dione (2.062 g, 18.39 mmol) and 2,6-diisopropylaniline (6.52 g, 36.78 mmol) are dissolved in 70 mL of methanol. To this solution is added 1 mL of formic acid and the mixture is stirred for 3 days at room temperature. Precipitated white crystalline solid is collected on the frit, washed with methanol (2×15 mL) and dried under reduced pressure to give 4.1 g (51.8% yield) of title compound (a) of Preparation 1.

Preparation 2: preparation of 2-(morpholin-4-yl)-2-cyclohexen-1-one is hereby incorporated by reference from Preparation 2 of U.S. nonprovisional patent application Ser. No. 12/544,581, filed Aug. 20, 2009, and repeated here.

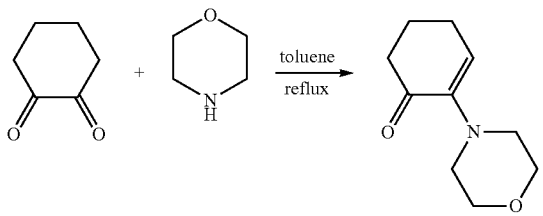

Synthesis based on literature modified procedure (Ohashi, M.; Takahashi, T.; Inoue, S.; Sato, K. Bulletin Chemical Society of Japan, 1975; 48:1892). A 500-mL round-bottomed flask is equipped with a Dean Stark trap, condenser, stir bar and gas inlet ($N_2$ gas atmosphere). The flask is charged with of 1,2-cyclohexanedione (15.14 g, 135.00 mmol), morpholine (14.82 g, 170.10 mmol) and toluene (330 mL). The resulting yellow solution is heated to reflux for 5 hours. Heating is stopped and about 3.0 mL of water are collected on the Dean Stark trap. The brown solution is decanted away from a thick oil and rinsed with toluene. The solution is concentrated under high vacuum to afford 23.33 g (95.34% yield) of title compound of Preparation 2 as a brown solid.

$^1$H NMR ($C_6D_6$, 300 MHz, 30° C.) δ 5.35 (t, 1H, $^3J$=4.6 Hz), 3.67-3.64 (m, 4H), 2.70-2.66 (m, 4H), 2.18-2.13 (m, 2H, H2), 1.87-1.81 (m, 2H, H4), 1.42 (quintet, 2H, $^3J$=6.4 Hz, H3).

GC/MS (CI) mass spectrum: m/z 182 (M+H).

Preparation 3: preparation of 2-(2,6-diisopropylphenylamino)cyclohex-2-enone is hereby incorporated by reference from Preparation 3 of U.S. nonprovisional patent application Ser. No. 12/544,581, filed Aug. 20, 2009, and repeated here.

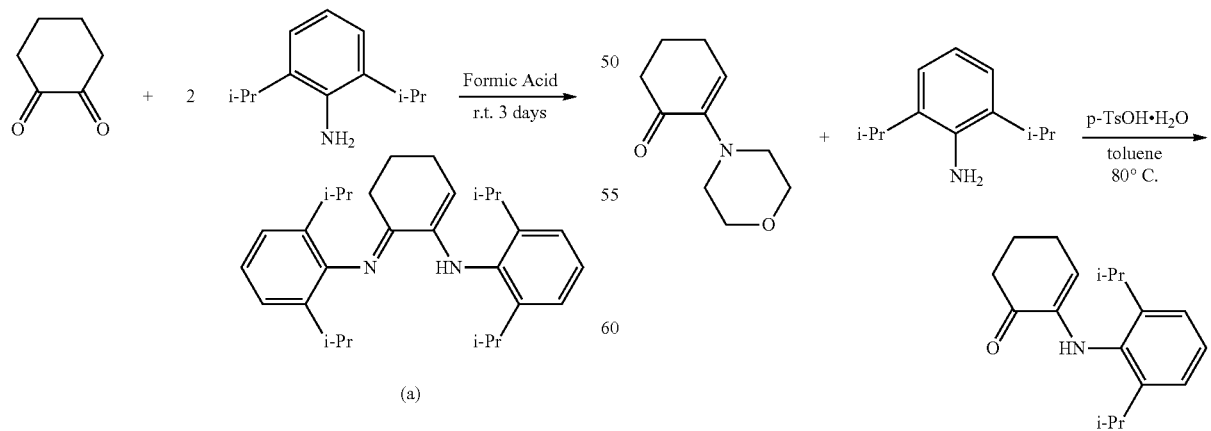

(a)

Synthesis based on literature procedure (Gates, D. P.; Svejda, S. A. Onate, E.; Killian, C. M.; Johnson, L. K.; White, P. S.; Brookhart M. Macromolecules, 2000; 33:2320-2334.).

A 250-mL three-necked round-bottomed flask equipped with a condenser, gas inlet and septas is placed under $N_2$ atmosphere. The flask is charged with 2-(morpholin-4-yl)-2-cyclohexen-1-one (7.0046 g, 38.65 mmol; Preparation 2), toluene (74.0 mL) and 2,6-diisopropylaniline (6.8521 g, 38.65 mmol) To the yellow solution is added p-toluenesulfonic acid monohydrate (7.3520 g, 38.65 mmol; p-TsOH·H₂O). The reaction mixture became very thick with a lot of precipitate. The mixture is heated to 80° C. (oil bath temperature) and allowed to stir. Another 5.0 mL of toluene are added to facilitate stirring. The mixture is stirred for 2 hours. Reaction mixture is allowed to reach room temperature. The mixture is filtered. The filtrate is concentrated under high vacuum to afford 10.09 g of a yellow solid. The solid is dissolved in hot hexanes (about 30 mL) and filtered. The solution is allowed to cool to room temperature, seeded and place on the freezer. The solution is filtered while most of the solid is left behind on the flask. The flask is placed on an ice bath. The solid is rinsed with two about 6 mL portions of cold hexanes. The yellow solid is allowed to dry, transfer to a vial and left to dry overnight under vacuum (first crop: 4.0550 g). Mother liquor is concentrated and recrystallization is repeated two more times. The second crop is left in the freezer for 5 hours (second crop: 1.0785 g) and third crop is left overnight (third crop: 0.6919 g). The combined yield of title compound of Preparation 3 is 5.8254 g (55.54%).

¹H NMR (C₆D₆, 300 MHz) δ 7.17-7.06 (m, 3H), 6.00 (broad s, 1H), 4.95 (t, 1H, J=4.7 Hz), 3.15 (septet, 2H, J=6.9 Hz), 2.21-2.16 (m, 2H, H2), 1.75 (q, 2H, J=5.5 Hz, H4), 1.41 (quintet, 2H, J=6.3 Hz, H3), 1.10 (d, 12H, J=6.9 Hz).

GC/MS (CI) mass spectrum: m/z 272 (M+H). HRMS (ESI, M+Na)⁺): (m/z calcd for C₁₈H₂₅NONa 294.180. found 294.183.

Preparation 4: preparation of an polymeric n-butylaminotitanium reagent (Ti(N(n-Bu)₂)ᵣ is hereby incorporated by reference from Preparation 4 of U.S. nonprovisional patent application Ser. No. 12/544,581, filed Aug. 20, 2009, and repeated here.

Ti(NMe₂)₄ (26 g, 0.116 mol) is dissolved in 500 mL of toluene in the dry box in the Schlenk flask. Flask is taken in the hood. To this solution are added 68.8 mL (0.696 mol) of n-butylamine which caused formation of orange solid. The mixture is heated at very small reflux with nitrogen sweep at the top of the condenser. Yellow solution became deep red within minutes after heating. After 6 hours of reflux, solution is cooled to room temperature and solvent is removed under reduced pressure to give deep-red-black glassy solid. The product is transferred into the dry box for storage. Obtained 23.2933 g of title reagent of Preparation 4, wherein r indicates a number of repeat units of Ti(N(n-Bu)₂.

Preparation 5: preparation of 2,(2,6-diisopropylphenylamino)-3,5-dimethylcyclopent-2-enone is hereby incorporated by reference from Preparation 6 of U.S. nonprovisional patent application Ser. No. 12/544,581, filed Aug. 20, 2009, and repeated here.

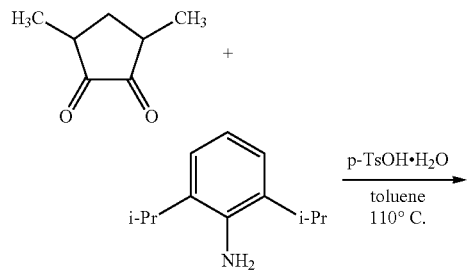

-continued

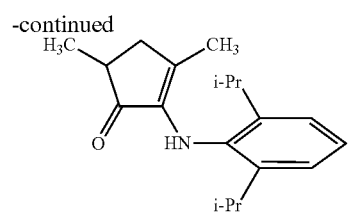

Follow a procedure similar to that of Preparation 3 except use 3,5-dimethyl-1,2-cyclopentadione (1.5043 g, 11.9237 mmol), toluene (6.0 mL), 2,6-diisopropylaniline (2.4 mL, 12.7117 mmol) and para-toluenesulfonic acid monohydrate (0.4584 g, 2.4098 mmol); heat to reflux (oil bath temperature: 150° C.); and purify the resulting mixture directly (allowable due to relatively small volume thereof) on a silica gel column for chromatography, eluting with 5% ethyl acetate/95% hexanes to afford 2.5156 g (73.9%) of 2,(2,6-diisopropylphenylamino)-3,5-dimethylcyclopent-2-enone as a yellow solid.

¹H NMR (C₆D₆, 500 MHz, 30° C.) δ 7.15 (broad t, 1H, J=7.6 Hz, para-Ph), 7.05 (d, 2H, J=7.7 Hz, meta-Ph), 5.45 (S, 1H, NH), 3.28 (broad s, 2H, CH(CH₃)₂), 2.22-2.14 (m, 2H, H2 and H3), 1.63-1.58 (m, 1H, H3), 1.21 (s, 3H, CHCH₃), 1.10 (d, 15H, J=6.8 Hz, C=CCH₃) and CH(CH₃)₂.

Not shown are ¹³C NMR (C₆D₆, 125 MHz, 30° C.) and HRMS (ESI, (M+H)⁺) data.

Preparation 6: preparation of 2-((1,1':3',1''-terphenyl)-2'-ylamino)-2-cyclohexen-1-one is hereby incorporated by reference from Preparation 7 of U.S. nonprovisional patent application Ser. No. 12/544,581, filed Aug. 20, 2009, and repeated here.

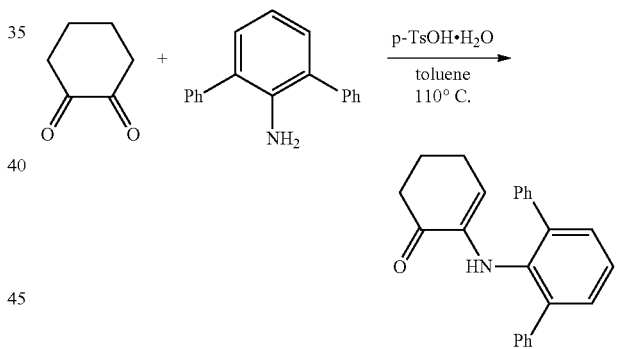

Follow a procedure similar to that of Preparation 2 except use 1,2-cyclohexanedione (1.0099 g, 9.0065 mmol); 2,6-diphenylaniline (2.2258 g, 9.0731 mmol); toluene (22 mL); p-toluenesulfonic acid monohydrate (0.0859 g, 0.4516 mmol); reflux reaction mixture for 2.3 hours; to isolate 3.5678 g of a brown thick oil. Purify the thick oil be chromatography using a Biotage SNAP 50 g KP-Sil column, loading the thick oil with small amount of 4% ethyl acetate/96% hexanes and 100% ethyl acetate and eluting with a gradient of 4-8% ethyl acetate in hexanes to afford after isolation 1.1388 g (37.2%) of the 2-((1,1':3',1''-terphenyl)-2'-ylamino)-2-cyclohexen-1-one as a yellow thick oil.

¹H NMR (C₆D₆, 500 MHz, 30° C.) δ 7.38 (d, 4H, J=7.2 Hz, Ph), 7.24 (d, 2H, J=7.6 Hz, Ph), 7.14 (t, 4H, J=7.8 Hz, Ph), 7.06 (t, 3H, J=7.6 Hz, Ph), 6.20 (s, 1H, NH), 5.09 (t, 1H, J=4.7 Hz, H5), 1.89 (t, 2H, J=6.6 Hz, H2), 1.58 (q, 2H, J=5.4 Hz, H4), 1.11 (quintet, 2H, J=6.3 Hz, H3).

Not shown are ¹³C NMR (C₆D₆, 125 MHz, 30° C.) and HSQCAD (C₆D₆, 500 MHz, 30° C.) data.

Preparation 7: preparation of (E)-N-(6-(Butylimino)cyclohex-1-enyl)-2,6-diisopropylaniline (B) is hereby incorporated by reference from Example B of U.S. nonprovisional patent application Ser. No. 12/544,581, filed Aug. 20, 2009, and repeated here.

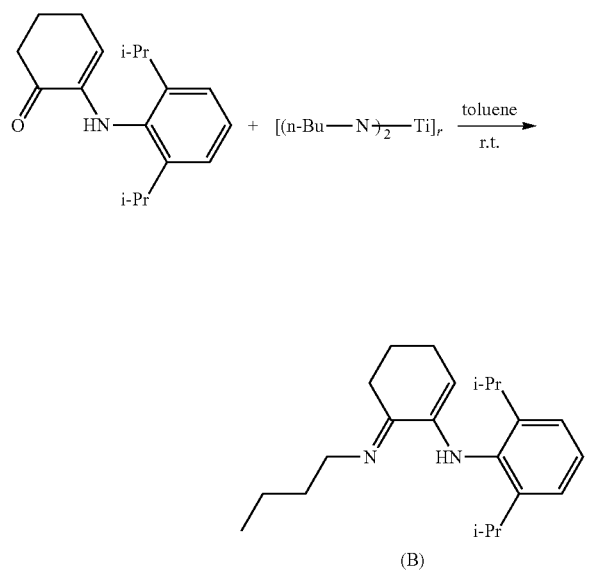

(B)

The r indicates a number of repeat units of Ti(N(n-Bu))$_2$. Reaction is set up in a glove box under N$_2$ atmosphere. A 20-mL vial equipped with a stir bar is charged with (0.4858 g, 1.7900 mmol) of 2-(2,6-diisopropylphenylamino)cyclohex-2-enone (Preparation 3), toluene (6.0 mL) and (0.3022 g, 0.8984 mmol) of polymeric n-butylamino-titanium reagent (Preparation 4). The mixture is stirred overnight (24 hours). $^1$H-NMR of aliquot showed reaction is not complete. About 26% of starting material remained Therefore, to the mixture are added 46.2 mg of polymeric n-butylamino-titanium reagent (Preparation 4). After stirring overnight, $^1$H-NMR of aliquot showed that no starting material remained To the mixture are added hexanes, and the resulting mixture is filtered. Hexanes are also used to wash filtercake solids. The filtrate (yellow solution) is concentrated under reduced pressure to afford 305.8 mg (52.3%) of compound (B) of Preparation 7 as a yellow oil.

$^1$H NMR (C$_6$D$_6$, 500 MHz, 30° C.) δ 7.23-7.17 (m, 3H, iPr$_2$-Ph), 6.89 (s, 1H, NH), 4.78 (t, 1H, J=4.6 Hz, H5), 3.39 (septet, 2H, $^3$J=6.9 Hz, CH(CH$_3$)$_2$), 3.26 (t, 2H, $^3$J=6.8 Hz, H7), 2.09 (pseudo t, 2H, $^3$J=6.6 Hz, H2), 1.96 (q, 2H, $^3$J=5.5 Hz, H4), 1.69 (pentet of multiplets, 2H, $^3$J=7.8 Hz, H8), 1.53 (quintet, 2H, $^3$J=6.5 Hz, H3), 1.44 (sextet of multiplets, 2H, $^3$J=7. Hz, H9), 1.22 (d, 12H, $^3$J=6.8 Hz, CH(CH$_3$)$_2$), 0.94 (t, 3H, $^3$J=7.3 Hz, H10).

HRMS (ESI, M+H)$^+$): (m/z) calcd for C$_{22}$H$_{35}$N$_2$ 327.277, found 327.280.

Preparation 8: alternate preparation of (E)-N-(6-(Butylimino)cyclohex-1-enyl)-2,6-diisopropylaniline (also named N-((6E)-6-(butylimino)-1-cyclohexen-1-yl)-2,6-bis(1-methylethyl)-benzenamine) (B) is hereby incorporated by reference from Example C of U.S. nonprovisional patent application Ser. No. 12/544,581, filed Aug. 20, 2009, and repeated here.

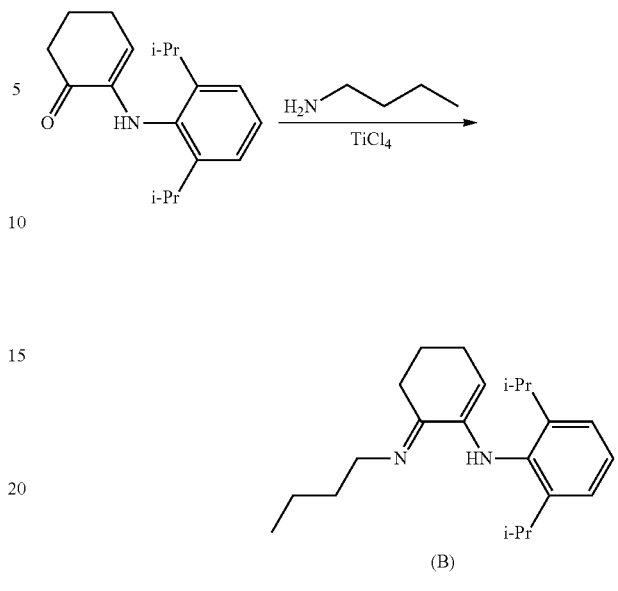

(B)

Reaction is set up in a glove box under N$_2$ atmosphere. To normal-butyl amine (n-BuNH$_2$) dissolved in 40 mL of toluene is added within 45 seconds TiCl$_4$ dissolved in 5 mL of toluene. Reaction mixture turns red during addition and then orange about a minute after the addition is complete. Temperature increases during addition from 27° C. to 49° C., and starts decreasing two minutes after the addition is complete.

After stirring for 1.5 hour at room temperature, 2-((2,6-bis (1-methylethyl)phenyl)amino)-2-cyclohexen-1-one (Preparation 3) is added as a solid. Resulting reaction mixture is stirred at ambient temperature for 3.25 hours. Reaction mixture is filtered (light yellow filtrate) through a medium frit into a vessel containing 2.1 g of anhydrous K$_2$CO$_3$, and the filtercake (salts) is washed time times with hexane (2×15 mL). The suspension is stirred for 2 hours with K$_2$CO$_3$, and then filtered (with a syringe filter) to give a colorless solution (K$_2$CO$_3$ absorbs yellow color from the solution). Solvent is removed from the solution under reduced pressure to give 4.66 g (95.6% yield) of compound (B) of Preparation 8 as a colorless oil. $^1$H NMR and HRMS of the product is consistent with compound (B) of Preparation 8 and the $^1$H NMR and HRMS of compound (B) of Preparation 7.

Preparation 9: preparation of N-(2,6-diisopropylphenyl)-2-butylaminotroponimine (D) is hereby incorporated by reference from Example D of U.S. nonprovisional patent application Ser. No. 12/544,581, filed Aug. 20, 2009, and repeated here.

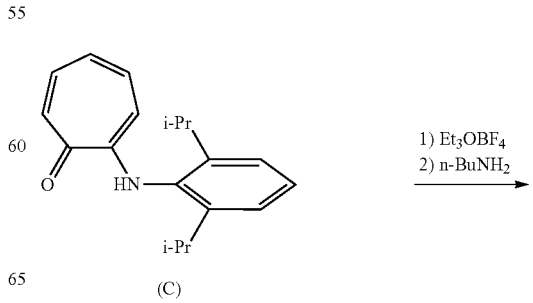

(C)

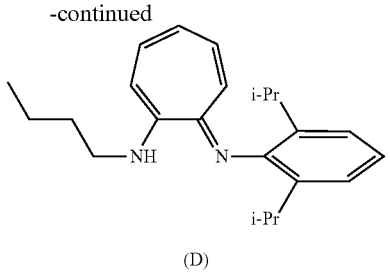

(D)

Prepare 2-(2,6-diisopropylanilino)tropone (C) by refluxing over a Dean-Stark trap a solution tropolone (Sigma-Aldrich Co., catalog no. T89702) and 2,6-bis(1,1-dimethylethyl) aniline in toluene with a catalytic amount of p-TsOH in a manner similar to the procedure of Preparation 5.

Et$_3$OBF$_4$ (418 mg, 2.20 mmol) is dissolved in CH$_2$Cl$_2$ (5 mL). A solution of 2-(2,6-diisopropylanilino)tropone (C) (587 mg, 2.09 mmol) in CH$_2$Cl$_2$ (15 mL) is slowly added. After stirring at 25° C. for 3 hours, the solution is cooled to about 0° C., and a pre-cooled (0° C.) solution of n-BuNH$_2$ (1.467 g, 20 mmol) in CH$_2$Cl$_2$ (5 mL) is added. The solution is allowed to warm to 25° C. and stirred overnight. The solvent is removed under vacuum, and the residue purified by column chromatography (eluent:hexane:Et$_2$O 3:1 containing 3 vol % Et$_3$N) afforded 557 mg (80% yield) of essentially pure compound (D) of Preparation 9 as an orange solid.

$^1$H NMR (C$_6$D$_6$, 500 MHz, 30° C.): 7.89 (br s, 1H, NH), 7.25 (d, J$_{H-H}$=7.7 Hz, 2H, H10, H12), 7.15 (tm, J$_{H-H}$=7.7 Hz, 1H, H11), 6.64 (tm, J$_{H-H}$=10.1 Hz, 1H, H5), 6.50 (d, J$_{H-H}$=12.0 Hz, 1H, H2), 6.31 (m, 1H, H3), 6.02 (tm, J$_{H-H}$=9.2 Hz, 1H, H4), 5.92 (d, J$_{H-H}$=10.0 Hz, 1H, H6), 2.98 (septet, J$_{H-H}$=6.8 Hz, 2H, CH(CH$_3$)$_2$), 2.86 (t, J$_{H-H}$=7.0 Hz, 2H, H14), 1.30 (m, 2H, H15), 1.20 (d, J$_{H-H}$=6.8 Hz, 6H, CH(CH$_3$)$_2$), 1.17 (m, 2H, H16), 1.14 (d, J$_{H-H}$=6.8 Hz, 6H, CH(CH$_3$)$_2$), 0.71 (t, J$_{H-H}$=7.3 Hz, 3H, H17).

Anal. Calcd for C$_{23}$H$_{32}$N$_2$: C, 82.09; H, 9.58; N, 8.32. Found: C, 82.36; H, 9.45; N, 8.42.

Preparation 10: preparation of (E)-N-(5-(butylimino)-2,4-dimethylcyclopent-1-enyl)-2,6-diisopropylaniline (G) is hereby incorporated by reference from Example G of U.S. nonprovisional patent application Ser. No. 12/544,581, filed Aug. 20, 2009, and repeated here.

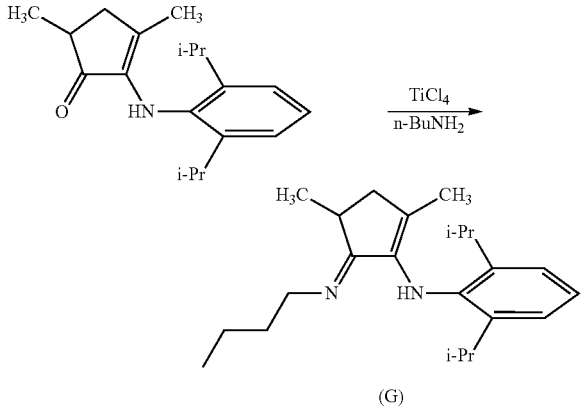

(G)

Follow a procedure similar to that of Preparation 8 except use n-butylamine (0.3098 g, 4.23 mmol); toluene (5.0 mL); then a solution of titanium(IV) chloride (0.0841 g, 0.44 mmol) in toluene (2.0 mL); and then a solution of the 2-(2,6-diisopropylphenylamino)-3,5-dimethylcyclopent-2-enone (0.2056 g, Preparation 5) in toluene (2 mL); and stir reaction mixture overnight; yield 0.2253 g (91.8%) of the product (G) as a brown oil.

$^1$H NMR (C$_6$D$_6$, 500 MHz, 30° C.) δ 7.17 (t, 1H, $^3$J=7.8 Hz, i-Pr$_2$-para-Ph), 7.09 (d, 2H, $^3$J=7.5 Hz, i-Pr$_2$-meta-Ph), 5.95 (s, 1H, NH), 3.58 (dt, 1H, $^2$J=13 Hz, $^3$J=6.5 Hz, H6), 3.50 (br. sep. 1H, $^3$J=6.0 Hz, (CH$_3$)$_2$CH-Ph), 3.42 (br. sep. 1H, $^3$J=6.0 Hz, (CH$_3$)$_2$CH-Ph), 3.41 (dt, 1H, $^2$J=13 Hz, $^3$J=7 Hz, H6), 2.63 (t, 1H, $^3$J=7 Hz, H2), 2.45 (dd, 1H, $^2$J=16 Hz, $^3$J=6 Hz, H3), 1.74 (m, 2H, H7), 1.67 (d, 1H, $^2$J=16 Hz, H3), 1.46 (m, 2H, H8), 1.26 (s, 1H, CH$_3$), 1.22 (br. d, 3H, $^3$J=6.5 Hz, (CH$_3$)$_2$CH), 1.18 (br. d, 3H, $^3$J=6 Hz, (CH$_3$)$_2$CH), 1.14 (br. d, 3H, $^3$J=6 Hz, (CH$_3$)$_2$CH-Ph)), 1.13 (br. d, 3H, $^3$J=6 Hz, (CH$_3$)$_2$ CH-Ph)), 1.03 (d, 3H, $^3$J=7 Hz, CH$_3$), 0.93 (t, 3H, $^3$J=7.4 Hz, H9).

Not shown are $^{13}$C NMR (C$_6$D$_6$, 125 MHz, 30° C.), HSQCAD (C$_6$D$_6$, 500 MHz, 30° C.), and HRMS (ESI, (M+H)$^+$) data.

Preparation 11: preparation of N$^2$-((1E)-2-((2,6-bis(1-methylethyl)phenyl)amino)-2-cyclohexen-1-ylidene)-N$^1$,N$^1$-dimethyl-1,2-ethanediamine (H) is hereby incorporated by reference from Example H of U.S. nonprovisional patent application Ser. No. 12/544,581, filed Aug. 20, 2009, and repeated here.

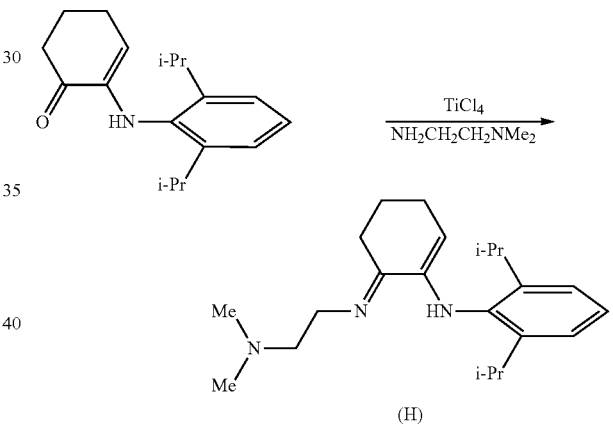

(H)

Day 1: Charge a vial with N,N-dimethylethylenediamine (0.58 mL, 5.3098 mmol) and toluene (7.0 mL). To the colorless solution add a solution of titanium(IV) chloride (0.1001 g, 0.5276 mmol) in toluene (3.0 mL). Red solids are observed but then dissolve in solution when strong stirring is applied. Stir the resulting orange solution for 1 hour. Then, add a solution of 2-(2,6-diisopropylphenylamino)-2-cyclohexen-1-one (0.2437 g, 0.8979 mmol, Preparation 3) in toluene (2.0 mL). Rinse the vial that contained the solution with toluene (1.0 mL), and add the rinse to the reaction mixture.

Day 2. Separately prepare a stock solution of the titanium reagent (to have a ratio of 1:1.4, titanium to keto-enamine) by charging a vial with N,N-dimethylethylenediamine (0.58 mL, 5.3098 mmol) and toluene (7.0 mL). To the colorless solution add a solution of titanium(IV)chloride (0.1000 g, 0.5271 mmol) in toluene (3.0 mL). Red solids are observed, but dissolve in solution when strong stirring is applied. Stir the resulting orange solution for 1 hour.

After stirring reaction mixture from Day 1 overnight, add to the reaction mixture 3.3 mL of the stock solution (prepared as described above) of the titanium reagent. Stir the resulting mixture for 3 hours. Filter the mixture (syringe filter), using hexanes to wash the solids. Concentrate the yellow filtrate solution in vacuo to afford a yellow oil. Dissolve the oil in hexanes (10 mL) to precipitate solids. Filter the mixture (syringe filter) and wash the solids with two 5-mL portions of hexanes. Concentrate the yellow filtrate solution in vacuo to afford 0.2790 g (90.97%) of the product (H) as a yellow oil.

$^1$H NMR ($C_6D_6$, 500 MHz, 30° C.) δ 7.24-7.18 (m, 3H, i-$Pr_2$-Ph), 6.85 (s, 1H, NH), 4.80 (t, 1H, J=4.4 Hz, H5), 3.49-3.38 (m, 4H, CH($CH_3$)$_2$) and NCH$_2$CH$_2$N), 2.67 (t, 2H, J=7.1 Hz, NCH$_2$CH$_2$N), 2.19 (s, 6H, N(CH$_3$)$_2$), 2.07 (t, 2H, J=6.4 Hz, H2), 1.94 (q, 2H, J=5.4 Hz, H4), 1.49 (quintet, 2H, J=6.2 Hz, H3), 1.23 (d, 12H, J=6.7 Hz, CH(CH$_3$)$_2$).

Not shown are $^{13}$C NMR ($C_6D_6$, 125 MHz, 30° C.) data.

Preparation 12: preparation of (6E)-6-(butylimino)-N-(1,1':3',1''-terphenyl)-2'-yl-1-cyclohexen-1-amine (J) is hereby incorporated by reference from Example J of U.S. nonprovisional patent application Ser. No. 12/544,581, filed Aug. 20, 2009, and repeated here.

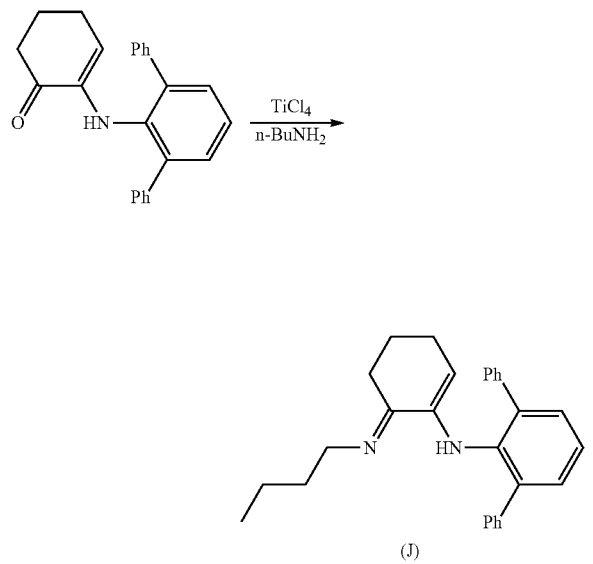

Follow a procedure similar to that of Preparation 2 except use n-butylamine (0.53 mL, 5.3406 mmol); toluene (7.0 mL); a solution of titanium(IV)chloride (0.1006 g, 0.5303 mmol) in toluene (3.0 mL); stir the resulting solution for 1 hour; then add a solution of 2-((1,1':3',1''-terphenyl)-2'-ylamino)-2-cyclohexen-1-one (0.3062 g, 0.9021 mmol, Preparation 6) in toluene (2.0 mL); toluene rinse (1.0 mL); to afford after isolation 0.3352 g (94.18%) of the product (J) as a brown oil.

$^1$H NMR ($C_6D_6$, 500 MHz, 30° C.) δ 7.50 (d, 4H, J=7.7 Hz, Ph), 7.29 (d, 2H, J=7.6 Hz, Ph), 7.17 (t, 4H, J=7.7 Hz, Ph), 7.10-7.06 (m, 3H, Ph), 6.98 (s, 1H, NH), 4.91 (t, 1H, J=4.6 Hz, H5), 2.99 (t, 2H, J=6.6 Hz, H7), 1.77 (t, 2H, J=6.5 Hz, H2), 1.73 (q, 2H, J=5.4 Hz, H4), 1.46 (quintet, 2H, J=7.1 Hz, H8), 1.23 (sextet, 2H, J=7.5 Hz, H9), 1.16 (quintet, 2H, J=6.1 Hz, H3), 0.88 (t, 3H, J=7.4 Hz, H10).

Preparation 13: preparation of (E)-2,6-diisopropyl-N-(2-(butylamino)cyclohex-2-enylidene)aniline (L) is hereby incorporated by reference from Example L of U.S. nonprovisional patent application Ser. No. 12/544,581, filed Aug. 20, 2009, and repeated here.

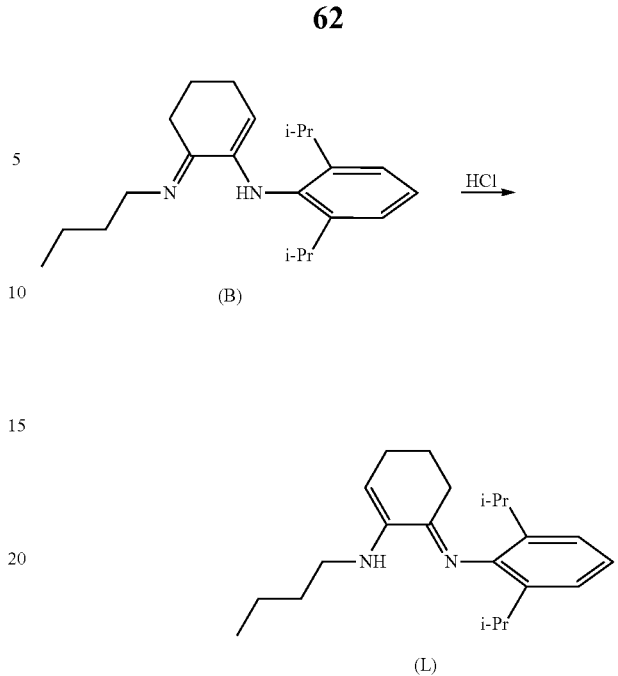

Charge a vial with N-((6E)-6-(butylimino)-1-cyclohexen-1-yl)-2,6-bis(1-methylethyl)-benzenamine (B) (3.0038 g, 9.1995 mmol, Preparation 7) and toluene (30.0 mL). Stir the resulting yellow solution and add a solution of 1.0M HCl (aqueous, 0.46 mL, 0.46 mmol) in diethyl ether. Stir the resulting reaction mixture for 3 hours. To the mixture add hexanes (5 mL) and filter (syringe filter) to remove fine solids. Wash the filtered solids with hexanes (6 mL), and concentrate the filtrate overnight under reduced pressure to give 3.0107 g of the product (L)d as a thick brown oil.

$^1$H NMR ($C_6D_6$, 500 MHz, 30° C.): 7.144 (d, 1H, $^3J_{H-H}$=8 Hz, i-$Pr_2$-Ph), 7.143 (d, 1H, $^3J_{H-H}$=7 Hz, i-$Pr_2$-Ph), 7.09 (dd, 1H, $^3J_{H-H}$=8.8 Hz, $^3J_{H-H}$=6.5 Hz, i-$Pr_2$-Ph), 5.11 (br. s, 1H, NH), 5.04 (t, 1H, $^3J_{H-H}$=4 Hz, H2), 2.886 (t, 2H, $^3J_{H-H}$=7 Hz, H7), 2.881 (sept. 2H, $^3J_{H-H}$=6.9 Hz, CH($CH_3$)$_2$), 2.16 (q, 2H, $^3J_{H-H}$=5.5 Hz, H3), 2.07 (m, 2H, H5), 1.53 (p, 2H, $^3J_{H-H}$=6.5 Hz, H3), 1.43 (pm, 2H, $^3J_{H-H}$=7.8 Hz, H8), 1.28 (sex-m, 2H, $^3J_{H-H}$=7.8 Hz, H9), 1.16 (d, 6H, $^3J_{H-H}$=6.9 Hz, CH($CH_3$)$_2$), 1.13 (d, 6H, $^3J_{H-H}$=6.9 Hz, CH($CH_3$)$_2$), 0.80 (t, 3H, $^3J_{H-H}$=7.4 Hz, H10).

Not shown are $^{13}$C NMR ($C_6D_6$, 125 MHz, 30° C.) data.

Preparation 14: preparation of Metal-ligand Complex (a1), [N-[2-[[2,6-bis(1-methylethyl)phenyl]amino-kappaN]-2-cyclohexen-1-ylidene]-2,6-bis(1-methylethyl)benzenaminato-kappaN]tris(phenylmethyl)-hafnium (a1) is hereby incorporated by reference from Example 1 of U.S. nonprovisional patent application Ser. No. 12/544,581, filed Aug. 20, 2009, and repeated here.

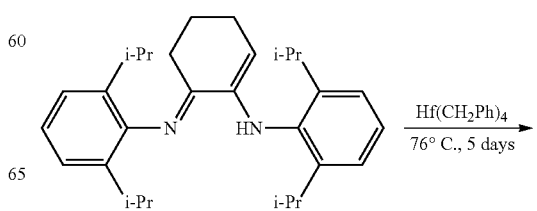

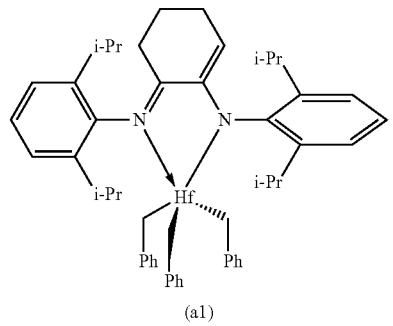

(a1)

(E)-N-(2-(2,6-diisopropylphenylamino)cyclohex-2-enylidene)-2,6-diisopropylaniline (0.439 g, 1.0 mmol; Preparation 1) and tetrabenzyl hafnium (0.554 g, 1.0 mmol) are dissolved in 6 mL of $C_6D_6$. Solution is heated for 4 days at 76° C. NMR showed complete conversion of HfBn$_4$ with product to ligand ration of 9:1. Solvent is removed under reduced pressure. The residue is dissolved in 3 mL of toluene and filtered. To the filtrate is added 8 mL of hexane. Within minutes yellow crystals appeared. After standing at ambient temperature for 3 hours, 10 mL of hexane are added and solution is put into freezer (−26° C.) overnight. Solvent is decanted and yellow crystals are washed with hexane (2×10 mL) and then dried under reduced pressure to give 0.486 mg of Metal-ligand Complex (a1). Yield 54%.

$^1$H NMR ($C_6D_6$, 500 MHz, 30° C.): 7.25 (m, 3H, iPr$_2$-Ph), 7.11 (tm, 6H, $^3J_{H-H}$=7.5 Hz, meta-CH$_2$Ph), 7.06 (m, 3H, iPr$_2$-Ph), 6.84, (m, 3H, $^3J_{H-H}$=7.5 Hz, para-CH$_2$Ph), 6.61 (d, 6H, $^3J_{H-H}$=7.5 Hz, ortho-CH$_2$Ph), 4.96 (t, 1H, $^3J_{H-H}$=5.0 Hz, H5), 3.51 (sept. 2H, $^3J_{H-H}$=7.0 Hz, CH(CH$_3$)$_2$), 2.74 (sept. 2H, $^3J_{H-H}$=7.0 Hz, CH(CH$_3$)$_2$), 2.11 (br. s. 6H, Hf—CH$_2$Ph), 1.98 (t, 2H, $^3J_{H-H}$=6.5 Hz, H2), 1.81 (q, 2H, $^3J_{H-H}$=5.6 Hz, H4), 1.25 (p, 2H, $^3J_{H-H}$=6.0, H3), 1.22 (d, 6H, $^3J_{H-H}$=7.0 Hz, CH(CH$_3$)$_2$), 1.16 (d, 6H, $^3J_{H-H}$=6.5 Hz, CH(CH$_3$)$_2$), 1.14 (d, 6H, $^3J_{H-H}$=6.5 Hz, CH(CH$_3$)$_2$), 0.98 (d, 6H, $^3J_{H-H}$=7.0 Hz, CH(CH$_3$)$_2$).

Anal. Calcd for $C_{51}H_{62}HfN_2$: C, 69.49; H, 7.09; N, 3.18. Found: C, 69.36; H, 6.96, N, 3.06.

Not shown is an ORTEP depiction of a single crystal structure derived by x-ray analysis.

Preparation 15: preparation of Metal-ligand Complex (B1), (N-((6E)-6-(butylimino-kappaN)-1-cyclohexen-1-yl)-2,6-bis(1-methylethyl)benzenaminato-kappaN)tris(phenylmethyl)-hafnium is hereby incorporated by reference from Example 3 of U.S. nonprovisional patent application Ser. No. 12/544,581, filed Aug. 20, 2009, and repeated here.

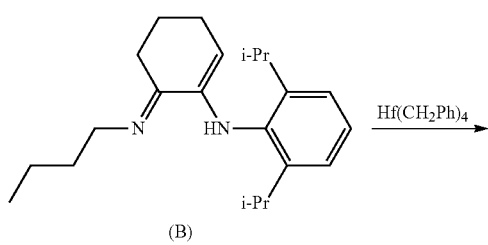

(B)

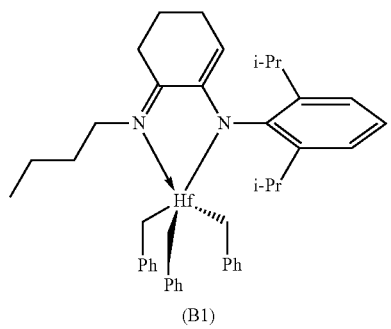

(B1)

The (E)-N-(6-(butylimino)cyclohex-1-enyl)-2,6-diisopropylaniline (0.3005, 0.92 mmol; (B); Preparation 7) and tetrabenzyl hafnium (0.4997 mmol) are dissolved in 6 mL of toluene at room temperature giving light red solution. After stirring overnight (yellow solution), solvent is removed under reduced pressure giving highly crystalline yellow solid. The residue is dissolved in 2 mL of toluene followed by addition of 8 mL of hexane. Solution is filtered and put aside overnight at room temperature resulting in formation of large yellow crystals. Solution is decanted and large yellow crystals are washed with cold hexane (5 mL) and then dried under reduced pressure to give 331 mg of Metal-ligand Complex (B1). Solution and hexane wash are combined and put into freezer (−20° C.) overnight. Solvent is decanted and yellow crystals are washed with 2×2 mL of cold hexane and then dried under reduced pressure give additional 211 mg of Metal-ligand Complex (B1). Combined yield of Metal-ligand Complex (B1) is 0.542 mg, 75.8%.

$^1$H NMR (toluene-d$_8$, 500 MHz, 30° C.): 7.18 (s, 3H, iPr$_2$-Ph), 7.11 (tm, 6H, $^3J_{H-H}$=7.6 Hz, meta-CH$_2$Ph), 6.81, (m, 9H, ortho-para-CH$_2$Ph), 4.57 (t, 1H, $^3J_{H-H}$=5.0 Hz, H5), 3.24 (sept. 2H, $^3J_{H-H}$=6.6 Hz, CH(CH$_3$)$_2$), 2.80 (m, 2H, H7), 2.11 (br. s. 6H, Hf—CH$_2$Ph), 1.89 (t, 2H, $^3J_{H-H}$=6.7 Hz, H2), 1.83 (q, 2H, $^3J_{H-H}$=5.6 Hz, H4), 1.31 (d, 6H, $^3J_{H-H}$=6.9 Hz, CH(CH$_3$)$_2$), 1.29 (p, 2H, $^3J_{H-H}$=6.3, H3), 1.17 (m, 2H, H8), 1.11 (d, 6H, $^3J_{H-H}$=6.9, CH(CH$_3$)$_2$), 1.06 (sex., 2H, $^3J_{H-H}$=7.4, H9), 0.77 (t, 3H, $^3J_{H-H}$=6.9, H10).

Anal. Calcd for $C_{43}H_{54}HfN_2$: C, 66.43; H, 7.00; N, 3.60. Found: C, 66.58; H, 6.89, N, 3.65.

Thermolysis study of Metal-ligand Complex (B1). Metal-ligand Complex (B1) (25 mg) is dissolved in 0.6 mL of toluene-d$_8$. Solution is heated for 42 hours at 89.3° C. After this time NMR spectrum showed about 4% decomposition.

Not shown is an ORTEP depiction of a single crystal structure derived by x-ray analysis.

Preparation 16: preparation of Metal-ligand Complex (B2), (N-((6E)-6-(butylimino-kappaN)-1-cyclohexen-1-yl)-2,6-bis(1-methylethyl)benzenaminato-kappaN)tris(phenylmethyl)-zirconium is hereby incorporated by reference from Example 4 of U.S. nonprovisional patent application Ser. No. 12/544,581, filed Aug. 20, 2009, and repeated here.

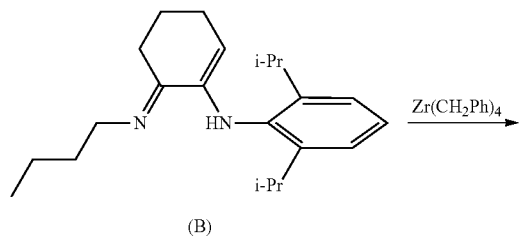

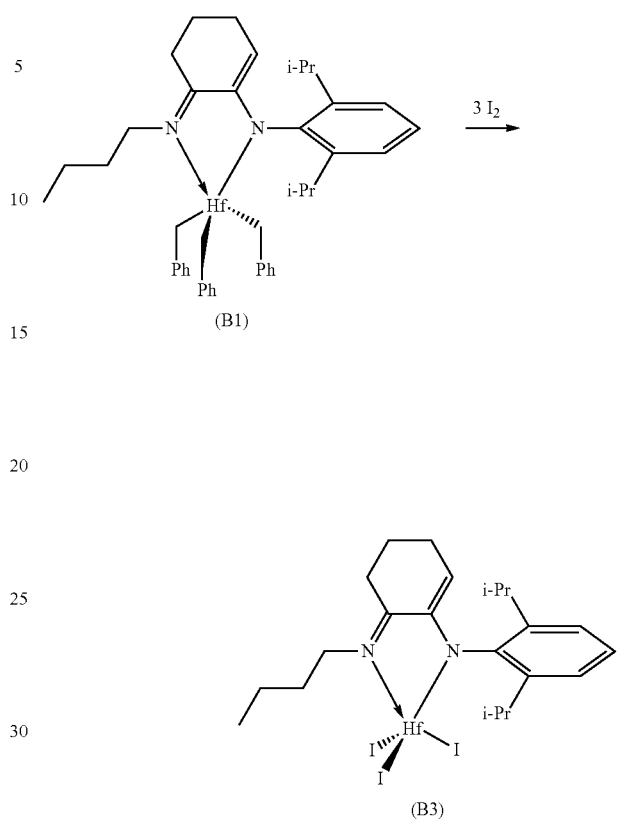

The (E)-N-(6-(butylimino)cyclohex-1-enyl)-2,6-diisopropylaniline (0.35 g, 1.07 mmol; (B); Preparation 7) and tetrabenzyl zirconium (0.4885 g, 1.07 mmol) are dissolved in 3 mL of $C_6D_6$ at room temperature giving light red solution. After stirring for 1 hour, proton NMR is taken showing complete reaction taken place. Contents of the NMR tube are returned to reaction mixture. To the reaction mixture are added 8 mL of hexane, solution is filtered and put into freezer (−45° C.) overnight. Solvent is decanted and yellow crystals are washed with cold hexane (2×4 mL) and then dried under reduced pressure to give 0.566 g of Metal-ligand Complex (B2). Yield 68%.

$^1$H NMR ($C_6D_6$, 500 MHz, 30° C.): 7.22 (pseudo-triplet, 3H, iPr$_2$-Ph), 7.12 (tm, 6H, $^3J_{H-H}$=7.8 Hz, ortho-CH$_2$Ph), 6.88 (tm, 3H, $^3J_{H-H}$=7.0 Hz, para-CH$_2$Ph), 6.88 (dm, 6H, $^3J_{H-H}$=8.0 Hz, ortho-CH$_2$Ph), 4.64 (t, 1H, $^3J_{H-H}$=5.0 Hz, H5), 3.30 (sept. 2H, $^3J_{H-H}$=7.0 Hz, CH(CH$_3$)$_2$), 2.83 (m, 2H, H7), 2.24 (br. s. 6H, Hf—CH$_2$Ph), 1.95 (t, 2H, $^3J_{H-H}$=6.3 Hz, H2), 1.78 (q, 2H, $^3J_{H-H}$=5.8 Hz, H4), 1.32 (d, 6H, $^3J_{H-H}$=6.5 Hz, CH(CH$_3$)$_2$), 1.28 (p, 2H, $^3J_{H-H}$=6.5, H3), 1.21 (m, 2H, H8), 1.14 (d, 6H, $^3J_{H-H}$=6.5, CH(CH$_3$)$_2$), 1.05 (sex., 2H, $^3J_{H-H}$=7.5, H9), 0.73 (t, 3H, $^3H_{H-H}$=7.5, H10).

Anal. Calcd for $C_{43}H_{54}ZrN_2$: C, 74.84; H, 7.89; N, 4.06. Found: C, 74.60; H, 7.73, N, 4.28.

Not shown is an ORTEP depiction of a single crystal structure derived by x-ray analysis.

Preparation 17: preparation of Metal-ligand Complex (B3): (N-((6E)-6-(butylimino-kappaN)-1-cyclohexen-1-yl)-2,6-bis(1-methylethyl)benzenaminato-kappaN)triiodohafnium is hereby incorporated by reference from Example 13 of U.S. nonprovisional patent application Ser. No. 12/544,581, filed Aug. 20, 2009, and repeated here.

To 1.5624 g (2.01 mmol) of (N-((6E)-6-(butylimino-kappaN)-1-cyclohexen-1-yl)-2,6-bis(1-methylethyl)benzenaminato-kappaN)tris(phenylmethyl)-hafnium (Metal-ligand Complex (B1) of Preparation 15) dissolved in 20 mL of $CH_2Cl_2$ at room temperature is added within 20 minutes iodine (I$_2$) dissolved in 60 mL of $CH_2Cl_2$. After stirring for 10 minutes at room temperature, solvent is removed under reduced pressure. To the resulting residue is added 30 mL of hexane, and the resulting suspension is stirred for 15 minutes. The suspension is filtered with a frit, the filtercake is washed with 15 mL of hexane and dried under reduced pressure to give 1.47 g of yellow Metal-ligand Complex (B3) (82.7% yield).

$^1$H NMR ($C_6D_6$, 500 MHz, 30° C.): 7.24 (m, 1H, iPr$_2$-para-Ph), 7.17 (m, 2H, iPr$_2$-meta-Ph), 4.72 (t, 1H, $^3J_{H-H}$=4.9 Hz, H5), 3.59 (m, 2H, H7), 3.56 (sept. 2H, $^3J_{H-H}$=6.8 Hz, CH(CH$_3$)$_2$), 1.68 (q, 2H, $^3J_{H-H}$=5.7 Hz, H4), 1.66 (t, 2H, $^3J_{H-H}$=6.4 Hz, H2), 1.61 (d, 6H, $^3J_{H-H}$=6.9 Hz, CH(CH$_3$)$_2$), 1.58 (m, 2H, H8), 1.11 (d, 6H, $^3J_{H-H}$=6.8 Hz, CH(CH$_3$)$_2$), 1.10 (sex., 2H, $^3J_{H-H}$=7.1 Hz, H9), 1.07 (p, 2H, $^3J_{H-H}$=6.0 Hz, H3), 0.79 (t, 3H, $^3J_{H-H}$=7.4 Hz, H10). Information about the chemical shift, multiplicity and coupling constants for H3 and H9 is obtained from TOCSY1D spectra.

Preparation 18: preparation of Metal-ligand Complex (B4): (N-((6E)-6-(butylimino-kappaN)-1-cyclohexen-1-yl)-2,6-bis(1-methylethyl)benzenaminato-kappaN)trimethylhafnium is hereby incorporated by reference from Example 14 of U.S. nonprovisional patent application Ser. No. 12/544,581, filed Aug. 20, 2009, and repeated here.

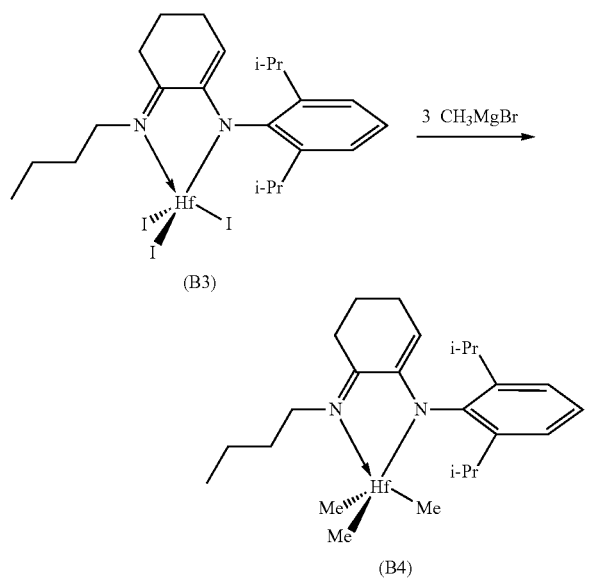

(B3)

(B4)

To a 30 mL toluene solution containing 0.7486 g (0.85 mmol) of (N-((6E)-6-(butylimino-kappaN)-1-cyclohexen-1-yl)-2,6-bis(1-methylethyl)benzenaminato-kappaN)triiodohafnium (Metal-ligand Complex (B3) of Preparation 17) is added 0.88 mL (2.65 mmol) of 3 molar (M) methyl magnesium bromide (CH$_3$MgBr) solution in diethyl ether. The resulting reaction mixture is stirred for 20 minutes, then solvent is removed under reduced pressure. The resulting residue is extracted with 30 mL of hexane and filtered. Solvent is removed from the filtrate to give 0.462 g (99.4% yield) of Metal-ligand Complex (B4) as yellow crystalline solid.

Preparation 19: preparation of Metal-ligand Complex (B4), (N-((6E)-6-(butylimino-kappaN)-1-cyclohexen-1-yl)-2,6-bis(1-methylethyl)benzenaminato-kappaN)trimethylhafnium is hereby incorporated by reference from Example 15 of U.S. nonprovisional patent application Ser. No. 12/544,581, filed Aug. 20, 2009, and repeated here.

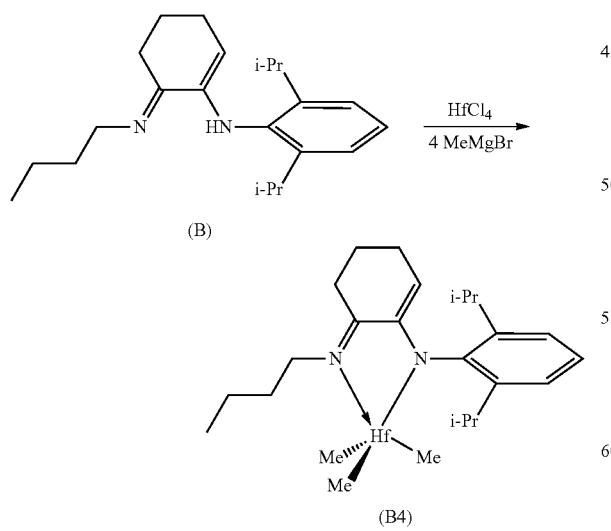

(B)

(B4)

To a cold (−25° C.) toluene solution (50 mL) of N-fi6E)-6-(butylimino)-1-cyclohexen-1-yl)-2,6-bis(1-methylethyl)-benzenamine (3.03, 9.28 mol; (B); Preparation 8) and HfCl$_4$ (2.972 g, 9.28 mmol) is added 12.68 mL of 3 M CH$_3$MgBr ether solution. During addition of CH$_3$MgBr gas evolution is observed. The resulting reaction mixture does not get warm. Within minutes, reaction mixture changed color from yellow to black. Solution is stirred for 1 hour. Solvent is removed under reduced pressure. To the residue is added 50 mL of hexane and the resulting yellow solution is filtered. The filtercake (salts) is washed with additional 30 mL of hexane. Solvent is removed under reduced pressure to give 4.03 g (79.1% yield) of Metal-ligand Complex (B4) as a yellow solid.

$^1$H NMR (C$_6$D$_6$, 500 MHz, 30° C.): 7.19-7.24 (m, 3H, iPr$_2$-Ph), 4.66 (t, 1H, $^3J_{H-H}$=4.9 Hz, H5), 3.64 (sept. 2H, $^3J_{H-H}$=7.0 Hz, CH(CH$_3$)$_2$), 3.34 (m, 2H, H7), 1.89 (t, 2H, $^3J_{H-H}$=6.6 Hz, H2), 1.88 (q, 2H, $^3J_{H-H}$=5.5 Hz, H4), 1.42 (d, 6H, $^3J_{H-H}$=7.0 Hz, CH(CH$_3$)$_2$), 1.34 (m, 2H, H8), 1.28 (p, 2H, $^3J_{H-H}$=6.2 Hz, H3), 1.21 (d, 6H, $^3J_{H-H}$=6.9 Hz, CH(CH$_3$)$_2$), 1.08 (sex., 2H, $^3J_{H-H}$=7.5 Hz, H9), 0.77 (t, 3H, $^3J_{H-H}$=7.4 Hz, H10), 0.50 (s, 9H, Hf—CH$_3$).

$^{13}$C{$^1$H} NMR (C$_6$D$_6$, 125 MHz, 30° C.): 175.30 (N=C), 152.07 (quat.), 144.98 (quat.), 144.31 (quat.), 126.07 (iPr$_2$-para-Ph), 124.16 (iPr$_2$-meta-Ph), 114.71 (C5), 60.40 (Hf—CH$_3$), 49.57 (C7), 31.00 (C8), 28.48 (CH(CH$_3$)$_2$), 28.00 (C2), 26.00 (CH(CH$_3$)$_2$), 24.69 (C4), 24.53 (CH(CH$_3$)$_2$), 23.12 (C3), 21.00 (C9), 13.82 (C10).

HSQC (C$_6$D$_6$), 500 MHz, 30° C.): (7.19-7.24, 126.07, 124.16), (4.66, 114.71), (3.64, 28.48), (3.34, 49.57), (1.89, 28.00), (1.88, 24.69), (1.42, 24.53), (1.34, 31.00), (1.28, 23.12), (1.21, 26.00), (1.08, 21.00), (0.77, 13.82), (0.50, 60.40).

Not shown is an ORTEP depiction of a single crystal structure derived by x-ray analysis.

Preparation 20: preparation of Metal-ligand Complex (D1): [N-(2,6-diisopropylphenyl)-2-butylaminotroponiminato]tribenzylhafnium is hereby incorporated by reference from Example 16 of U.S. nonprovisional patent application Ser. No. 12/544,581, filed Aug. 20, 2009, and repeated here.

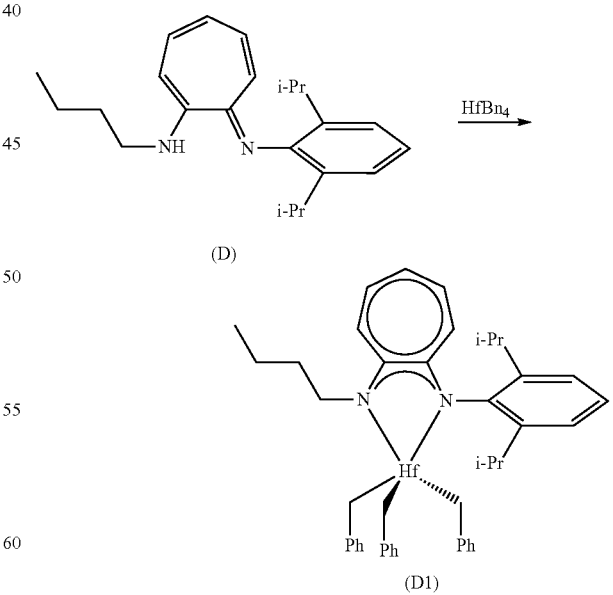

(D)

(D1)

N-(2,6-Diisopropylphenyl)-2-butylaminotroponimine ((D); Preparation 9, 250 mg, 0.74 mmol) and HfBn$_4$ (403 mg, 0.74 mmol) are dissolved in dry C$_6$D$_6$ (3 mL) giving an orange solution, which is stirred at 25° C. Completion of the reaction is confirmed by $^1$H NMR taken after 90 minutes. The reaction mixture is concentrated under vacuum, layered with hexane and cooled to −45° C. overnight. The resulting yellow crystals are filtered, washed with cold hexane and dried under vacuum to give 557 mg (79% yield) of Metal-ligand Complex (D1).

$^1$H NMR (C$_6$D$_6$, 500 MHz, 30° C.): 7.21 (m, 3H, H10, H11, H12), 7.15 (tm, J$_{H-H}$=7.5 Hz, 6H, meta-CH$_2$Ph), 6.91 (dm, J$_{H-H}$=6.1 Hz, 6H, ortho-CH$_2$Ph), 6.85 (m, 3H, para-CH$_2$Ph), 6.85 (m, 1H, H5), 6.59 (d, J$_{H-H}$=11.2 Hz, 1H, H6), 6.50 (m, 1H, H2), 6.48 (m, 1H, H3), 6.25 (t, J$_{H-H}$=8.8 Hz, 1H, H4), 3.18 (m, 2H, H14), 2.79 (septet, H$_{H-H}$=6.8 Hz, 2H, CH(CH$_3$)$_2$), 2.21 (br s, 6H, CH$_2$Ph), 1.38 (m, 2H, H15), 1.26 (d, J$_{H-H}$=6.8 Hz, 6H, CH(CH$_3$)$_2$), 1.14 (sextet, J$_{H-H}$=7.5 Hz, 2H, H16), 0.94 (d, J$_{H-H}$=6.8 Hz, 6H, CH(CH$_3$)$_2$), 0.77 (t, J$_{H-H}$=7.3 Hz, 6H, H17).

Anal. Calcd for C$_{44}$H$_{52}$HfN$_2$: C, 67.12; H, 6.66; N, 3.56. Found: C, 66.40; H, 6.60; N, 3.65.

Not shown is an ORTEP depiction of a single crystal structure derived by x-ray analysis.

Preparation 21: preparation of Metal-ligand Complex (G1), (E)-N-(5-(butylimino-κN)-2,4-dimethylcyclopent-1-enyl)-2,6-bis(1-methylethyl)benzenaminato-κN)tris(phenylmethyl)-hafnium is hereby incorporated by reference from Example 21 of U.S. nonprovisional patent application Ser. No. 12/544,581, filed Aug. 20, 2009, and repeated here.

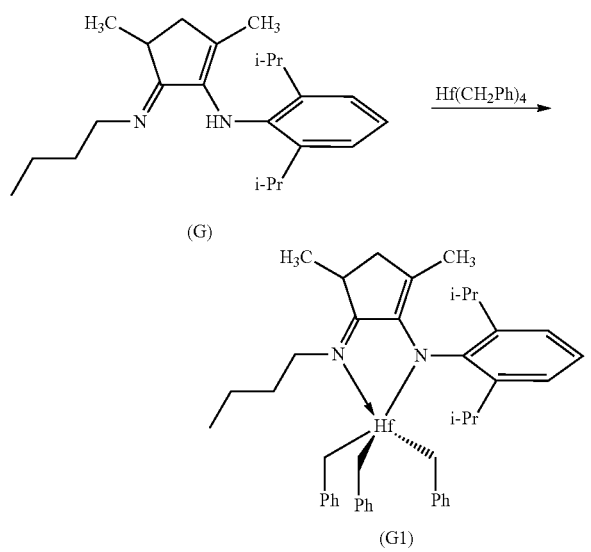

In the glove box, a vial is charged with 410 mg (1.2 mmol) of (E)-N-(5-(butylimino-2,4-dimethylcyclopent-1-enyl)-2,6-diisopropylaniline ((G); Preparation 10); in 8 mL of toluene; add 654 mg (1.2 mmol) of Hf(CH$_2$Ph)$_4$; stir the resulting reaction mixture for 2 hours (do not add additional ligand); concentrate the reaction mixture under reduced pressure to give a residue; dissolve residue in and crystallize from 3 mL of toluene and 20 mL of hexane to give 0.335 mg of Metal-ligand Complex (G1). Yield 35%. Grow X-ray quality crystals from toluene/hexane solvent mixture.

$^1$H NMR (C$_6$D$_6$, 500 MHz, 30° C.) δ 7.15 (m, 9H, i-Pr$_2$-Ph and meta-CH$_2$Ph), 6.93 (d, 6H, $^3$J=7.4 Hz, ortho-CH$_2$Ph), 6.86 (t, 3H, $^3$J=7.3 Hz, para-CH$_2$Ph), 3.53 (sep. 1H, $^3$J=6.9 Hz, (CH$_3$)$_2$CH), 3.23 (sep. 1H, $^3$J=6.9 Hz, (CH$_3$)$_2$CH), 3.08 (pd, 2H, $^2$J=12.5 Hz, $^3$J=5 Hz, H6), 2.45 (ddd, 1H, $^2$J=17.5 Hz, $^3$J=6 Hz, $^4$J=1.6 Hz, H3), 2.34 (p, 1H, $^3$J=6.8 Hz, H2), 2.26 (d, 3H, $^3$J=11.8 Hz, CH$_2$Ph), 2.21 (d, 3H, $^3$J=12 Hz, CH$_2$Ph), 1.61 (d, 1H, $^3$J=17.5 Hz, H3), 1.44 (m, 1H, H7), 1.29 (d, 3H, $^3$J=6.9 Hz, (CH$_3$)$_2$CH)), 1.27 (d, 3H, $^3$J=6.9 Hz, (CH$_3$)$_2$CH), 1.23 (m, 1H, H7), 1.14 (d, 3H, $^3$J=6.9 Hz, (CH$_3$)$_2$CH), 1.06 (m, 2H, H8), 1.05 (d, 3H, $^3$J=6.7 Hz, (CH$_3$)$_2$CH), 0.94 (s, 3H, CH$_3$), 0.81 (d, 3H, $^3$J=7 Hz, CH$_3$), 0.76 (t, 3H, $^3$J=7.4 Hz, H9).

Not shown are $^{13}$C NMR (C$_6$D$_6$, 125 MHz, 30° C.) and HSQCAD (C$_6$D$_6$, 500 MHz, 30° C.) data and an ORTEP depiction of a single crystal structure derived by x-ray analysis.

Preparation 22: preparation of Metal-ligand Complex (H1), (N$^2$-(2-((2,6-bis(1-methylethyl)phenyl)amino-κN)-2-cyclohexen-1-ylidene)-N$^1$,N$^1$-dimethyl-1,2-ethanediaminato-κN,κN')tris(phenylmethyl)-hafnium is hereby incorporated by reference from Example 22 of U.S. nonprovisional patent application Ser. No. 12/544,581, filed Aug. 20, 2009, and repeated here.

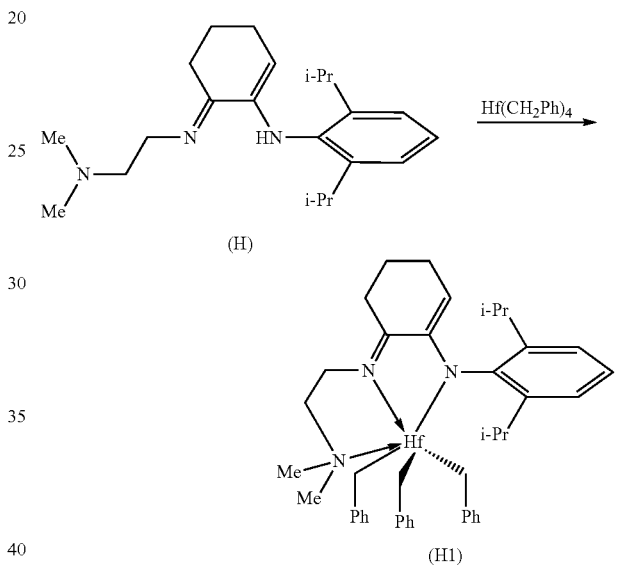

Follow a procedure similar to that of Preparation 21 except use N$^2$-((1E)-2-((2,6-bis(1-methylethyl)phenyl)amino)-2-cyclohexen-1-ylidene)-N$^1$,N$^1$-dimethyl-1,2-ethanediamine (H) (0.2584 g, 0.7566 mmol; Preparation 11); toluene (3 mL); a yellow solution of hafnium tetrabenzyl (0.4103 g, 0.7556 mmol) in toluene (2 mL); toluene rinse (1 mL); and stir reaction mixture for 30 minutes; crystallize from 3 mL of toluene and 17 mL of hexane to give 235 mg of Metal-ligand Complex (H1). Yield 39.3%.

$^1$H NMR (C$_6$D$_6$, 500 MHz, 30° C.) δ 7.30-7.23 (m, 3H, i-Pr$_2$-Ph), 7.14 (t, 6H, J=7.6 Hz, meta-CH$_2$Ph), 6.93 (d, 6H, J=7.5 Hz, ortho-CH$_2$Ph), 6.81 (t, 3H, J=7.3 Hz, para-CH$_2$Ph), 4.86 (t, 1H, J=5.0 Hz, H5), 4.07 (septet, 2H, J=6.8 Hz, CH(CH$_3$)$_2$), 2.19 (t, 2H, J=6.0 Hz, H7), 2.10 (broad s, 6H, CH$_2$Ph), 2.06 (s, 6H, N(CH$_3$)$_2$), 2.02 (q, 2H, J=5.6 Hz, H4), 1.81-1.77 (m, 4H, H8 and H2), 1.46 (quintet, 2H, J=6.4 Hz, H3), 1.44 (d, 6H, J=6.8 Hz, CH(CH$_3$)$_2$), 1.24 (d, 6H, J=6.7 Hz, CH(CH$_3$)$_2$).

Not shown are $^{13}$C NMR (C$_6$D$_6$, 125 MHz, 30° C.), HSQCAD (C$_6$D$_6$, 500 MHz, 30° C.), and elemental analysis (C, H, N) data and an ORTEP depiction of a single crystal structure derived by x-ray analysis.

Preparation 23: preparation of Metal-ligand Complex (J1), (6-(butylimino-κN)—N-(1,1':3',1''-terphenyl)-2'-yl-1-cyclohexen-1-aminato-κN)tris(phenylmethyl)-hafnium is hereby incorporated by reference from Example 23 of U.S. nonprovisional patent application Ser. No. 12/544,581, filed Aug. 20, 2009, and repeated here.

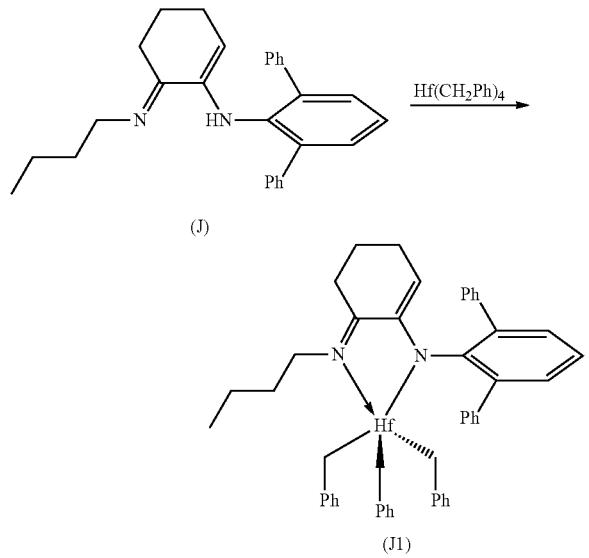

Follow a procedure similar to that of Preparation 21 except use (6E)-6-(butylimino)-N-(1,1':3',1''-terphenyl)-2'-yl-1-cyclohexen-1-amine (J) (0.2972 g, 0.7533 mmol; Preparation 12) (no additional (J) added); toluene (3 mL); a solution of hafnium tetrabenzyl (0.4098 g, 0.7547 mmol) in toluene (2 mL); toluene rinse (1 mL); stir the resulting reaction mixture for 20 minutes; then add hexanes (2 mL); dissolve isolated residue in 2 mL of toluene, add 10 mL of hexane; filter, and concentrate to give 350 mg of Metal-ligand Complex (J1) as yellow thick oil. Yield 55.0%.

$^1$H NMR (C$_6$D$_6$, 500 MHz, 30° C.) δ 7.47-7.45 (m, 4H, Ph), 7.37 (d, 2H, J=7.7 Hz, Ph), 7.21 (t, 4H, J=7.7 Hz, Ph), 7.16 (t, 2H, J=7.6 Hz, Ph), 7.11-7.08 (m, 7H, Ph), 6.80 (t, 3H, J=7.4 Hz, Ph), 6.63 (broad d, 6H, J=7.3 Hz, Ph), 4.95 (t, 1H, J=5.0 Hz, H5), 2.30-2.27 (m, 2H, H7), 1.92 (broad s, 6H, CH$_2$Ph), 1.86 (q, 2H, J=5.6 Hz, H4), 1.63 (t, 2H, J=6.4 Hz, H2), 1.11 (quintet, 2H, J=6.2 Hz, H3), 0.98-0.90 (m, 4H, H8 and H9), 0.68 (t, 3H, J=7.0 Hz, H10).

Not shown are $^{13}$C NMR (C$_6$D$_6$, 125 MHz, 30° C.) and HSQCAD (C$_6$D$_6$, 500 MHz, 30° C.) data.

Preparation 24: preparation of Metal-ligand Complex (L1), (2,6-bis(1-methylethyl)-N-((1E)-2-(butylamino-κN)-2-cyclohexen-1-ylidene)benzenaminato-κN)trimethylhafnium is hereby incorporated by reference from Example 26 of U.S. nonprovisional patent application Ser. No. 12/544,581, filed Aug. 20, 2009, and repeated here.

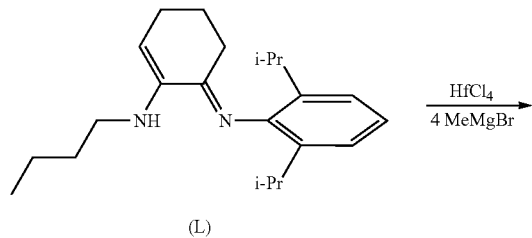

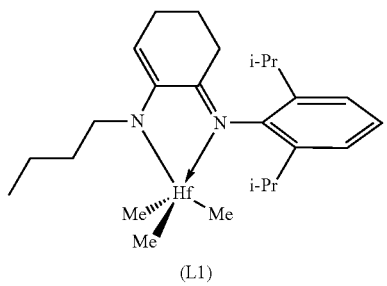

To a 40 mL of toluene solution containing 1.0168 g (3.11 mmol) (E)-2,6-diisopropyl-N-(2-(butylamino)cyclohex-2-enylidene)aniline (L) (Preparation 13) and 0.997 g (3.11 mmol) of HfCl$_4$ add 4 mole equivalents of a 3M MeMgBr ether solution. During addition of MeMgBr gas evolution is observed. After stirring the resulting reaction mixture for 2 hours at room temperature, remove solvent under reduced pressure. To the residue add 20 mL of toluene followed by 20 mL of hexane, and filter the resulting yellow solution. Remove solvent from the filtrate under reduced pressure leaving yellow crystalline solid. NMR shows formation of the desired product (L1) and a small amount of impurities. Dissolve the solid in 2 mL of warm toluene and add 18 mL of hexane. Filter the resulting solution, and place filtrate into freezer (−26° C.) overnight. Collect precipitated yellow solid on a sintered glass funnel, wash it with 3 mL of cold hexane, and dry it under reduced pressure to give 433 mg of a first lot of clean product (L1). Remove solvent from the latest filtrate, dissolve the resulting residue in 15 mL of hexane, and put into the freezer. After 2 days in freezer, decant solvent and wash remaining large crystals with 2 mL of cold hexane and dried under reduced pressure to give 333 mg of a second lot of product (L1). Combined yield 766 mg (44.8%) of Metal-ligand Complex (L1).

$^1$H NMR (C$_6$D$_6$, 500 MHz, 30° C.): 7.01-7.08 (m, 3H, i-Pr$_2$-Ph), 5.19 (t, 1H, $^3J_{H-H}$=5 Hz, H2), 3.67 (m, 2H, H7), 2.59 (sept. 2H, $^3J_{H-H}$=6.8 Hz, CH(CH$_3$)$_2$), 2.18 (q, 2H, $^3J_{H-H}$=5.5 Hz, H3), 2.01 (t, 2H, $^3J_{H-H}$=6.4 Hz, H5), 1.76 (m, 2H, H8), 1.34 (m, 4H, H4/H9), 1.19 (d, 6H, $^3J_{H-H}$=6.4 Hz, CH(CH$_3$)$_2$), 0.92 (t, 3H, $^3J_{H-H}$=7.4 Hz, H10), 0.91 (d, 6H, $^3J_{H-H}$=6.8 Hz, CH(CH$_3$)$_2$), 0.48 (s, 9H, Hf—CH$_3$).

Not shown are $^{13}$C NMR (C$_6$D$_6$, 125 MHz, 30° C.), HSQCAD (C$_6$D$_6$, 500 MHz, 30° C.), and elemental analysis (C, H, N) data and an ORTEP depiction of a single crystal structure derived by x-ray analysis.

Preparation 25: preparation of Metal-ligand Complex (M1), ([N-[2-[[2,6-bis(1-methylethyl)phenyl]amino-kappaN]-3-methylbutan-2-ylidene]-2,6-bis(1-ethylethyl)benzenaminato-kappaN])trimethylzirconium.

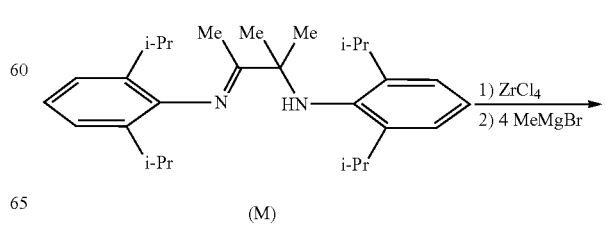

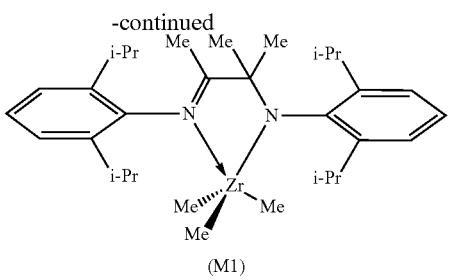

(M1)

Prepare (E)-N-(3-(2,6-diisopropylphenylamino)-3-methylbutan-2-ylidene)-2,6-diisopropylaniline (M) as described in U.S. Pat. No. 7,199,255 B2, at column 37, line 43, to column 38, line 32.

To a (E)-N-(3-(2,6-diisopropylphenylamino)-3-methylbutan-2-ylidene)-2,6-diisopropylaniline (13.6 g, 32.3 mmol) dissolved in 250 mL of toluene is added 22.4 mL (35.8 mmol) of 1.6 M n-BuLi solution in hexanes. After stirring for 2.5 hours ZrCl$_4$ (7.4 g, 32 mmol) is added and the resulting mixture is stirred overnight as a dark brown slurry. To this mixture is added 35.5 mL (107 mmol) of MeMgBr (3 M in Et$_2$O). After stirring for 3 hours at ambient temperature, the solvents are removed in vacuo. The resulting gray powder is treated with toluene (120 mL) to dissolve the product, and filtered to remove insoluble salts. The filter cake is washed with additional toluene (2×40 mL). The toluene fractions are combined and the volatile components are removed in vacuo to yield a light tan solid, 13.5 g (75%) as of Metal-ligand Complex (M1).

Preparation 26: preparation of Metal-ligand Complex (M2), ([N-[2-[[2,6-bis(1-methylethyl)phenyl]amino-kappaN]-3-methylbutan-2-ylidene]-2,6-bis(1-methylethyl)benzenaminato-kappaN])trimethylhafnium.

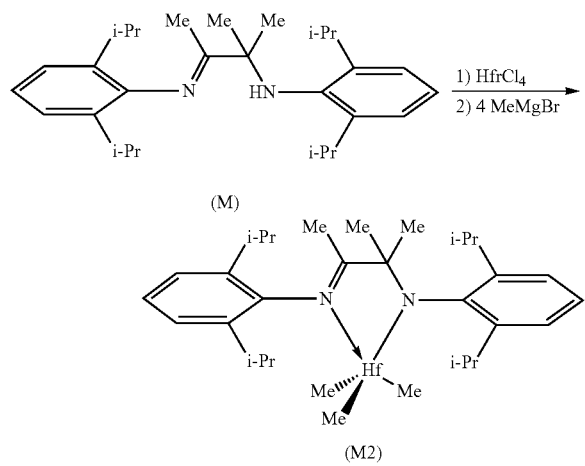

To a (E)-N-(3-(2,6-diisopropylphenylamino)-3-methylbutan-2-ylidene)-2,6-diisopropylaniline (3.00 g, 7.13 mmol) dissolved in 60 mL of toluene is added 4.9 mL (7.9 mmol) of 1.6 M n-BuLi solution in hexanes. After stirring for 90 minutes HfCl$_4$ (2.284 g, 7.132 mmol) is added and the mixture is stirred overnight as a dark brown slurry. To this mixture is added 2.61 mL (7.84 mmol) of MeMgBr (3 M in Et$_2$O). After stirring for 2 hours at ambient temperature, the solvents are removed in vacuo. The light brown residue is extracted with toluene, and filtered to remove insoluble salts. The filtrate is reduced in vacuo to yield a yellow solid, 3.04 g (66%) as Metal-ligand Complex (M2).

Preparation 27: preparation of Metal-ligand Complex (B5), (N-((6E)-6-(butylimino-kappaN)-1-cyclohexen-1-yl)-2,6-bis(1-methylethyl)benzenaminato-kappaN)trimethylzirconium.

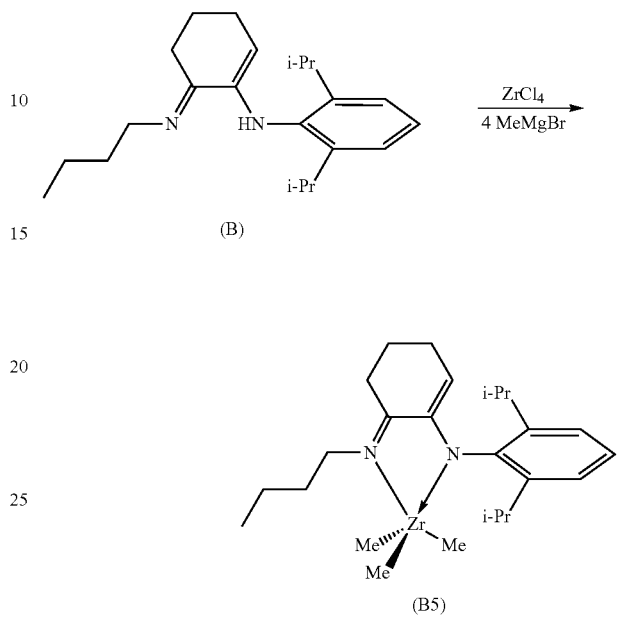

To a cold (−25° C.) toluene solution (50 mL) of (6E)-6-(butylimino)-N-(1,1':3',1"-terphenyl)-2'-yl-1-cyclohexen-1-amine (B) (Preparation 7) and ZrCl$_4$ is added 3 M MeMgBr ether solution at ambient temperature. During addition of MeMgBr gas evolution is observed. Reaction mixture does not get warm. Within minutes reaction mixture changes color from yellow to black. Solution is stirred for 2 hours. Solvent is removed under reduced pressure. To the residue is added 20 mL of toluene followed by 30 mL of hexane and solution is filtered. Solvent is removed under reduced pressure to give dark orange oil which solidifies into highly crystalline solid within 1 hour. To the solid is added 20 mL of hexane and the resulting suspension is stirred for 3 hours at room temp. Solid is collected on the frit, washed with 5 mL of cold hexane and dried under reduced pressure to give 1.44 g of Metal-ligand Complex (B5). The filtrate is put into freezer overnight. Solvent is decanted and large dark orange crystals are washed with 4 mL of cold hexane and dried under reduced pressure to give 680 mg of Metal-ligand Complex (B5). Combined yield 2.12 g (59.1%) of Metal-ligand Complex (B5).

$^1$H NMR (500 MHz, C$_6$D$_6$) δ 7.21 (s, 3H), 4.70 (t, J=5.0 Hz, 1H), 3.48 (hept, J=6.9 Hz, 2H), 3.36-3.29 (m, 2H), 1.98-1.93 (m, 2H), 1.85 (dd, J=11.3, 5.7 Hz, 2H), 1.40 (d, J=6.9 Hz, 6H), 1.38-1.32 (m, 3H), 1.34-1.28 (m, J=6.0 Hz, 2H), 1.22 (d, J=6.9 Hz, 6H), 1.08 (sex, J=7.5 Hz, 2H), 0.77 (t, J=7.4 Hz, 3H), 0.74 (s, 9H).

$^{13}$C NMR (126 MHz, C$_6$D$_6$) δ 174.54 (s), 151.62 (s), 144.89 (s), 144.19 (s), 126.13 (s), 124.24 (s), 113.42 (s), 49.91 (s), 48.60 (s), 31.21 (s), 28.57 (s), 27.79 (s), 26.02 (s), 24.77 (s), 24.56 (s), 23.18 (s), 20.99 (s), 13.84 (s).

Anal. Calcd for C$_{25}$H$_{42}$N$_2$Zr: C, 65.02; H, 9.17; N, 6.07. Found: C, 64.92; H, 9.08; N, 6.07.

Not shown is an ORTEP depiction of a single crystal structure derived by x-ray analysis.-

Preparation 28: preparation of 1,3-bis(2,6-diisopropylphenyl)-1H-imidazol-2(3H)-imine (N).

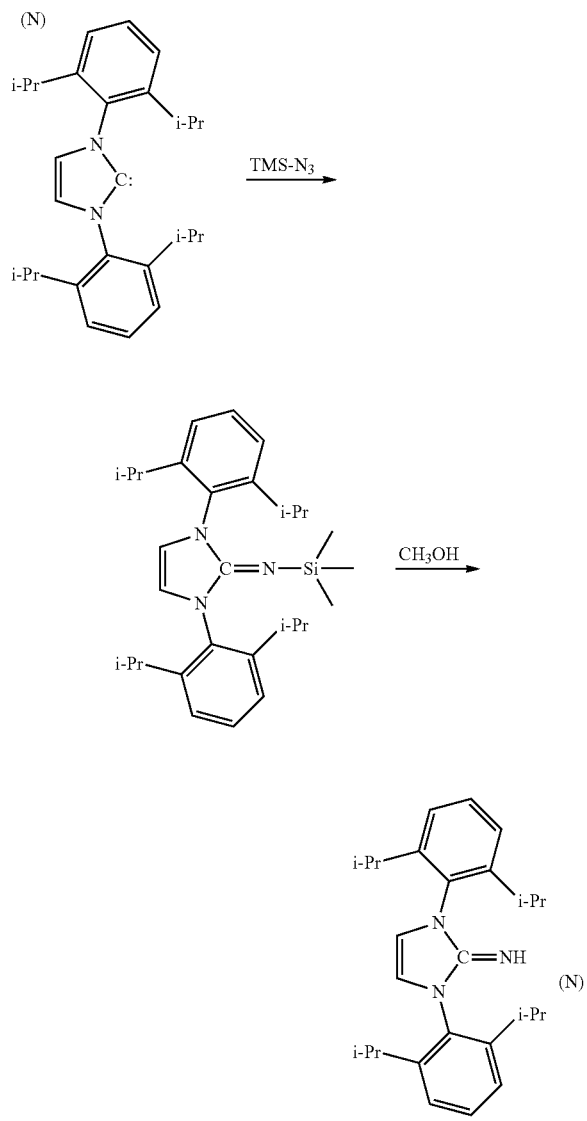

Dissolve 1,3-bis[2,6-bis(1-methylethyl)phenyl]-1,3-dihydro-2H-imidazol-2-ylidene (4.00 g, 10.3 mmol, Aldrich Chemical Company) and trimethylsilylazide (3.56 g, 30.9 mmol) in 45 mL of toluene, and heat the resulting mixture for 24 hours at 117° C. Remove solvent under reduced pressure to give a yellow solid. Dissolve the yellow solid in 20 mL of toluene followed by addition of 8 mL of methanol. After stirring the resulting mixture for 1 hour at room temperature, remove solvent under reduced pressure. To the residue add 10 mL of hexane, stir the resulting suspension for 10 minutes, and then put it in a freezer overnight. Collect solid on a sintered glass funnel, wash the collected solid twice with cold hexane (2×5 mL), and dry it under reduced pressure to yield 3.84 g (92.4%) of product (N).

$^1$H NMR (300 MHz, $C_6D_6$) δ 7.24 (dd, J=8.6, 6.6 Hz, 2H), 7.17-7.12 (m, 4H), 5.87 (s, 2H), 4.15 (s, 1H), 3.21 (heptet, J=6.9 Hz, 4H), 1.34 (d, J=6.9 Hz, 12H), 1.21 (d, J=6.9 Hz, 12H).

$^{13}C\{^1H\}$ NMR (75 MHz, $C_6D_6$) δ 154.49 (s), 148.50 (s), 129.59 (s), 124.26 (s), 113.67 (s), 29.18 (s), 24.23 (s), 24.15 (s).

EXAMPLES OF THE PRESENT INVENTION

Example 1

Preparation of Metal-Ligand Complex (1), (N-((6E)-6-(butylimino-kappaN)-1-cyclohexen-1-yl)-2,6-bis(1-methylethyl)benzenaminato-kappaN)bis(phenylmethyl)-tris(1,1-dimethylethyl)phosphineimidozirconium

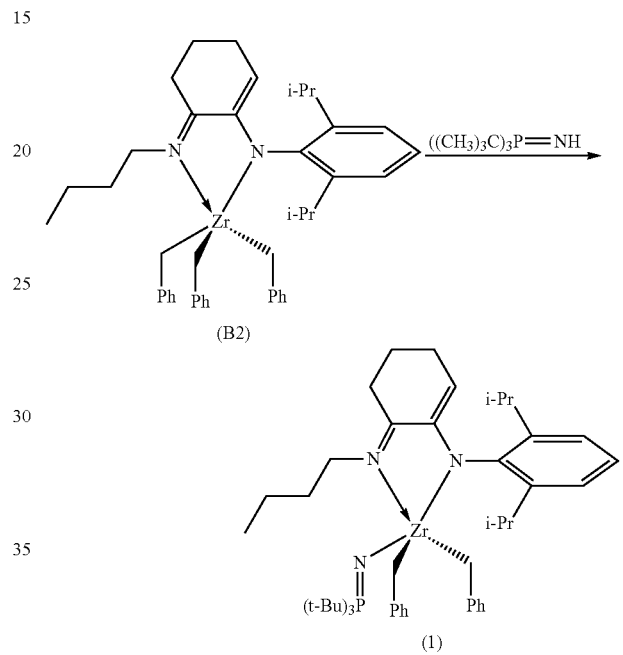

Dissolve Metal-ligand Complex (B2) of Preparation 16 in 5 mL of toluene giving yellow solution. To this solution add a solution of 1 mole equivalent of tris(1,1-dimethylethyl)phosphineimide (Rankin D. W. H., et al., Journal of the Chemical Society, Dalton Trans., 1985:827-830) in 1 mL of toluene. After stirring for 1 hour, remove solvent under reduced pressure, giving a yellow crystalline solid. Dissolve the solid in warm toluene (5 mL), add 10 mL of hexane, and place the resulting solution in a freezer (−26° C.) overnight. Decant solvent, and wash the remaining yellow crystals with hexane (2×10 mL) and dry under reduced pressure to give 255 mg (66% yield) of product (1).

$^1$H NMR (500 MHz, $C_6D_6$) δ 7.34-7.25 (m, 3H), 7.16 (t, J=7.6 Hz, 4H), 7.00 (d, J=5.9 Hz, 4H), 6.84 (t, J=7.3 Hz, 2H), 4.60 (t, J=5.0 Hz, 1H), 3.56-3.44 (m, 4H), 2.59 (d, J=10.8 Hz, 2H), 2.43 (d, J=10.1 Hz, 2H), 2.20-2.06 (m, 2H), 1.88 (q, J=5.7 Hz, 2H), 1.54-1.44 (m, 2H), 1.37 (p, J=6.2 Hz, 2H), 1.33 (d, J=6.9 Hz, 6H), 1.25 (sex, J=7.5 Hz, 2H), 1.25 (d, J=6.8 Hz, 6H), 1.13 (d, J=12.7 Hz, 27H), 0.84 (t, J=7.4 Hz, 3H).

$^{13}$C NMR (126 MHz, $C_6D_6$) δ 175.09 (s), 152.63 (s), 151.88 (s), 148.44 (s), 144.90 (s), 128.14 (s), 126.21 (s), 125.09 (s), 124.49 (s), 119.85 (s), 112.95 (s), 67.12 (s), 51.42 (s), 40.48 (d, J=46.8 Hz), 31.02 (s), 29.70 (s), 28.79 (s), 28.48 (s), 26.23 (s), 25.35 (s), 24.38 (s), 23.30 (s), 21.15 (s), 13.85 (s).

$^{31}$P NMR (121 MHz, $C_6D_6$) δ 34.75 (s).

Anal. Calcd for $C_{36}H_{66}ZrN_3P$: C, 65.20; H, 10.03; N, 6.34. Found: C, 57.41; H, 8.61; N, 4.20.

Figure 3:
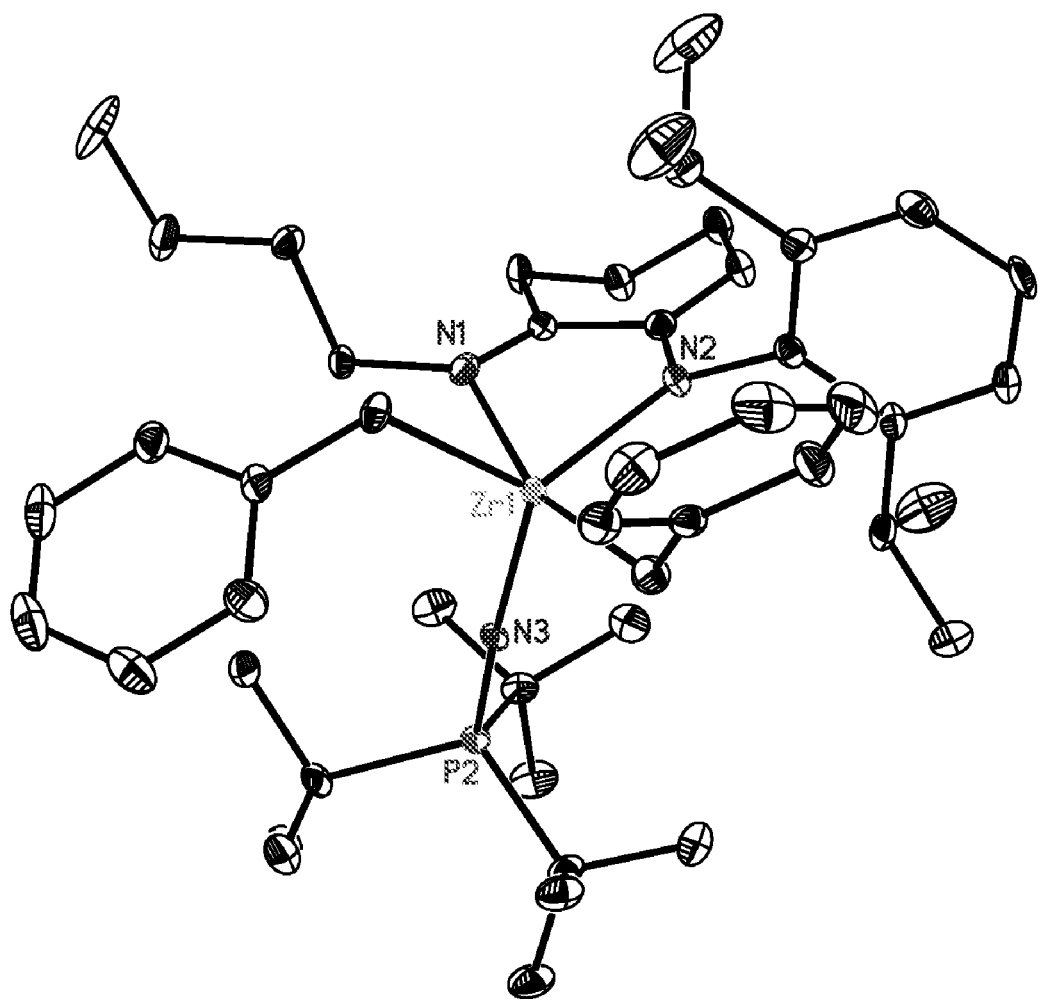
FIG. 3 shows an Oak Ridge Thermal Ellipsoid Plot (ORTEP) depiction of a single crystal structure derived by x-ray analysis of invention Metal-ligand Complex (1) (Example 1) with hydrogen atoms omitted for clarity.

FIG. 3 shows an ORTEP depiction of a single crystal structure derived by x-ray analysis of Metal-ligand Complex (1). In FIG. 3, hydrogen atoms are omitted for clarity.

Example 2

Preparation of Metal-Ligand Complex (2), ([N-[2-[[2,6-bis(1-methylethyl)phenyl]amino-kappaN]-3-methylbutan-2-ylidene]-2,6-bis(1-methylethyl)benzenaminato-kappaN]phosphineimido-zirconium

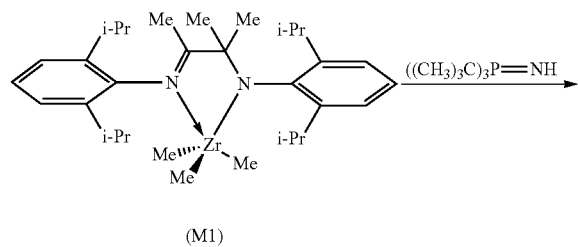

(M1)

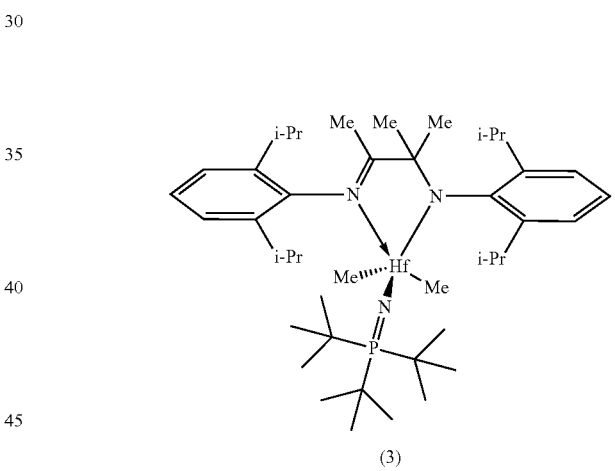

(2)

Dissolve Metal-ligand Complex (M1) (Preparation 25) in 5 mL of toluene, and add tBu$_3$P=NH as a solid followed by 3 mL of hexane washing. Observe gas evolution during addition of tBu$_3$P=NH. Stir the resulting reaction mixture at room temperature for 1 hour, and then remove solvent under reduced pressure to give crystalline off-white product (2). Dissolve product (2) in 12 mL of warm hexane, and put the resulting solution into freezer (−27° C.). After two days transfer resulting small sample of crystals to a vial. Decant the solvent, and was resulting off-white crystals with 2 mL of cold hexane and dry under reduced pressure to give 310 mg of product (2); yield 52%.

$^1$H NMR (500 MHz, $C_6D_6$) δ 7.20-7.13 (m, 5H), 7.09 (dd, J=8.1, 7.0 Hz, 2H), 3.75 (sept, J=6.8 Hz, 3H), 3.02 (sept, J=6.8 Hz, 2H), 1.61 (s, 3H), 1.51 (d, J=6.8 Hz, 6H), 1.38 (d, J=7.1 Hz, 6H), 1.37 (s, 6H), 1.32 (d, J=6.9 Hz, 6H), 1.16 (d, J=12.5 Hz, 27H), 1.12 (d, J=6.8 Hz, 6H), 0.29 (s, 6H).

$^{13}$C NMR (126 MHz, $C_6D_6$) δ 194.81 (s), 149.41 (s), 147.85 (s), 146.77 (s), 139.39 (s), 126.05 (s), 124.63 (s), 124.03 (s), 123.98 (s), 70.98 (s), 40.95 (d, J=47.0 Hz), 36.98 (s), 30.22 (s), 30.03 (s), 28.57 (s), 28.38 (s), 26.97 (s), 25.23 (s), 24.74 (s), 23.95 (s), 19.57 (s).

$^{31}$P NMR (121 MHz, $C_6D_6$) δ 31.25 (s).

Figure 4:
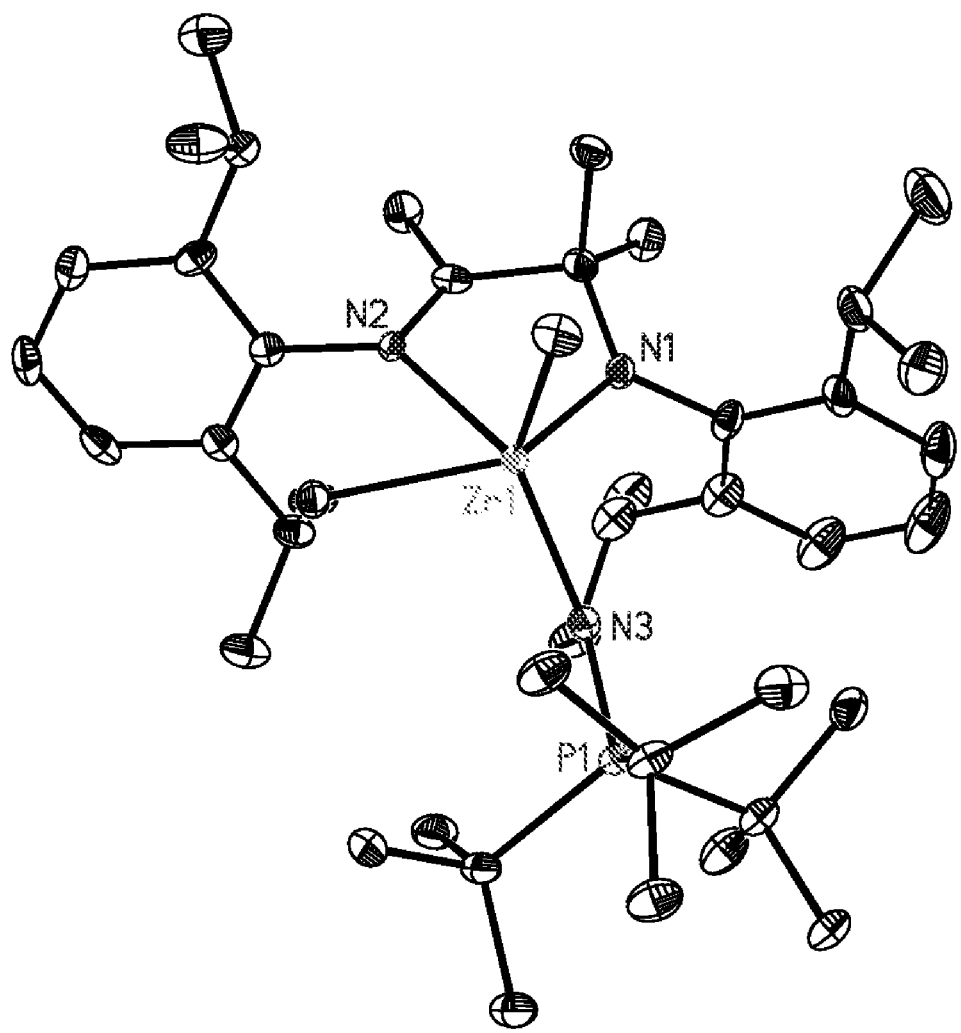
FIG. 4 shows an ORTEP depiction of a single crystal structure derived by x-ray analysis of invention Metal-ligand Complex (2) (Example 2) with hydrogen atoms omitted for clarity.

FIG. 4 shows an ORTEP depiction of a single crystal structure derived by x-ray analysis of Metal-ligand Complex (2). In FIG. 4, hydrogen atoms are omitted for clarity.

Example 3

Preparation of Metal-Ligand Complex (3), ([N-[2-[[2,6-bis(1-methylethyl)phenyl]amino-kappaN]-3-methylbutan-2-ylidene]-2,6-bis(1-methylethyl)benzenaminato-kappaN]phosphineimido-hafnium

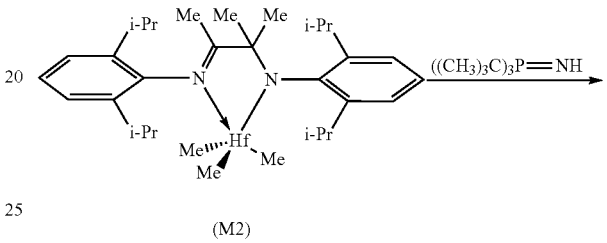

(M2)

In a manner similar to the procedure of Example 2 except use Metal-ligand Complex (M2) (Preparation 26) instead of Metal-ligand Complex (M1) to prepare 81 mg of product (3); yield 60%.

$^1$H NMR (500 MHz, $C_6D_6$) δ 7.18 (d, J=7.4 Hz, 2H), 7.15-7.13 (m, 3H), 7.08 (dd, J=8.1, 7.1 Hz, 1H), 3.75 (sept, J=6.9 Hz, 2H), 3.02 (sept, J=6.8 Hz, 2H), 1.57 (s, 3H), 1.53 (d, J=6.9 Hz, 6H), 1.38 (d, J=6.8 Hz, 6H), 1.34 (s, 6H), 1.32 (d, J=6.9 Hz, 6H), 1.15 (d, J=12.4 Hz, 27H), 1.10 (d, J=6.8 Hz, 6H), 0.15 (s, 6H).

$^{13}$C NMR (126 MHz, $C_6D_6$) δ 196.17 (s), 150.00 (s), 148.10 (s), 146.80 (s), 139.61 (s), 126.23 (s), 124.59 (s), 124.06 (s), 123.94 (s), 71.52 (s), 48.31 (s), 41.13 (d, J=47.7 Hz), 30.26 (s), 30.22 (s), 28.50 (s), 28.40 (s), 27.01 (s), 25.30 (s), 24.74 (s), 23.96 (s), 19.61 (s).

$^{31}$P NMR (121 MHz, $C_6D_6$) δ 37.38 (s).

Example 4

Preparation of Metal-Ligand Complex (4), (N-((6E)-6-(butylimino-kappaN)-1-cyclohexen-1-yl)-2,6-bis(1-methylethyl)benzenaminato-kappaN)bis(phenylmethyl)-tris(1,1-dimethylethyl)phosphineimido-hafnium

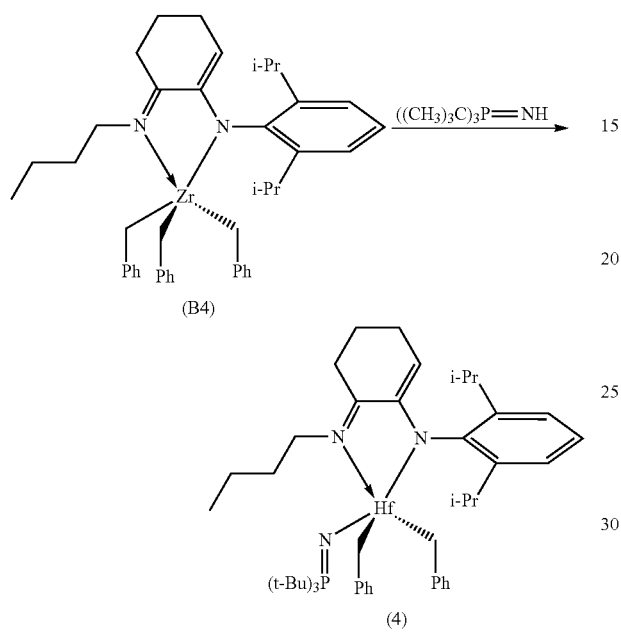

Dissolve Metal-ligand Complex (B4; 0.3128 g, 0.55 millimole) of Preparation 19 in 15 mL of toluene giving yellow solution. Cool to −26° C. To this solution add a solution of 1 mole equivalent of tris(1,1-dimethylethyl)phosphineimide in 8 mL of hexane. After stirring overnight, remove solvent under reduced pressure, giving a yellow solid. Dissolve the solid in hexane (3 mL), and place the resulting solution in a freezer (−27° C.) overnight. After 24 hours, decant solvent, and dry the remaining crystals under reduced pressure to give 289 mg (83% yield) of product (4).

$^1$H NMR (500 MHz, $C_6D_6$) δ 7.31 (d, J=7.5 Hz, 2H), 7.22 (t, J=7.5 Hz, 1H), 4.59 (t, J=5.0 Hz, 1H), 3.72-3.67 (m, 2H), 3.65 (sept, J=6.5 Hz, 2H), 2.13 (d, J=6.3 Hz, 2H), 1.98 (q, J=5.6 Hz, 2H), 1.52 (p, J=5.6 Hz, 2H), 1.50 (d, J=6.9 Hz, 6H), 1.42 (p, J=5.7 Hz, 2H), 1.30 (d, J=6.9 Hz, 6H), 1.27 (d, J=12.5 Hz, 27H), 0.87 (t, J=7.4 Hz, 3H), 0.18 (s, 6H).

$^{13}$C NMR (126 MHz, $C_6D_6$) δ 174.95 (s), 153.57 (s), 149.17 (s), 144.78 (s), 124.58 (s), 123.74 (s), 111.76 (s), 50.94 (s), 46.03 (s), 40.80 (d, J=48.0 Hz), 30.98 (s), 29.76 (s), 28.64 (s), 28.21 (s), 26.05 (s), 25.24 (s), 24.71 (s), 23.66 (s), 21.27 (s), 13.90 (s).

$^{31}$P NMR (121 MHz, $C_6D_6$) δ 38.30 (s).

Anal. Calcd for $C_{36}H_{66}HfN_3P$: C, 57.62; H, 8.87; N, 5.60. Found: C, 57.41; H, 8.61; N, 5.65.

Examples 5 to 8

Preparation of Metal-Ligand Complexes (5) to (8)

In a manner similar to the procedure of Example 4 except in separate experiments using a different one of the hafnium-ligand complexes (L1), (G1), (D1), and (H1) instead of the hafnium-ligand complex (B4), the following Metal-ligand Complexes (5) to (8) can be respectively prepared:

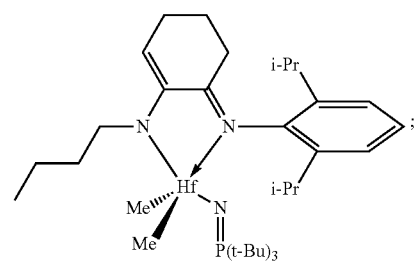

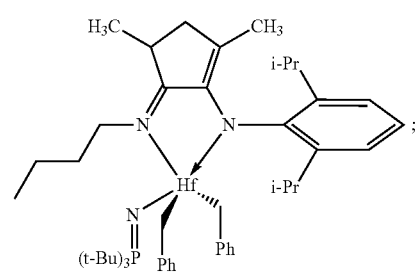

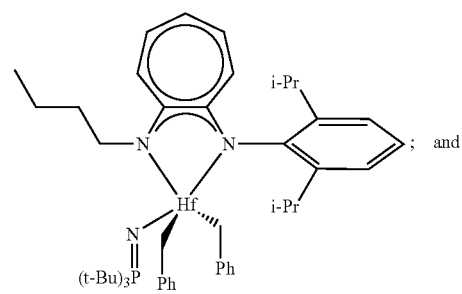

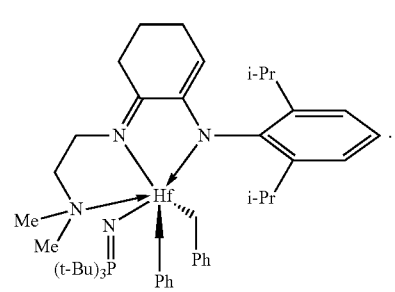

Example 9

Preparation of Metal-Ligand Complex (9), (N-((6E)-6-(butylimino-kappaN)-1-cyclohexen-1-yl)-2,6-bis(1-methylethyl)benzenaminato-kappaN)dimethyl-(2,3,4-trimethyl-3-pentanolato)-zirconium

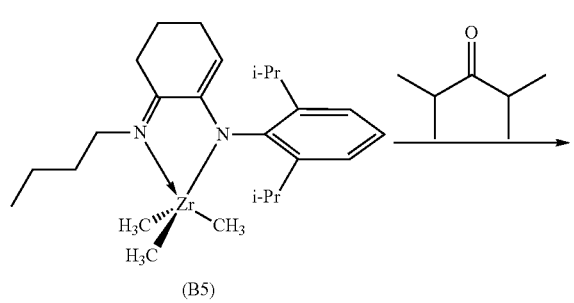

(B5)

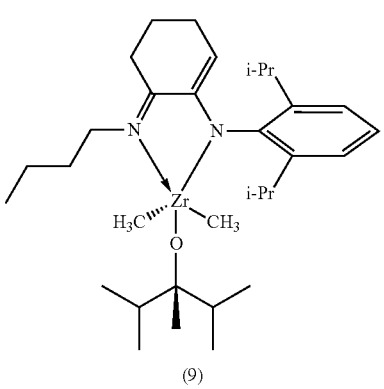

(9)

To a vial containing Metal-ligand complex (B5) (Preparation 27) is added a solution of di-i-Pr-ketone (2,4-dimethylpentan-3-one) dissolved in 0.6 mL of $C_6D_6$. Transfer resulting contents of the vial to an NMR tube. An NMR spectrum taken after 15 minutes shows quantitative formation of Metal-ligand Complex (9). Remove solvent and obtain Metal-ligand Complex (9) in isolated and pure form.

$^1$H NMR (300 MHz, $C_6D_6$) δ 7.18 (s, 3H), 4.56 (t, J=4.9 Hz, 1H), 3.72-3.62 (m, 2H), 3.25 (hept, J=6.8 Hz, 2H), 2.12 (t, J=6.2 Hz, 2H), 1.90 (sept, J=6.8 Hz, 2H), 1.86 (q, J=5.5 Hz, 2H), 1.67-1.53 (m, 2H), 1.39 (d, J=6.9 Hz, 6H), 1.37 (p, J=6.4 Hz, 2H), 1.20 (sex, J=7.4 Hz, 2H), 1.16 (d, J=6.8 Hz, 6H), 0.98 (s, 3H), 0.94 (d, J=6.8 Hz, 6H), 0.90 (d, J=6.9 Hz, 6H), 0.82 (t, J=7.3 Hz, 3H), 0.50 (s, 6H).

$^{13}$C NMR (75 MHz, $C_6D_6$) δ 173.75 (s), 149.88 (s), 144.97 (d, J=5.9 Hz), 144.36 (s), 125.94 (s), 124.23 (s), 112.17 (s), 87.27 (d, J=2.0 Hz), 50.69 (s), 36.15 (s), 36.11 (s), 31.47 (s), 28.71 (s), 28.39 (s), 25.80 (s), 25.06 (s), 23.57 (s), 21.52 (s), 20.07 (s), 18.67 (s), 18.03 (s), 14.16 (s).

Example 10

Preparation of Metal-Ligand Complex (10), (2,6-bis(1,1-dimethylethyl)phenolate)(N-((6E)-6-(butylimino-kappaN)-1-cyclohexen-1-yl)-2,6-bis(1-methylethyl)benzenaminato-kappaN)dimethyl-hafnium

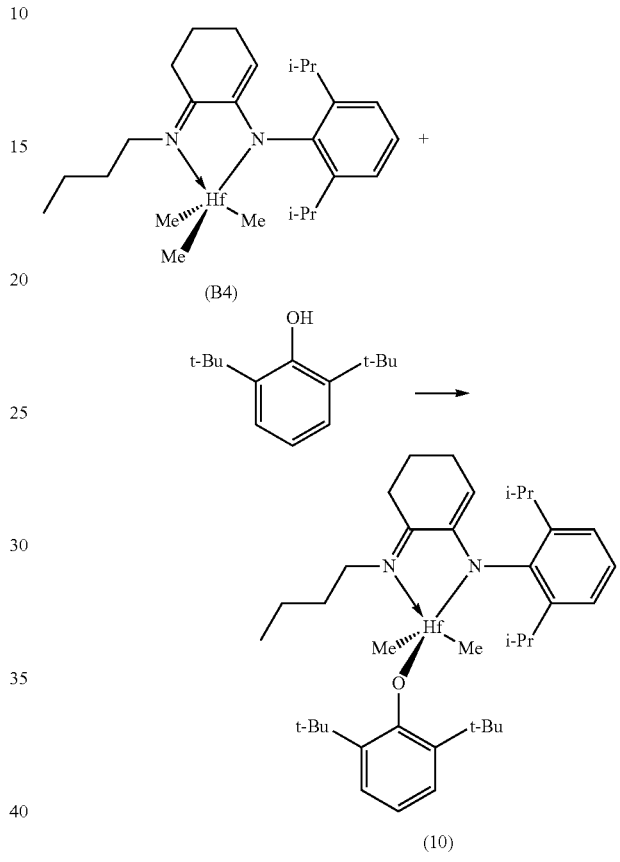

To a vial containing a solution of Metal-ligand Complex (B4) (Preparation 19) dissolved in 2 mL of $C_6D_6$ is added a solution of 57.3 mg of 2,6-bis(1,1-dimethylethyl)phenol dissolved in 1 mL of $C_6D_6$. No gas evolution is observed. Leave reaction mixture for 18 hours at ambient temperature (about 24° C.). NMR spectrum shows quantitative formation of Metal-ligand Complex (10). Remove solvent and obtain Metal-ligand Complex (10) in isolated and pure form.

$^1$H NMR (500 MHz, $C_6D_6$) δ 7.40-7.36 (m, 2H), 7.32-7.28 (m, 2H), 7.25 (dd, J=8.7, 6.3 Hz, 1H), 6.91 (t, J=7.8 Hz, 1H), 4.66 (t, J=5.0 Hz, 1H), 3.70 (sept, J=6.8 Hz, 2H), 3.29-3.22 (m, 2H), 1.92-1.84 (m, 4H), 1.62 (s, 18H), 1.45 (d, J=6.9 Hz, 6H), 1.25 (p, J=6.5 Hz, 2H), 1.23 (d, J=6.8 Hz, 6H), 1.22-1.16 (m, 2H), 0.91 (sex, J=7.4 Hz, 2H), 0.64 (t, J=7.4 Hz, 3H), 0.57 (s, 6H).

$^{13}$C NMR (126 MHz, $C_6D_6$) δ 177.48 (s), 162.40 (s), 152.75 (s), 147.46 (s), 145.05 (s), 139.20 (s), 125.91 (s), 125.71 (s), 124.49 (s), 120.19 (s), 117.73 (s), 56.10 (s), 49.61 (s), 35.26 (s), 31.69 (s), 31.45 (s), 28.07 (s), 27.85 (s), 26.62 (s), 24.89 (d, J=3.5 Hz), 23.15 (s), 20.74 (s), 13.84 (s).

Anal. Calcd for $C_{38}H_{60}HfN_2O$: C, 61.73; H, 8.18; N, 3.79. Found: C, 62.19; H, 8.03; N, 3.03.

Figure 5:
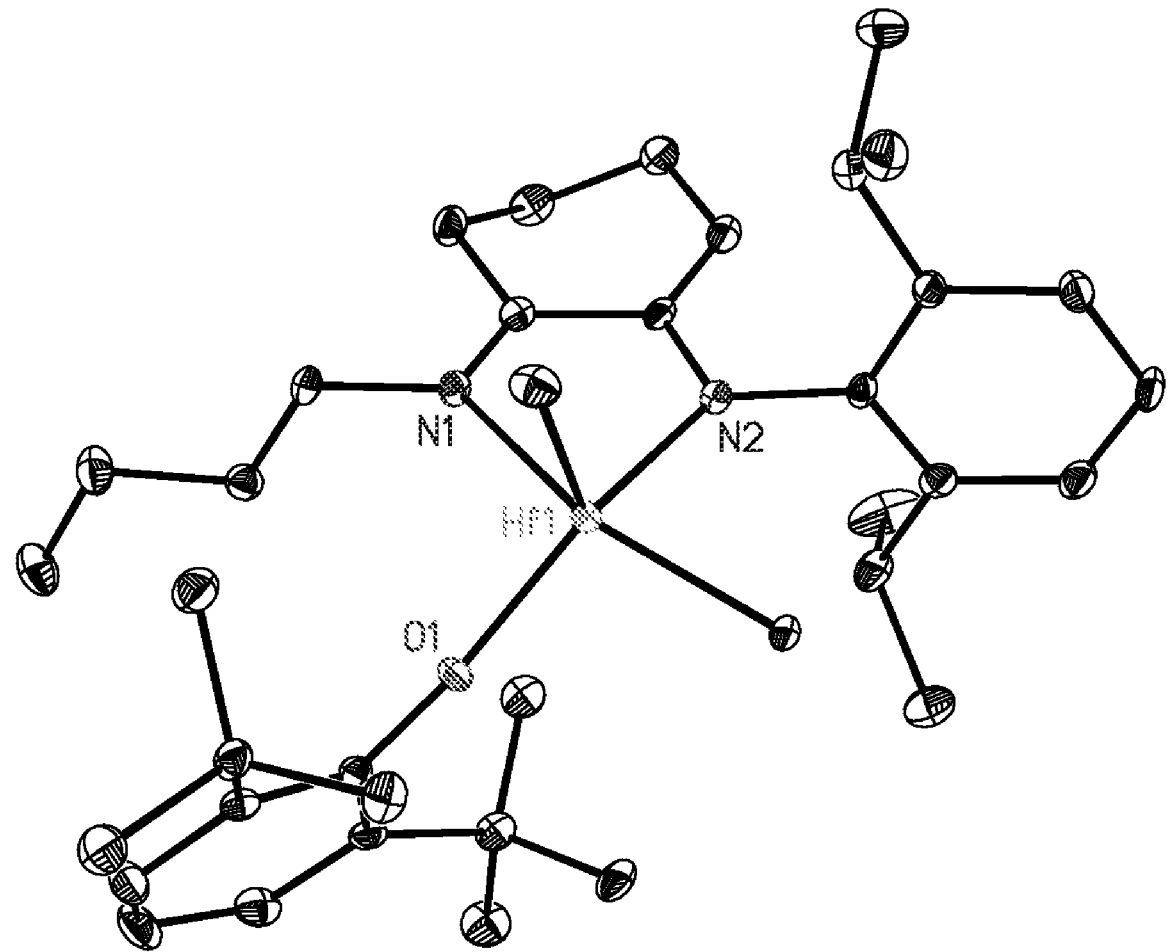
FIG. 5 shows an ORTEP depiction of a single crystal structure derived by x-ray analysis of invention Metal-ligand Complex (10) (Example 10) with hydrogen atoms omitted for clarity.

FIG. 5 shows an ORTEP depiction of a single crystal structure derived by x-ray analysis of invention Metal-ligand Complex (10) (Example 10). In FIG. 5 hydrogen atoms are omitted for clarity.

Example 11

Preparation of Metal-Ligand Complex (11), (N-((6E)-6-(butylimino-kappaN)-1-cyclohexen-1-yl)-2,6-bis(1-methylethyl)benzenaminato-kappaN) [N,N'-bis(1-methylethyl)ethanimidamidato-kappaN,kappaN']dimethyl-zirconium

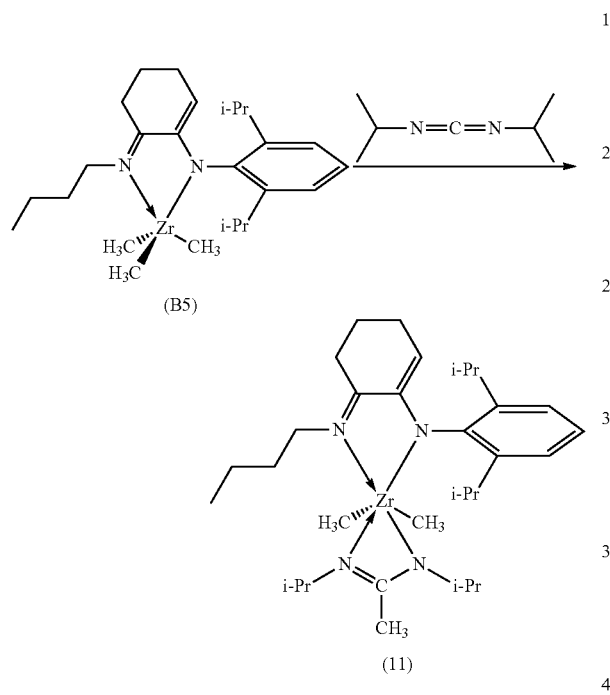

(11)

To a vial containing N,N'-methanetetraylbis-2-propanamine is added Metal-ligand Complex (B5), (6-(butylimino-κ N)—N-(1,1':3',1''-terphenyl)-2'-yl-1-cyclohexen-1-aminato-κN)trimethyl-zirconium (Preparation 27) dissolved in 3 mL of toluene. Solution is stirred for 15 minutes, and then solvent is removed under reduced pressure. The residue is dissolved in 3 mL of hexane and solution is put into freezer (−30° C.) for 2 days. Solvent is decanted and very large orange-brown crystals are washed with 2 mL of cold hexane and dried under reduced pressure to give 131 mg of Metal-ligand Complex (11). Yield 61.7%.

$^1$H NMR (500 MHz, $C_6D_6$) δ 7.32-7.28 (m, 2H), 7.24 (dd, J=8.4, 6.6 Hz, 1H), 4.72 (t, J=5.0 Hz, 1H), 3.77 (sept, J=6.8 Hz, 2H), 3.47 (sept, J=6.5 Hz, 2H), 3.37-3.32 (m, 2H), 2.05 (s, J=6.3 Hz, 2H), 1.91 (q, J=5.7 Hz, 2H), 1.61 (s, 3H), 1.54-1.47 (m, 2H), 1.46 (d, J=6.9 Hz, 6H), 1.39 (p, J=6.1 Hz, 2H), 1.28 (d, J=6.8 Hz, 6H), 1.20 (d, J=7.5 Hz, 2H), 1.17 (d, J=6.5 Hz, 12H), 0.84 (d, J=7.4 Hz, 3H), 0.57 (s, 6H).

$^{13}$C NMR (126 MHz, $C_6D_6$) δ 177.25 (s), 174.19 (s), 153.22 (s), 148.96 (s), 144.69 (s), 124.88 (s), 124.06 (s), 114.06 (s), 49.80 (s), 48.46 (s), 45.00 (s), 31.23 (s), 28.06 (s), 28.02 (s), 26.52 (s), 25.25 (s), 24.75 (s), 24.56 (s), 23.29 (s), 21.33 (s), 14.01 (s), 10.75 (s).

Anal. Calcd for $C_{33}H_{56}HfN_4$: C, 65.36; H, 9.60; N, 9.53. Found: C, 65.06; H, 9.29; N, 9.37.

Figure 6:
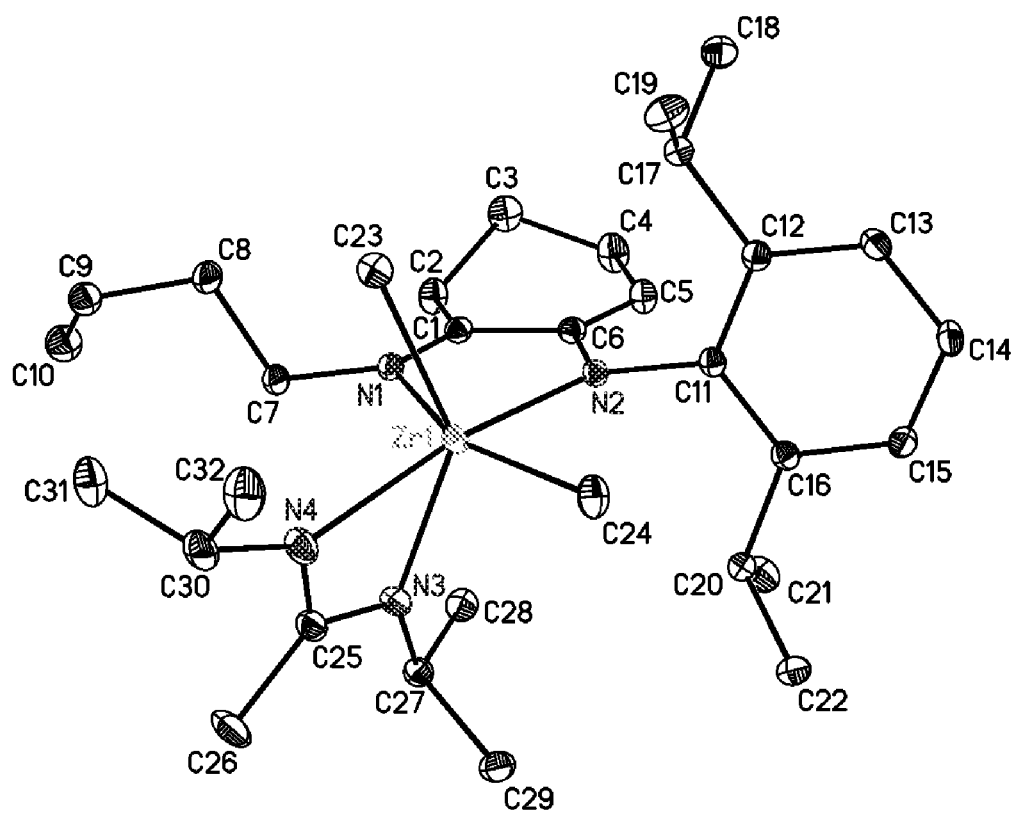
FIG. 6 shows an ORTEP depiction of a single crystal structure derived by x-ray analysis of Metal-ligand Complex (11) with hydrogen atoms are omitted for clarity.

FIG. 6 shows an ORTEP depiction of a single crystal structure derived by x-ray analysis of Metal-ligand Complex (11). In FIG. 6, hydrogen atoms are omitted for clarity.

Example 12

Preparation of Metal-Ligand Complex (12), [(N-((6E)-6-(butylimino-kappaN)-1-cyclohexen-1-yl)-2,6-bis(1-methylethyl)benzenaminato-κN)][1,3-bis(2,6-dimethylphenyl)-1,3-dihydro-2H-imidazol-2-iminato-κN2]dimethyl-zirconium

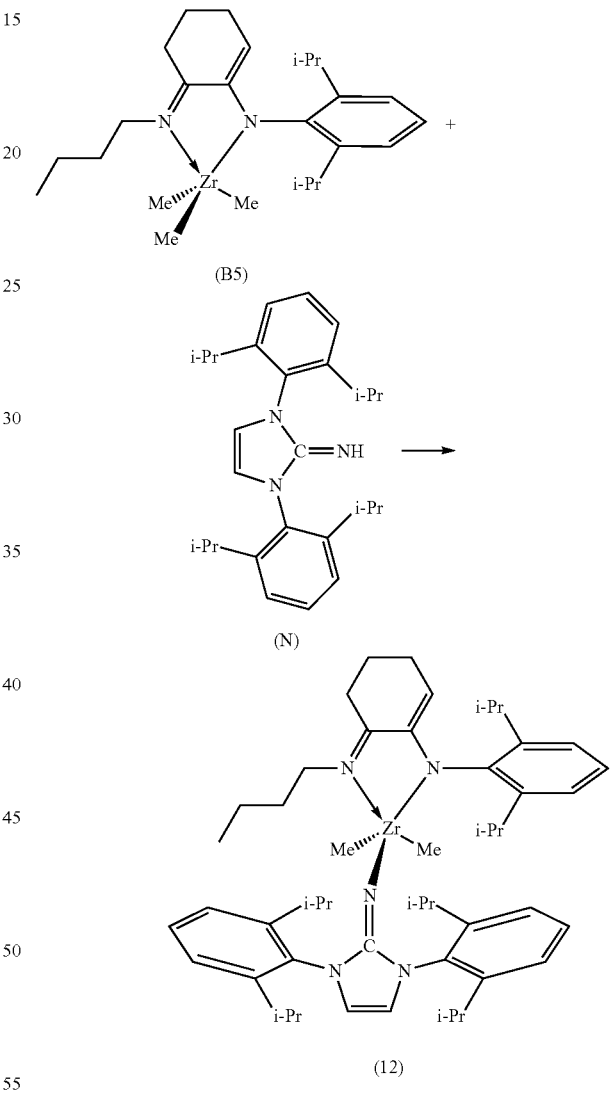

(12)

To a vial containing 66.6 mg (0.17 mg) of Metal-ligand complex (B5) (Preparation 27) is added 76.2 mg (0.17 mmol) of 1,3-bis[2,6-bis(1-methylethyl)phenyl]-1,3-dihydro-2H-imidazol-2-imine (N) (Preparation 28) dissolved in 0.8 mL of $C_6D_6$. Upon mixing of reagents gas evolution is observed. The contents of the vial are transferred to NMR tube. NMR taken after 10 minutes showed clean formation of Metal-ligand Complex (12). Solvent is removed under reduced pressure. The residue is dissolved in 4 mL of warm hexane. The vial is put into freezer overnight (−30° C.). Yellow crystalline solid is collected on a sintered glass funnel, washed with 2 mL of cold hexane and dried under reduced pressure to give 75 mg (53.5%) of Metal-ligand Complex (12).

$^1$H NMR (500 MHz, C$_6$D$_6$) δ 7.25-7.21 (m, 2H), 7.20-7.16 (m, 3H), 7.10 (d, J=7.7 Hz, 4H), 5.93 (s, 2H), 4.56 (t, J=5.0 Hz, 1H), 3.48 (sept, J=6.6 Hz, 2H), 3.27 (sept, J=6.8 Hz, 4H), 2.52-2.46 (m, 2H), 2.08 (t, J=6.2 Hz, 2H), 1.94 (q, J=5.5 Hz, 2H), 1.47 (p, J=6.2 Hz, 2H), 1.39 (d, J=7.2 Hz, 6H), 1.38 (d, J=7.0 Hz, 12H), 1.27 (d, J=6.9 Hz, 6H), 1.25-1.19 (m, 2H), 1.16 (d, J=6.9 Hz, 12H), 1.12 (sex, J=7.7 Hz, 2H), 0.81 (t, J=7.3 Hz, 3H), −0.17 (s, 6H).

$^{13}$C NMR (126 MHz, C$_6$D$_6$) δ 173.51 (s), 153.56 (s), 149.29 (s), 147.55 (s), 144.33 (s), 142.01 (s), 135.12 (s), 129.53 (s), 124.36 (s), 124.22 (s), 123.60 (s), 114.22 (s), 110.41 (s), 48.45 (s), 38.07 (s), 31.05 (s), 28.99 (s), 28.30 (s), 27.92 (s), 26.10 (s), 25.30 (s), 24.92 (s), 24.53 (s), 23.62 (s), 23.35 (s), 21.23 (s), 14.23 (s).

Anal. Calcd for C$_{51}$H$_{75}$N$_5$Zr: C, 72.12; H, 8.90; N, 8.25. Found: C, 71.95; H, 8.89; N, 8.21.

Figure 7:
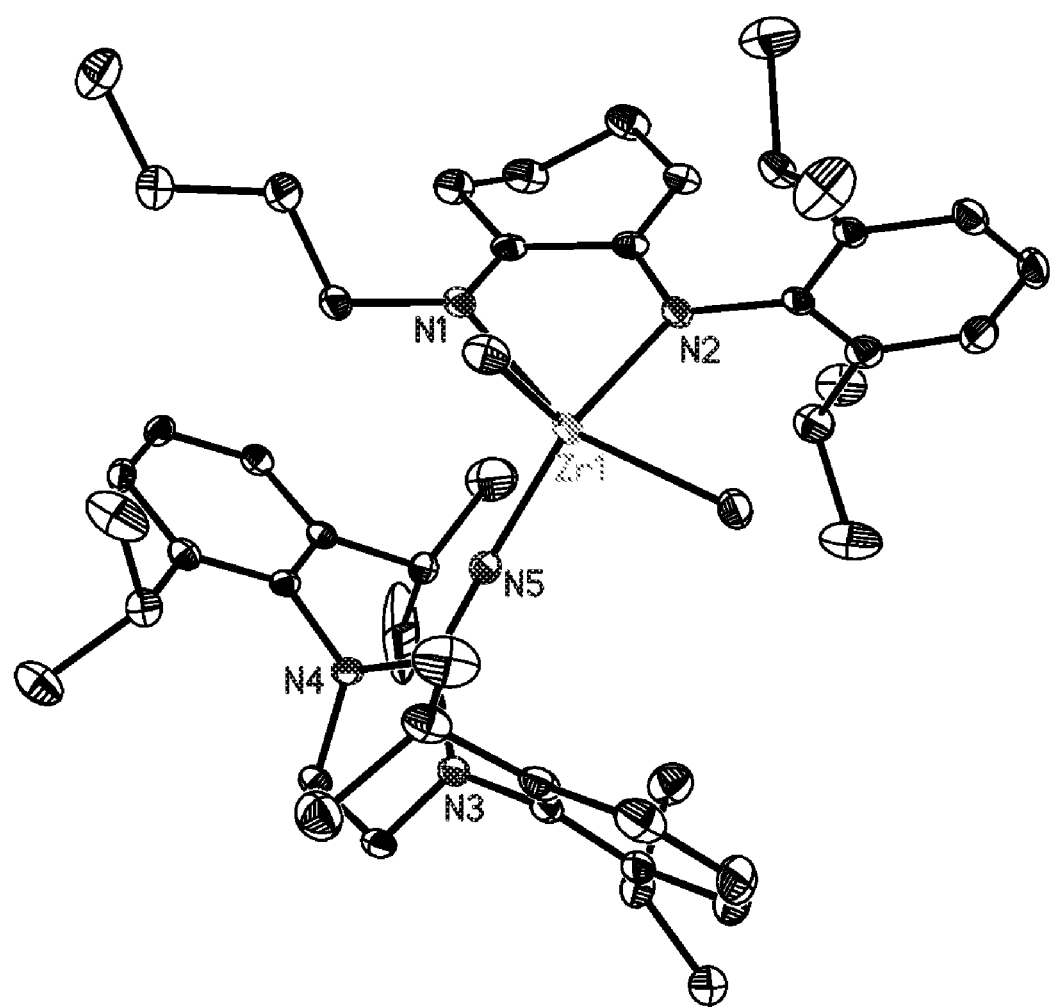
FIG. 7 shows an ORTEP depiction of a single crystal structure derived by x-ray analysis of invention Metal-ligand Complex (12) (Example 12) with hydrogen atoms are omitted for clarity.

FIG. 7 shows an ORTEP depiction of a single crystal structure derived by x-ray analysis of Metal-ligand Complex (12). In FIG. 7, hydrogen atoms are omitted for clarity. Thermal ellipsoids are shown at the 40% probability level.

Example 13

Preparation of a Metal-Ligand Complex of Formula (I)

In a manner similar to that described in Preparation 25 except instead of a ligand of formula (M) contact a ligand of any one of formulas (a), (D), (G), (H), (J), or (L) of any one of Preparations 1, 9, 10, 11, 12, or 13, respectively, with zirconium tetrachloride and 4 mole equivalents of methyl magnesium bromide to give a corresponding trimethyl zirconium-ligand complex, respectively, and then contact the trimethyl zirconium-ligand complex to a compound of formula J$^3$-H, J$^4$-H, J$^5$-H, J$^5$-H, J$^6$-H, or J$^7$-H, wherein J$^3$, J$^4$, J$^5$, J$^5$, J$^6$, and J$^7$ are as defined previously, to give a corresponding metal-ligand complex of formula (I) wherein one of the methyl (bound to zirconium) of the trimethyl zirconium-ligand complex has been replaced by J$^3$, J$^4$, J$^5$, J$^5$, J$^6$, or J$^7$, respectively.

Example 14

Preparation of a Metal-Ligand Complex of Formula (I)

In a manner similar to that described in Preparation 26 except instead of a ligand of formula (M) contact a ligand of any one of formulas (a), (D), (G), (H), (J), or (L) of any one of Preparations 1, 9, 10, 11, 12, or 13, respectively, with hafnium tetrachloride and 4 mole equivalents of methyl magnesium bromide to give a corresponding trimethyl hafnium-ligand complex, respectively, and then contact the trimethyl hafnium-ligand complex to a compound of formula K$^1$-H, K$^2$-H, K$^3$-H, K$^4$-H, K$^5$-H, or K$^6$-H, wherein K$^1$, K$^2$, K$^3$, K$^4$, K$^5$, and K$^6$, are as defined previously, to give a corresponding metal-ligand complex of formula (I) wherein two of the methyls (bound to hafnium) of the trimethyl hafnium-ligand complex has been replaced by K$^1$, K$^2$, K$^3$, K$^4$, K$^5$, or K$^6$, respectively.

Examples A to D

Preparation of poly(ethylene 1-octene) Copolymers (P1) to (P4), Respectively

As summarized in Table 1, using micromole (μ) of the Metal-ligand Complex (1) or (4), micromole of the activating co-catalyst MDATPB, micromoles of the activating co-catalyst MMAO, and grams of ethylene in the aforementioned general ethylene/-1-octene copolymerization procedure respectively yield grams of product poly(ethylene 1-octene) copolymer (P1) to (P4), which are each recovered by drying for about 12 hours in a temperature ramped vacuum oven with a final set point of 140° C.

TABLE 1 ethylene/1-octene copolymerization reactant amounts and yields of copolymers.

| Ex. No. (Copolymer No.) | Metal-ligand Complex Number/metal | Amount Metal-ligand Complex (μmole) | Amount of MDATPB (μmole) | Amount of MMAO-3A (μmoles) | Amount ethylene added (g) | Yield of Copolymer (g) |
|---|---|---|---|---|---|---|
| A (P1) | (1)/Zr | 0.3 | 0.36 | 3 | 20.4 | 39.8 |
| B (P2) | (1)/Zr | 0.3 | 0.36 | 3 | 19.6 | 38.5 |
| C (P3) | (4)/Hf | 0.4 | 0.48 | 4 | 14.3 | 33.9 |
| D (P4) | (4)/Hf | 0.4 | 0.48 | 4 | 14.4 | 29.0 |

Measure melting and crystallization temperatures of each poly(ethylene 1-octene) copolymer (e.g., P1) by DSC (DSC 2910, TA Instruments, Inc.). Separately, first heat a sample of each poly(ethylene 1-octene) copolymer (e.g., P1) from room temperature to 180° C. at a first heating rate of 10° C. per minute. After being held at this temperature for 4 minutes, cool the sample to −40° C. at a cooling rate of 10° C. per minute, hold at −40° C. for 4 minutes, and then heat to 160° C. at a second heating rate of 10° C. per minute.

Measure molecular weight of each poly(ethylene 1-octene) copolymer (e.g., P1) using a Polymer Labs™ 210 high temperature gel permeation calorimeter. Prepare a sample using 13 mg of poly(ethylene 1-octene) copolymer (e.g., P1) and diluting same with 16 mL of 1,2,4 trichlorobenzene (stabilized with BHT); heat and shake diluted sample at 160° C. for 2 hours. To determine mole percent (mol %) octene incorporation and density, separately deposit 140 μL of each polymer solution onto a silica wafer, heat at 140° C. until the TCB dries, and analyze the dried sample using a Nicolet Nexus 670 FT-IR with 7.1 version software equipped with an AutoPro auto sampler.

Results are shown below in Table 2. In Table 2, "Ex. No." means Example Number, μmoles means micromoles, "g-poly/g-metal" means grams of polymer produced per gram of complex used), T$_m$, weight average molecular weight (M$_w$) in grams (g), number average molecular weight (M$_n$), and M$_w$/M$_n$ are as defined previously.

TABLE 2 ethylene/1-octene copolymerizations results.

| Ex. No. (Copolymer No.) | Catalyst Efficiency (g-poly/g-metal) | $T_m$ (°C.) | Co-Polymer $M_w$ (GPC) (g) | Co-Polymer $M_w/M_n$ (GPC) | Co-Polymer Density (FT-IR) (g/mL) | mole % octene residuals in Co-Polymer (FT-IR) (mol %) |
|---|---|---|---|---|---|---|
| A (P1) | 1,454,000 | 114.7 | 452,000 | 3.4 | 0.925 | 2.1 |
| B (P2) | 1,407,000 | 112.9 | 406,000 | 4.2 | 0.926 | 2.0 |
| C (P3) | 475,000 | 111.3 | 478,000 | 5.0 | 0.927 | 1.9 |
| D (P4) | 406,000 | 111.5 | 906,000 | 4.2 | 0.928 | 1.7 |

Examples E to H

Preparation of poly(ethylene 1-octene) Copolymers (P5) to (P8), Respectively

In a manner similar to the procedure of Example A except in separate experiments using a different one of the hafnium-ligand complexes (L1), (G1), (D1), and (H1) instead of the zirconium-ligand complex (1), the poly(ethylene 1-octene) copolymers (P5) to (P8) (structures not shown) can be respectively prepared.

As shown by the above Examples, the catalysts of the second embodiment show beneficial catalyst efficiencies as polymerization catalysts (e.g., higher grams of polymer produced per gram of metal-ligand complexes of formula (I) that are used to prepare the catalysts of the second embodiment) and produce polyolefins, including polyolefin copolymers, having beneficially higher $M_w$, $M_n$, or both compared to $M_w$ or $M_n$ of conventional polyolefins.

While the invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims

What is claimed is:

1. A metal-ligand complex of formula (I):

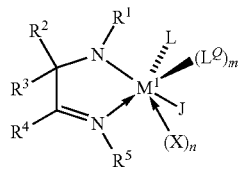

(I)

wherein:
 each $L^Q$ is absent or is L;
 each L independently is absent or is halogen atom, hydrogen atom, $(C_1$-$C_{40})$hydrocarbylC(O)N(H)—, $(C_1$-$C_{40})$hydrocarbylC(O)N(($C_1$-$C_{20})$hydrocarbyl), $(C_1$-$C_{40})$hydrocarbylC(O)O—, $(C_1$-$C_{40})$hydrocarbyl, $(C_1$-$C_{40})$heterohydrocarbyl, $R^K R^L N$—, $R^L O$—, $R^L S$—, or $R^K R^L P$—, wherein each $R^K$ and $R^L$ independently is hydrogen, $(C_1$-$C_{40})$hydrocarbyl, $[(C_1$-$C_{10})$hydrocarbyl$]_3$Si, $[(C_1$-$C_{10})$hydrocarbyl$]_3$Si($C_1$-$C_{10}$)hydrocarbyl, or $(C_1$-$C_{40})$heterohydrocarbyl, or $R^K$ and $R^L$ are taken together to form a $(C_2$-$C_{40})$hydrocarbylene or $(C_1$-$C_{40})$heterohydrocarbylene, or L and $L^Q$ are taken together to form $(R^D)_2C$=$C(R^D)$—$C(R^D)$=$C(R^D)_2$, each L independently being a monoanionic moiety that is bonded to $M^1$;

n is an integer of from 0 to 3;

each X independently is absent or is a neutral Lewis base group that is $R^X N R^K R^L$, $R^K O R^L$, $R^K S R^L$, or $R^X P R^K R^L$, wherein each $R^X$ independently is hydrogen, $(C_1$-$C_{40})$hydrocarbyl, $[(C_1$-$C_{10})$hydrocarbyl$]_3$Si, $[(C_1$-$C_{10})$hydrocarbyl$]_3$Si($C_1$-$C_{10}$)hydrocarbyl, or $(C_1$-$C_{40})$heterohydrocarbyl and each $R^K$ and $R^L$ independently is as defined above;

J is a monoanionic moiety of any one of formulas ($J^1$) to ($J^7$):

$R^K R^L R^X P$=N— ($J^1$), wherein each of $R^K$, $R^L$, and $R^X$ independently is as defined above;

$R^K R^L B$—O— ($J^2$), wherein each of $R^K$ and $R^L$ independently is as defined above;

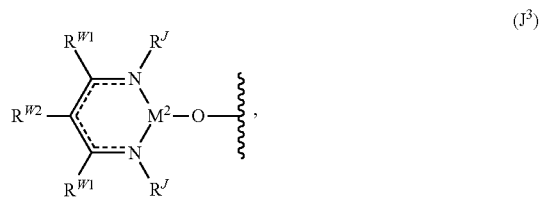

wherein --- indicates two delocalized pi bonds; each $R^{W1}$ and $R^{W2}$ independently is $R^X$; $M^2$ is Al—$R^A$, Ga—$R^A$, or Zn, wherein each $R^A$ independently is $(C_1$-$C_{40})$alkyl, $R^K R^L N$—, or $R^L O$—; and each $R^J$ independently is $(C_6$-$C_{12})$aryl;

$R^K R^L N$—O— ($J^4$), wherein each of $R^K$ and $R^L$ independently is as defined above;

$R^K R^L C$=N— ($J^5$), wherein each of $R^K$ and $R^L$ independently is as defined above;

$R^K(R^L R^X N)C$=N— ($J^6$), wherein each of $R^K$, $R^L$, and $R^X$ independently is as defined above; and $(R^L R^X N)_2 C$=N— ($J^7$), wherein each of $R^K$, $R^L$, and $R^X$ independently is as defined above; or n is 1, 2, or 3 and one X and J are taken together to form a monoanionic bidentate moiety $X^J$-$J^X$ of any one of formulas ($K^1$) to ($K^6$):

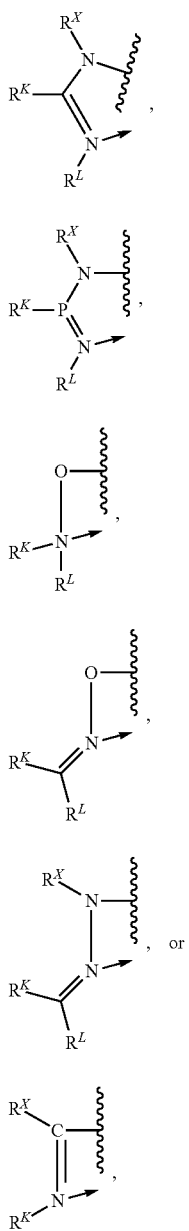

wherein each of $R^K$, $R^L$, and $R^X$ independently is as defined above;

$M^1$ is a Group 4 metal, which means that $M^1$ is hafnium (Hf), zirconium (Zr), or titanium (Ti), the metal being in a formal oxidation state of +3 or +4;

m is an integer of from 0 to 3;

each $R^1$ independently is H, $(C_1-C_{40})$hydrocarbyl, or $(C_1-C_{40})$heterohydrocarbyl;

each of $R^2$, $R^3$, and $R^4$ independently is $(C_1-C_{40})$hydrocarbyl, $(C_1-C_{40})$hydrocarbylO—, $(C_1-C_{40})$hydrocarbylS-, $(C_1-C_{40})$hydrocarbylS(O)—, $(C_1-C_{40})$hydrocarbylS(O)$_2$—, $((C_1-C_{40})$hydrocarbyl)$_2$N—, $((C_1-C_{40})$hydrocarbyl)$_2$P—, or $(C_1-C_{40})$heterohydrocarbyl; or $R^4$ is as defined previously and $R^2$ and $R^3$ are taken together to form a diradical of formula $(R^{23})$:

wherein each of $R^{2A}$ and $R^{3A}$ independently is $(C_1-C_{40})$hydrocarbyl, $(C_1-C_{40})$hydrocarbylO—, $(C_1-C_{40})$hydrocarbylS-, $(C_1-C_{40})$hydrocarbylS(O)—, $(C_1-C_{40})$hydrocarbylS(O)$_2$—, $((C_1-C_{40})$hydrocarbyl)$_2$N—, $((C_1-C_{40})$hydrocarbyl)$_2$ P—, or $(C_1-C_{40})$heterohydrocarbyl;

each $R^5$ independently is $(C_1-C_{40})$hydrocarbyl or $(C_1-C_{40})$heterohydrocarbyl;

or $R^1$ and $R^2$; $R^1$ and $R^4$; $R^1$ and $R^{2A}$; $R^2$ and $R^3$; $R^2$ and $R^5$; $R^{2A}$ and $R^{3A}$; $R^{2A}$ and $R^5$; $R^3$ and $R^4$; $R^{3A}$ and $R^4$; $R^4$ and $R^5$; $R^1$ or $R^5$ and an $R^K$ of X or J; or $R^1$ or $R^5$ and an $R^L$ of L or J are taken together to form a $(C_1-C_{40})$hydrocarbylene or $(C_1-C_{40})$heterohydrocarbylene and the remainder thereof are as defined above;

or $R^1$ or $R^5$ and L are taken together to form $(C_1-C_{40})$hydrocarbylene-C(O)N(H)—, $(C_1-C_{40})$hydrocarbylene-C(O)N($(C_1-C_{20})$hydrocarbyl), $(C_1-C_{40})$hydrocarbylene-C(O)O—, $(C_1-C_{40})$hydrocarbylene, or $(C_1-C_{40})$heterohydrocarbylene, and the remainder thereof are as defined above;

or any three or four of $R^1$ to $R^5$, $R^{2A}$, $R^{3A}$, $R^K$ of X or J, and $R^L$ of L or J are taken together to form a respective trivalent or tetravalent analog of $(C_1-C_{40})$hydrocarbylene or $(C_1-C_{40})$heterohydrocarbylene, and the remainder thereof are as defined above;

or $R^1$ or $R^5$ and any one or two of the remainder of $R^1$ to $R^5$, $R^{2A}$, $R^{3A}$, $R^K$ of X or J, and $R^L$ of L or J are taken together with L to form a respective trivalent or tetravalent analog of $(C_1-C_{40})$hydrocarbylene-C(O)N(H)—, $(C_1-C_{40})$hydrocarbylene-C(O)N($(C_1-C_{20})$hydrocarbyl), $(C_1-C_{40})$hydrocarbylene-C(O)O—, $(C_1-C_{40})$hydrocarbylene, or $(C_1-C_{40})$heterohydrocarbylene; and the remainder of $R^1$ to $R^5$, $R^{2A}$, $R^{3A}$, $R^K$ of X or J, $R^L$ of L or J, and L are as defined above;

each of the aforementioned $(C_6-C_{12})$aryl, $(C_1-C_{10})$hydrocarbyl, $(C_1-C_{20})$hydrocarbyl, $(C_1-C_{40})$hydrocarbyl, $(C_1-C_{40})$heterohydrocarbyl, $(C_1-C_{40})$hydrocarbylene, $(C_2-C_{40})$hydrocarbylene, and $(C_1-C_{40})$heterohydrocarbylene independently is the same or different and is unsubstituted or substituted with one or more substituents $R^S$;

each $R^S$ independently is halogen atom, polyfluoro, perfluoro, unsubstituted $(C_1-C_{18})$hydrocarbyl, $F_3C$—, $FCH_2O$—, $F_2HCO$—, $F_3CO$—, oxo, $R_3Si$—, RO—, RS—, RS(O)—, RS(O)$_2$—, $R_2P$—, $R_2N$—, $R_2C$=N—, NC—, RC(O)O—, ROC(O)—, RC(O)N(R)—, or $R_2NC(O)$—, wherein each R independently is an unsubstituted $(C_1-C_{18})$hydrocarbyl;

each ～ independently indicates a bond fragment; and each L, $L^Q$, and m being selected, depending on the formal oxidation state of metal $M^1$, such that the metal-ligand complex of formula (I) is, in aggregate, neutral.

2. The metal-ligand complex as in claim 1, wherein $R^2$ and $R^3$ are taken together to form the diradical of formula $(R^{23})$:

(R23)

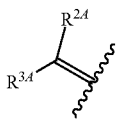

so that the metal-ligand complex of formula (I) is a metal-ligand complex of formula (II-B), (II-E), (II-A), (II-H), or (II-I):

(II-B)

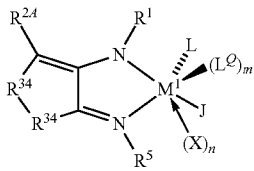

Wherein in formula (II-B) each $R^{34}$ independently is $C(R^{35})_2$, O, S, S(O), S(O)$_2$, N($R^N$), Si($R^C$)$_2$, or P($R^P$), wherein each $R^{35}$ independently is H or (C$_1$-C$_{20}$)hydrocarbyl, and each $R^N$, $R^C$, and $R^P$ independently is (C$_1$-C$_{20}$)hydrocarbyl;

(II-E)

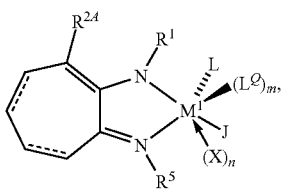

wherein in formula (II-E) each ---- is absent or is a pi-bond;

(II-A)

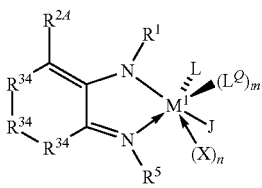

wherein in formula (II-A) each $R^{34}$ independently is $C(R^{35})_2$, O, S, S(O), S(O)$_2$, N($R^N$), Si($R^C$)$_2$, or P($R^P$), wherein each $R^{35}$ independently is H or (C$_1$-C$_{20}$)hydrocarbyl, and each $R^N$, $R^C$, and $R^P$ independently is (C$_1$-C$_{20}$)hydrocarbyl;

(II-H)

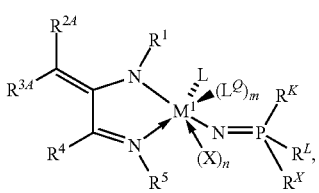

wherein in formula (II-H) $R^{2A}$ is H or (C$_1$-C$_{40}$)hydrocarbyl and $R^{3A}$ and $R^4$ are taken together to form a (C$_1$-C$_{20}$)hydrocarbylene or (C$_1$-C$_{20}$)heterohydrocarbylene; or (II-I)

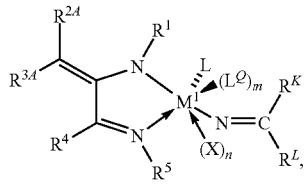

wherein in formula (II-I) $R^{2A}$ is H or (C$_1$-C$_{40}$)hydrocarbyl and $R^{3A}$ and $R^4$ are taken together to form a (C$_1$-C$_{20}$)hydrocarbylene or (C$_1$-C$_{20}$)heterohydrocarbylene.

3. The metal-ligand complex as claim 2, wherein in formulas (II-H) and (II-I) $R^{3A}$ and $R^4$ are taken together to form a (C$_2$-C$_5$)hydrocarbylene or (C$_1$-C$_4$)heterohydrocarbylene, each of $R^1$ and $R^5$ independently is (C$_1$-C$_{10}$)hydrocarbyl, and $R^{2A}$ is H or (C$_1$-C$_{10}$)alkyl.

4. The metal-ligand complex as in claim 1 that is a metal-ligand complex of formula (III):

(III)

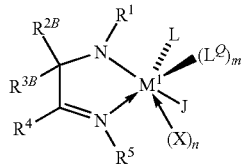

wherein each of $R^{2B}$, $R^{3B}$, and $R^4$ independently is (C$_1$-C$_{40}$)hydrocarbyl, (C$_1$-C$_{40}$)hydrocarbylO—, (C$_1$-C$_{40}$)hydrocarbylS-, (C$_1$-C$_{40}$)hydrocarbylS(O)—, (C$_1$-C$_{40}$)hydrocarbylS(O)$_2$—, ((C$_1$-C$_{40}$)hydrocarbyl)$_2$N—, ((C$_1$-C$_{40}$)hydrocarbyl)$_2$P—, or (C$_1$-C$_{40}$)heterohydrocarbyl.

5. The metal-ligand complex as in claim 1, wherein in formula (I), J is $R^K R^L R_X P=N$— ($J^1$) or $R^K R^L C=N$— ($J^5$).

6. The metal-ligand complex as in claim 1, wherein n is 0 and X is absent.

7. The metal-ligand complex as in claim 1, wherein n is 1 and X and J are taken together to form the aforementioned monoanionic bidentate moiety $X^J$-$J^X$ of any one of formulas ($K^1$) to ($K^6$), such a metal-ligand complex being of formula (IV):

(IV)

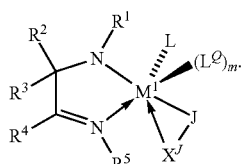

8. The metal-ligand complex as in claim 1, wherein each of $R^K$, $R^L$, and $R^X$ independently is (C$_1$-C$_{20}$)hydrocarbyl.

9. The metal-ligand complex as in claim 1, wherein each of L and $L^Q$ independently is (C$_1$-C$_5$)alkyl, trimethylsilylmethyl, or benzyl.

10. A catalyst comprising, or prepared from, one or more metal-ligand complexes of claim 1 and one or more activating co-catalysts, or a reaction product thereof, wherein the ratio of total number of moles of the one or more metal-ligand complexes to total number of moles of the one or more activating co-catalyst is from 1:10,000 to 100:1.

11. A process of preparing a polyolefin, the process comprising a step of contacting at least one polymerizable olefin to the catalyst of claim 10 under olefin-polymerizing conditions sufficient to polymerize at least some of the at least one polymerizable olefin, thereby producing a polyolefin therefrom.

12. The metal-ligand complex as in claim 2, wherein in formula (II-B), (II-E), or (II-A), J is $R^K R^L R^X P=N—$ ($J^1$) or $R^K R^L C=N—$ ($J^5$).

13. The metal-ligand complex as in claim 4, wherein in formula (III), J is $R^K R^L R^X P=N—$ ($J^1$) or $R^K R^L C=N—$ ($J^5$).

14. A metal-ligand complex of any one of formulas (1) to (12):

(1)
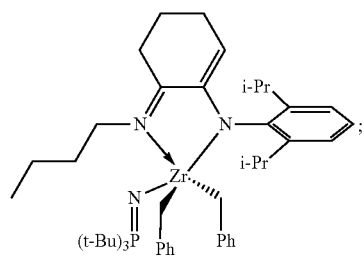

(2)
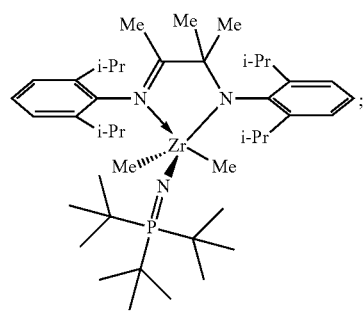

(3)
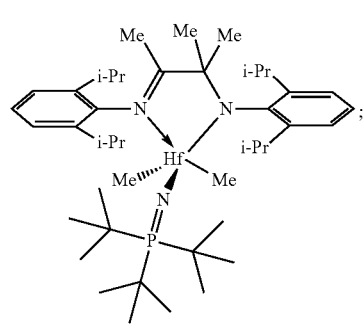

(4)
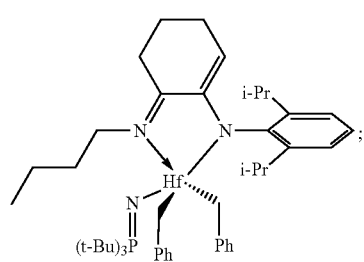

(5)
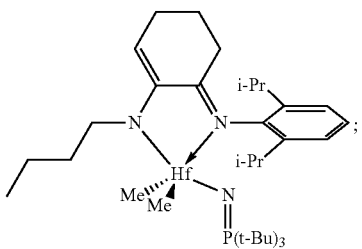

(6)
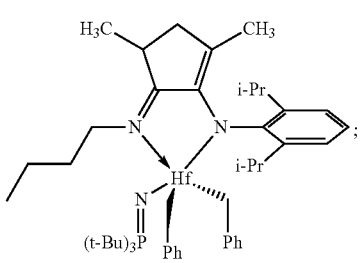

(7)
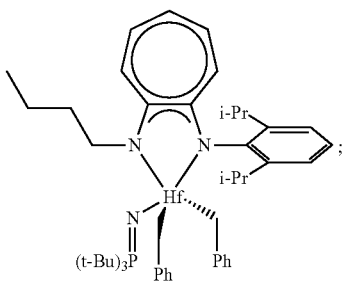

(8)
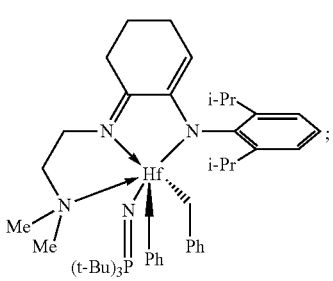

(9)
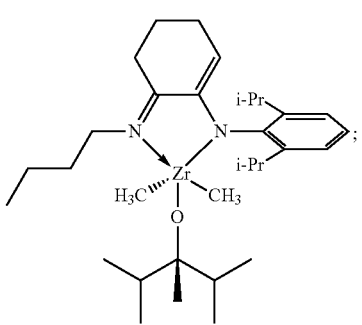

-continued
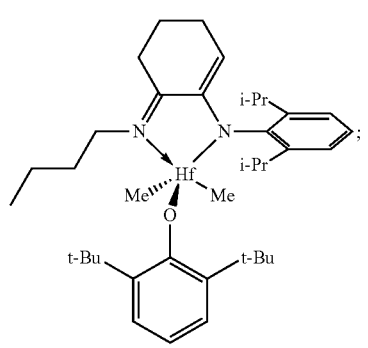
(10)
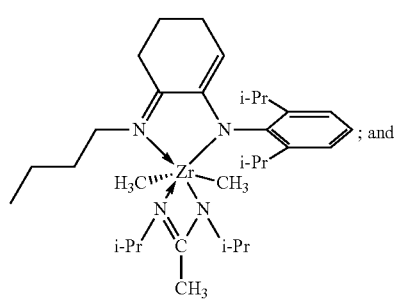
(11)
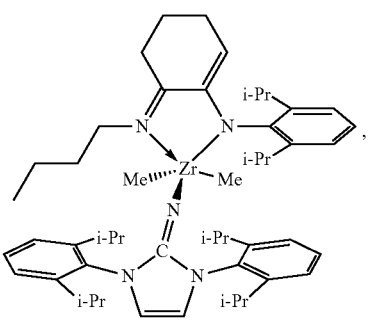
(12)
wherein Me means methyl; i-Pr means iso-propyl; t-Bu means 1,1-dimethylethyl; and Ph means phenyl.
* * * * *